US012564503B2

(12) United States Patent (10) Patent No.: US 12,564,503 B2
Herr et al. (45) **Date of Patent: \*Mar. 3, 2026**

(54) IMPLEMENTING A STAND-UP SEQUENCE USING A LOWER-EXTREMITY PROSTHESIS OR ORTHOSIS

(71) Applicant: Otto Bock Healthcare LP, Austin, TX (US)

(72) Inventors: Hugh M. Herr, Somerville, MA (US); Richard J. Casler, Jr., Lowell, MA (US)

(73) Assignee: Otto Bock Healthcare LP, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/325,683

(22) Filed: May 30, 2023

(65) Prior Publication Data

US 2023/0380995 A1     Nov. 30, 2023

Related U.S. Application Data

(63) Continuation of application No. 16/406,048, filed on May 8, 2019, now Pat. No. 11,701,244, which is a
(Continued)

(51) Int. Cl.
*A61H 3/00* (2006.01)
*A61F 2/60* (2006.01)
(Continued)

(52) U.S. Cl.
CPC .................. *A61F 2/72* (2013.01); *A61F 2/60* (2013.01); *A61F 2/6607* (2013.01); *H02K 7/06* (2013.01); *A61F 2002/5003* (2013.01); *A61F 2002/5007* (2013.01); *A61F 2002/5018* (2013.01); *A61F 2002/503* (2013.01); *A61F 2002/5087* (2013.01); *A61F 2002/701* (2013.01); *A61F 2002/704* (2013.01); *A61F 2002/7625* (2013.01); *A61F 2002/7635* (2013.01); *A61F 2002/7645* (2013.01); *A61F 2002/7665* (2013.01); *H02K 7/116* (2013.01)

(58) Field of Classification Search
CPC .......... A61H 1/02; A61H 1/0262; A61H 3/00; A61H 2003/007; B25J 9/0006; A61B 5/112; A61B 5/1123; A61B 5/1126
See application file for complete search history.

(56) References Cited

U.S. PATENT DOCUMENTS 4,697,808 A * 10/1987 Larson ................. A61H 1/0237
482/901
5,282,460 A * 2/1994 Boldt ....................... B25J 9/146
403/119
(Continued)

*Primary Examiner* — Justine R Yu
*Assistant Examiner* — Christopher E Miller
(74) *Attorney, Agent, or Firm* — Goodwin Procter LLP

(57) ABSTRACT

Knee orthoses or prostheses can be used to automatically, when appropriate, initiate a stand-up sequence based on the position of a person's knee with respect to the person's ankle while the person is in a seated position. When the knee is moved to a position that is forward of the ankle, at least one actuator of the orthosis or prosthesis is actuated to help raise the person from the seated position to a standing position.

15 Claims, 68 Drawing Sheets

Related U.S. Application Data continuation of application No. 14/034,005, filed on Sep. 23, 2013, now Pat. No. 10,285,828, which is a continuation of application No. 12/872,425, filed on Aug. 31, 2010, now abandoned, which is a continuation-in-part of application No. 12/552,028, filed on Sep. 1, 2009, now abandoned.

(60) Provisional application No. 61/238,305, filed on Aug. 31, 2009, provisional application No. 61/231,754, filed on Aug. 6, 2009, provisional application No. 61/161,999, filed on Mar. 20, 2009, provisional application No. 61/094,125, filed on Sep. 4, 2008.

(51) Int. Cl.

| | |
|---|---|
| *A61F 2/66* | (2006.01) |
| *A61F 2/72* | (2006.01) |
| *H02K 7/06* | (2006.01) |
| *A61F 2/50* | (2006.01) |
| *A61F 2/70* | (2006.01) |
| *A61F 2/76* | (2006.01) |
| *H02K 7/116* | (2006.01) |

(56) References Cited

U.S. PATENT DOCUMENTS

| | | | | |
|---|---|---|---|---|
| 6,821,233 | B1 * | 11/2004 | Colombo | A61H 1/0262 |
| | | | | 601/5 |
| 7,278,954 | B2 * | 10/2007 | Kawai | B25J 9/1638 |
| | | | | 482/8 |
| 7,390,309 | B2 * | 6/2008 | Dariush | B25J 9/0006 |
| | | | | 601/5 |
| 7,402,142 | B2 * | 7/2008 | Kawai | B62D 57/032 |
| | | | | 600/595 |
| 8,181,520 | B2 * | 5/2012 | Kadota | A61B 5/6828 |
| | | | | 601/33 |
| 8,251,930 | B2 * | 8/2012 | Ido | A63B 69/0028 |
| | | | | 601/5 |
| 2004/0167641 | A1 * | 8/2004 | Kawai | B25J 9/0006 |
| | | | | 700/63 |
| 2005/0070834 | A1 * | 3/2005 | Herr | A61F 2/70 |
| | | | | 602/28 |
| 2005/0080590 | A1 * | 4/2005 | Kawai | B25J 13/088 |
| | | | | 702/141 |
| 2006/0004299 | A1 * | 1/2006 | Endo | A61B 5/4528 |
| | | | | 600/595 |
| 2006/0149420 | A1 * | 7/2006 | Ikeuchi | B62D 57/032 |
| | | | | 700/245 |
| 2006/0195223 | A1 * | 8/2006 | Kawai | B62D 57/032 |
| | | | | 700/245 |
| 2006/0211956 | A1 * | 9/2006 | Sankai | A61F 5/0102 |
| | | | | 601/5 |
| 2007/0043449 | A1 * | 2/2007 | Herr | A61F 2/60 |
| | | | | 623/24 |
| 2007/0084278 | A1 * | 4/2007 | Kawal | A61B 5/1121 |
| | | | | 73/172 |
| 2007/0123997 | A1 * | 5/2007 | Herr | A61F 2/60 |
| | | | | 602/23 |
| 2007/0145930 | A1 * | 6/2007 | Zaier | B62D 57/032 |
| | | | | 318/568.12 |
| 2008/0039756 | A1 * | 2/2008 | Thorsteinsson | A61F 5/0123 |
| | | | | 600/595 |
| 2008/0161937 | A1 * | 7/2008 | Sankai | A61H 1/0255 |
| | | | | 623/25 |
| 2008/0234608 | A1 * | 9/2008 | Sankai | A61H 1/0262 |
| | | | | 601/5 |
| 2009/0265018 | A1 * | 10/2009 | Goldfarb | A61F 2/60 |
| | | | | 623/40 |
| 2009/0292369 | A1 * | 11/2009 | Kazerooni | A61H 3/00 |
| | | | | 128/845 |
| 2010/0076360 | A1 * | 3/2010 | Shimada | A61H 3/008 |
| | | | | 600/587 |
| 2010/0094188 | A1 * | 4/2010 | Goffer | A61H 1/0255 |
| | | | | 600/587 |
| 2010/0121232 | A1 * | 5/2010 | Sankai | A61H 1/00 |
| | | | | 600/587 |
| 2010/0130893 | A1 * | 5/2010 | Sankai | A63B 23/0494 |
| | | | | 600/587 |
| 2010/0217163 | A1 * | 8/2010 | Sankai | B25J 9/0006 |
| | | | | 601/5 |
| 2010/0256537 | A1 * | 10/2010 | Menga | B25J 9/0006 |
| | | | | 601/34 |
| 2010/0271051 | A1 * | 10/2010 | Sankai | A61B 5/1038 |
| | | | | 324/679 |

* cited by examiner

| | WALKING STATE | | | | |
|---|---|---|---|---|---|
| | 1. CONTROLLED PLANTAR FLEXION | 2. CONTROLLED DORSIFLEXION | 3. POWERED PLANTAR FLEXION | 4. EARLY SWING | 5. LATE SWING |
| | 102 | 106 | 110 | 114 | 118 |
| PHASE | STANCE | | | SWING | |
| % OF CYCLE | 60% | | | 40% | |
| INITIATING EVENT | FOOT-STRIKE | FOOT-FLAT | MAXIMUM DORSIFLEXION | TOE-OFF | VERTICAL ANKLE VELOCITY IS APPROXIMATELY ZERO |
| FUNCTION | IMPEDANCE (SPRING-DOMINATED) | TORQUE SOURCE + NONLINEAR IMPEDANCE | TORQUE SOURCE + IMPEDANCE | POSITION CONTROL | LINEAR SPRING |

FIG. 1A $$\beta = -\theta - \gamma$$

WORLD-REFERENCED VERTICAL

WORLD-REFERENCED HORIZONTAL

INERTIAL SHANK TILT ANGLE, γ
ANKLE JOINT ANGLE, θ
FOOT SLOPE ANGLE, β

LIFT OR HIGH-HEEL

620 - LEVEL GROUND
624 - UP 5° RAMP
628 - DOWN 5° RAMP
632 - UP 10° RAMP
636 - DOWN 10° RAMP
640 - UP STAIRS
644 - DOWN STAIRS $$\hat{\phi}(t) = \tan^{-1}\left(\frac{(^w p_{heel}(t) - {}^w p_{toe}(0))z}{(^w p_{heel}(t) - {}^w p_{toe}(0))y}\right)$$

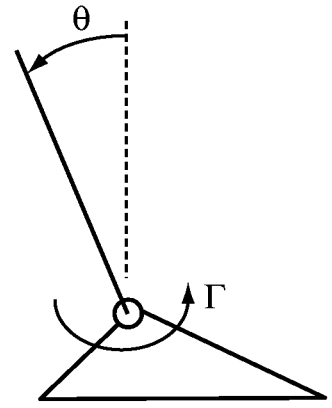

MECHANICAL IMPEDANCE RELATION $$\Gamma = -(k(\theta - \theta_0) + b\dot{\theta} + j\ddot{\theta})$$

FIG. 10D

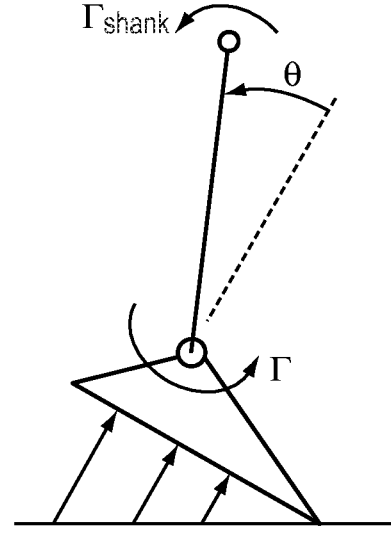

REFLEX RELATION INCLUDING
POSITIVE TORQUE AND VELOCITY FEEDBACK $$\Gamma_{reflex}(\alpha) = \Gamma_{Torque\ reflex}(\alpha) + \Gamma_{Velocity\ reflex}(\alpha)$$

WHERE $$\Gamma_{Torque\ reflex} = \alpha_0(\hat{\Gamma}_{shank})^{\alpha_1}$$

$$\Gamma_{Velocity\ reflex} = \alpha_2(\dot{\theta})^{\alpha_3}$$

FIG. 10E $$\Gamma_{CM} = {}^{W}r_{ZMP_l} \times f_l + {}^{W}r_{ZMP_t} \times f_t$$

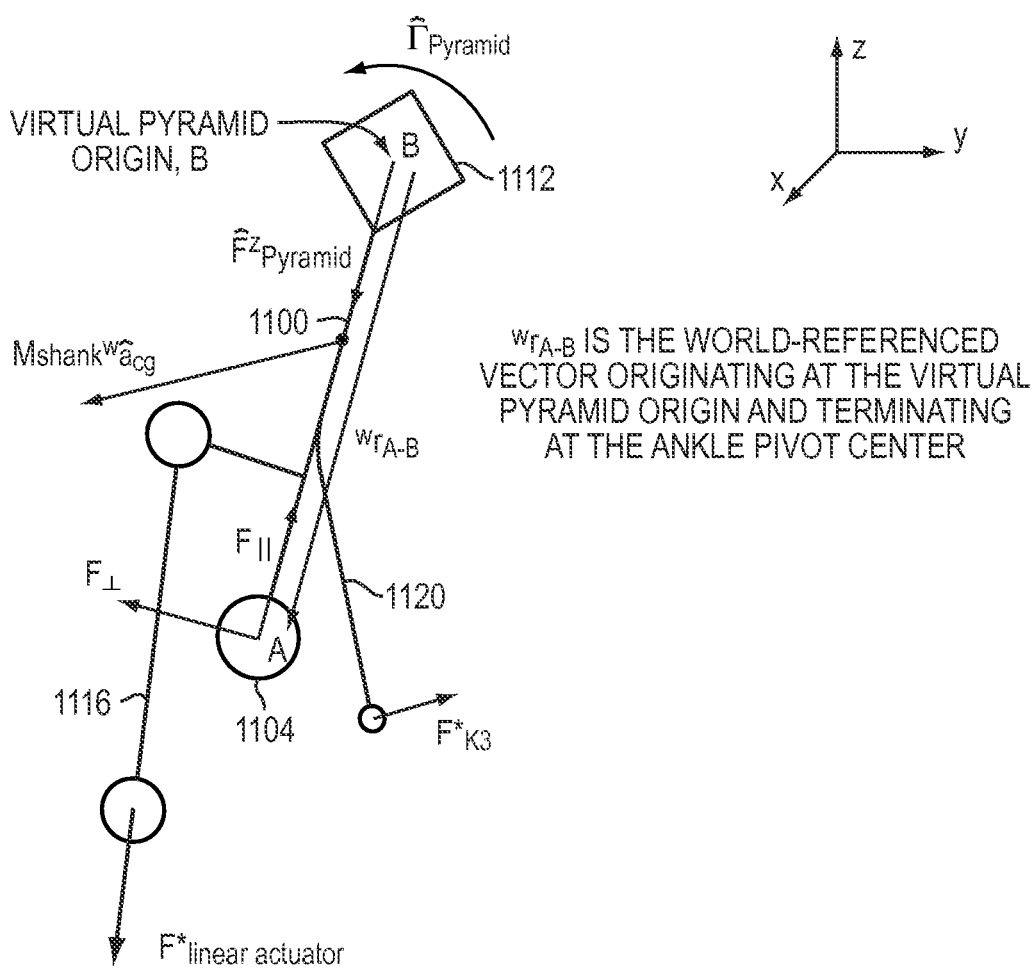

VIRTUAL PYRAMID ORIGIN, B $\hat{\Gamma}_{Pyramid}$ $\hat{F}^z_{Pyramid}$

1112

1100

$Mshank^w\hat{a}_{cg}$ $^w r_{A-B}$ $F_{||}$ $F_\perp$

1120

A

1116

1104

$F^*_{K3}$ $F^*_{linear\ actuator}$ $^w r_{A-B}$ IS THE WORLD-REFERENCED VECTOR ORIGINATING AT THE VIRTUAL PYRAMID ORIGIN AND TERMINATING AT THE ANKLE PIVOT CENTER NOTE:
* DENOTES A VARIABLE WHICH CAN BE CALCULATED USING CONTROL INPUTS AND MODEL PARAMETERS
$^\frown$ DENOTES A VARIABLE WHICH IS MEASURED

FIG. 11C

RIGID BODY POSE OF THE FOOT
AS DERIVED FROM THE WORLD-REFERENCED
POSE OF THE FOOT, $^{W}T_{foot}$

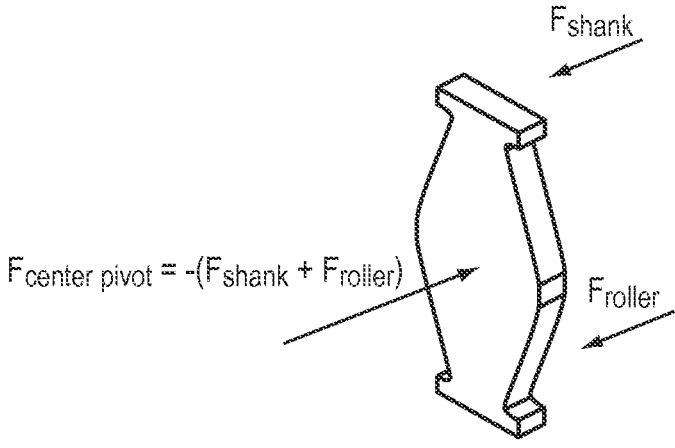
$F_{center\ pivot} = -(F_{shank} + F_{roller})$
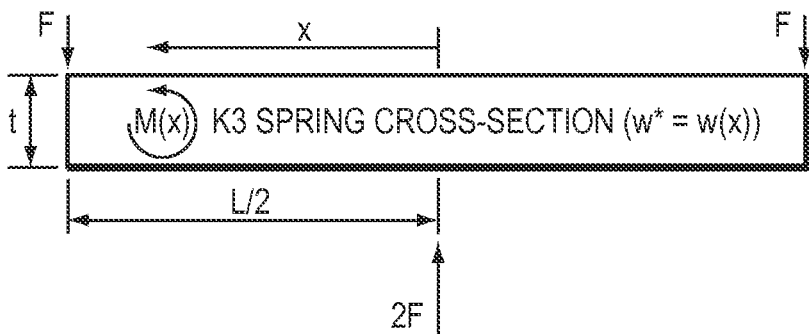
FIG. 17D

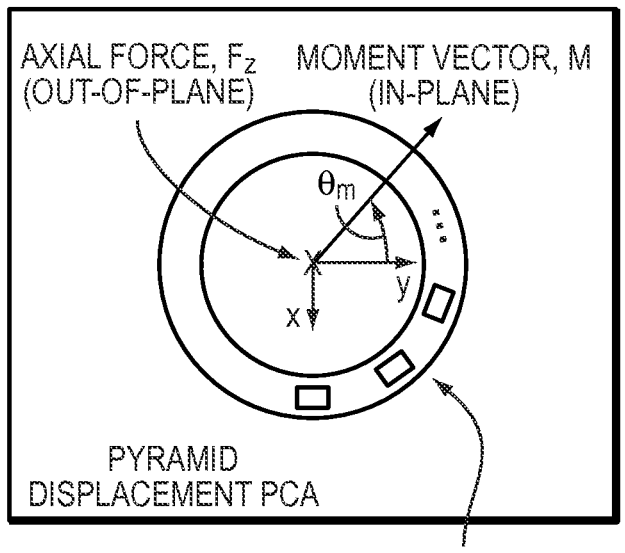

AXIAL FORCE, $F_z$ (OUT-OF-PLANE)

MOMENT VECTOR, M (IN-PLANE)

$\theta_m$

PYRAMID DISPLACEMENT PCA

DISPLACEMENT SENSOR ARRAY (CIRCULAR ARRAY SHOWN)

DISPLACEMENT $d(\theta)$

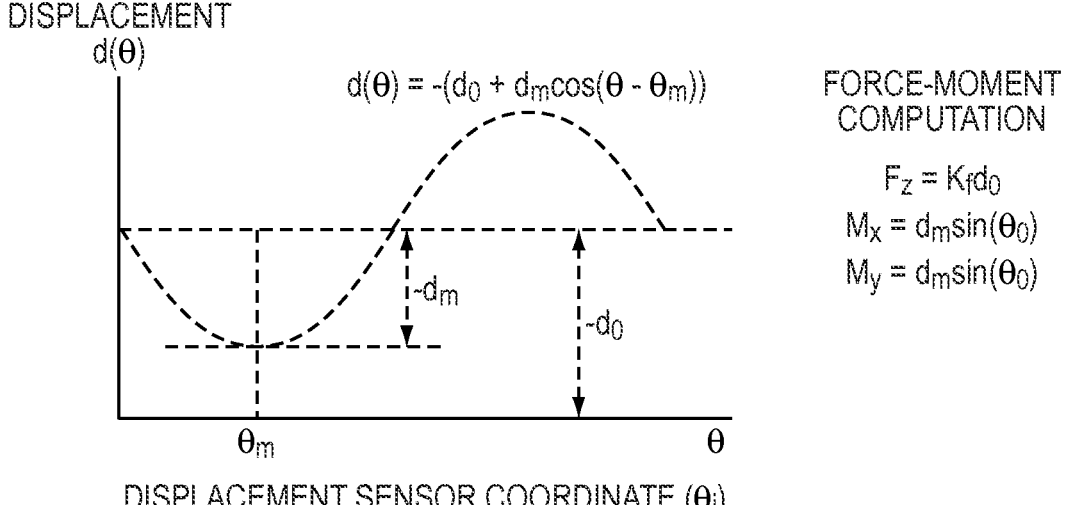

$$d(\theta) = -(d_0 + d_m\cos(\theta - \theta_m))$$

FORCE-MOMENT COMPUTATION $$F_z = K_f d_0$$
$$M_x = d_m\sin(\theta_0)$$
$$M_y = d_m\sin(\theta_0)$$

~$d_m$

~$d_0$ $\theta_m$ $\theta$

DISPLACEMENT SENSOR COORDINATE ($\theta_i$)

FIG. 17G $$W_t = \int_0^{T} f_l \cdot v_{CM} dt + \int_0^{T} f_t \cdot v_{CM} dt$$

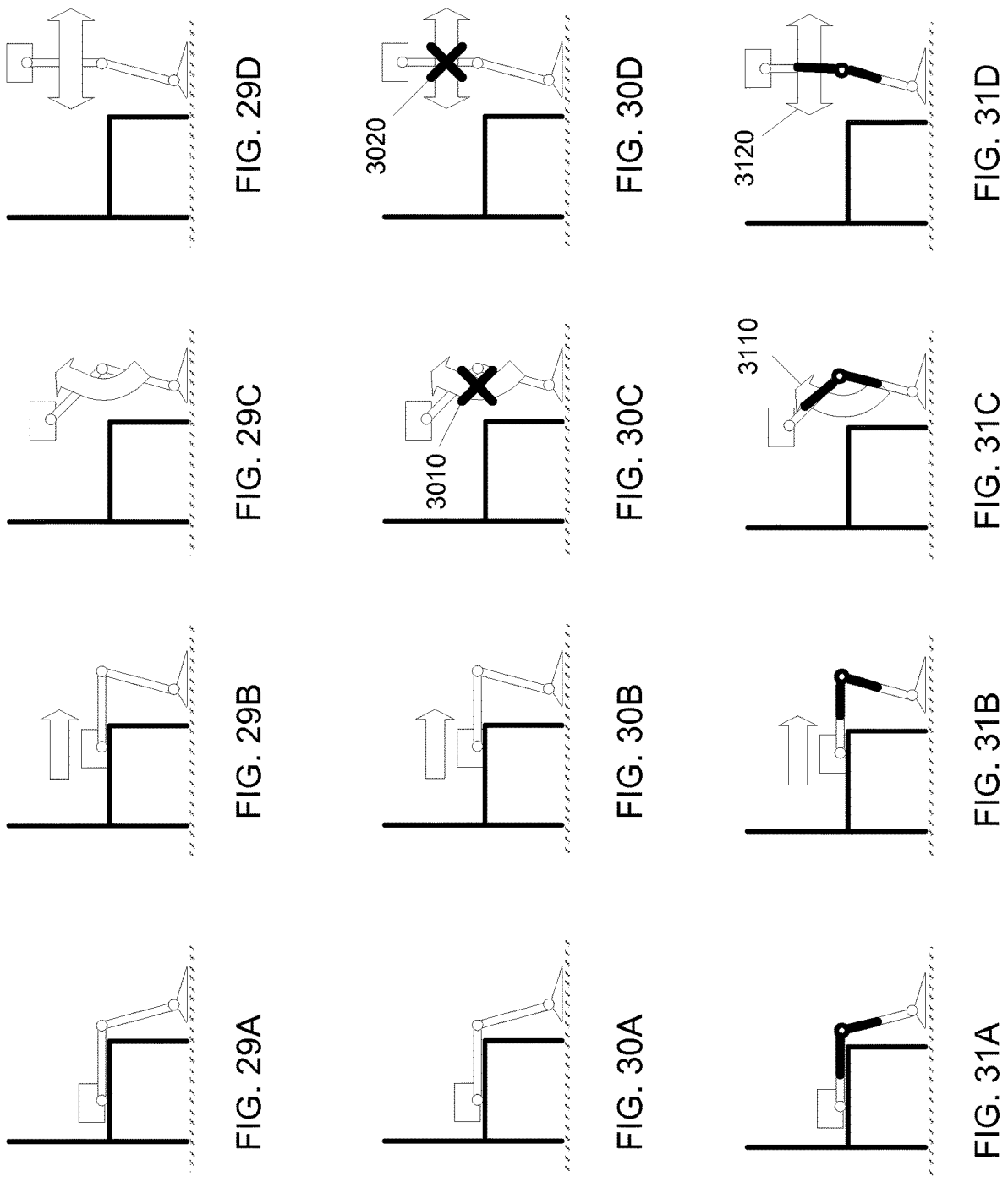

IMPLEMENTING A STAND-UP SEQUENCE USING A LOWER-EXTREMITY PROSTHESIS OR ORTHOSIS

RELATED APPLICATIONS

This application is a continuation of U.S. patent application Ser. No. 16/406,048, filed on May 8, 2019, which is a continuation of U.S. patent application Ser. No. 14/034,005, filed on Sep. 23, 2013, now U.S. Pat. No. 10,258,828, which is a continuation of U.S. patent application Ser. No. 12/872, 425, filed Aug. 31, 2010, which claims the benefit of U.S. Provisional Application 61/238,305, filed Aug. 31, 2009; and this application is a continuation in part of U.S. patent application Ser. No. 12/552,028, filed Sep. 1, 2009, which claims priority to U.S. Provisional Application 61/094,125, filed Sep. 4, 2008, U.S. Provisional Application 61/161,999, filed on Mar. 20, 2009, and U.S. Provisional Application 61/231,754, filed on Aug. 6, 2009. The entire contents of each of the above-identified applications is incorporated herein by reference in their entirety.

TECHNICAL FIELD

This invention relates generally to lower-extremity prosthetic, orthotic and exoskeleton apparatus, components thereof, and methods for controlling the same.

BACKGROUND

Over 100,000 people in the United States lose their feet through amputation every year. Many hundreds of thousands suffer this debilitating loss world-wide. Additionally, there are 700,000 individuals that survive a stroke each year in the United States often causing a variety of lower limb patholo-gies that constrain ambulation. Until recently, lower-extrem-ity prosthetic and orthotic systems have employed predomi-nantly passive or low-power mechanisms incapable of delivering the non-conservative positive work on each stride that the body needs to achieve an economical walking motion even on flat terrain-let alone on uneven surfaces such as stairs and steps.

It is helpful to understand the normal biomechanics associated with a gait cycle of a subject to appreciate the requirements of lower-extremity prosthetic, orthotic and exoskeleton apparatus. Specifically, the function of human ankle under sagittal plane rotation is described below for different locomotor conditions.

The mechanical characteristics of conventional passive ankle/foot prostheses ("AFPs") like the Ossur Flex-Foot® remain essentially constant throughout the life of the device. U.S. Patent Published Application No. US 2006/0249315 ("the '315 application") represented a significant advance over those conventional AFPs. The '315 application, the entire contents of which are hereby incorporated by refer-ence in its entirety, recognized that performance can be improved by dividing the walking cycle into five phases, and by optimizing the mechanical characteristics of the device independently for each of those five phases.

FIG. 1A is schematic illustration of the different phases of a subject's gait cycle over level ground. The gait cycle is typically defined as beginning with the heel strike of one foot and ending at the next heel strike of the same foot. The gait cycle is broken down into two phases: the stance phase (about 60% of the gait cycle) and the subsequent swing phase (about 40% of the gait cycle). The swing phase represents the portion of the gait cycle when the foot is off the ground. The stance phase begins at heel-strike when the heel touches the floor and ends at toe-off when the same foot rises from the ground surface. The stance phase is separated into three sub-phases: Controlled Plantarflexion (CP), Con-trolled Dorsiflexion (CD), and Powered Plantarflexion (PP).

CP begins at heel-strike illustrated at 102 and ends at foot-flat at 106. CP describes the process by which the heel and forefoot initially make contact with the ground. Researchers have shown that CP ankle joint behavior is consistent with a linear spring response where joint torque is proportional to the displacement of the joint in relation to an equilibrium position of the joint position. The spring behav-ior is, however, variable; joint stiffness is continuously modulated by the body from step to step within the three sub-phases of stance and late swing state.

After the CP period, the CD phase continues until the ankle reaches a state of maximum dorsiflexion and begins powered plantarflexion PP as illustrated at 110. Ankle torque versus position during the CD period is described as a nonlinear spring where stiffness increases with increasing ankle position. The ankle stores the elastic energy during CD which is necessary to propel the body upwards and forwards during the PP phase.

The PP phase begins after CD and ends at the instant of toe-off illustrated at I 14. During PP, the ankle applies torque in accordance with a reflex response that catapults the body upward and forward. The catapult energy is then released along with the spring energy stored during the CD phase to achieve the high plantarflexion power during late stance. This catapult behavior is necessary because the work gen-erated during PP is more than the negative work absorbed during the CP and CD phases for moderate to fast walking speeds. The foot is lifted off the ground during the swing phase, from toe-off at 114 until the next heel strike at 118.

Because the kinematic and kinetic patterns at the ankle during stair ascent/descent are different from that of level-ground walking, a separate description of the ankle-foot biomechanics is presented in FIGS. 1B and 1C. FIG. 1B shows the human ankle biomechanics during stair ascent. The first phase of stair ascent is called Controlled Dorsi-flexion 1 (CD 1), which begins with foot strike in a dorsi-flexed position seen at 130 and continues to dorsiflex until the heel contacts the step surface at 132. In this phase, the ankle can be modeled as a linear spring. The second phase is Powered Plantar flexion 1 (PP 1), which begins at the instant of foot flat (when the ankle reaches its maximum dorsiflexion at 132) and ends when dorsiflexion begins once again at 134. The human ankle behaves as a torque actuator to provide extra energy to support the body weight.

The third phase is Controlled Dorsiflexion 2 (CD 2), in which the ankle dorsiflexes until heel-off at 136. For the CD 2 phase, the ankle can be modeled as a linear spring. The fourth and final phase is Powered Plantar flexion 2 (PP 2) which begins at heel-off 136 and continues as the foot pushes off the step, acting as a torque actuator in parallel with the CD 2 spring to propel the body upwards and forwards, and ends when the toe leaves the surface at 138 to begin the swing phase that ends at 140.

FIG. 1C shows the human ankle-foot biomechanics for stair descent. The stance phase of stair descent is divided into three sub-phases: Controlled Dorsiflexion 1 (CD 1), Controlled Dorsiflexion 2 (CO2), and Powered Plantar flex-ion (PP). CD1 begins at foot strike illustrated at 150 and ends at foot-flat 152. In this phase, the human ankle can be modeled as a variable damper. In CD2, the ankle continues to dorsiflex forward until it reaches a maximum dorsiflexion posture seen at 154. Here the ankle acts as a linear spring, storing energy throughout CD2. During PP, which begins at 154, the ankle plantar flexes until the foot lifts from the step at 156. In this final PP phase, the ankle releases stored CO2 energy, propelling the body upwards and forwards. After toe-off at 156, the foot is positioned controlled through the swing phase until the next foot strike at 158.

For stair ascent depicted in FIG. 1B, the human ankle-foot can be effectively modeled using a combination of an actuator and a variable stiffness mechanism. However, for stair descent, depicted in FIG. 1C, a variable damper needs also to be included for modeling the ankle-foot complex; the power absorbed by the human ankle is much greater during stair descent than the power released during stair ascent. Hence, it is reasonable to model the ankle as a combination of a variable-damper and spring for stair descent.

Conventional passive prosthetic, orthotic and exoskeleton apparatus do not adequately reproduce the biomechanics of a gait cycle. They are not biomimetic because they do not actively modulate impedance and do not apply the reflexive torque response; neither on level ground, ascending or descending stairs or ramps, or changing terrain conditions. A need therefore exists for improved lower-extremity prosthetic, orthotic and exoskeleton apparatus, components thereof, and methods for controlling the same.

SUMMARY

The inventions described herein relate generally to lower-extremity prosthetic, orthotic and exoskeleton apparatus. Typical use cases for various embodiments of the invention include, for example, metabolic augmentation, permanent assistance for subjects with a permanent limb pathology, or rehabilitation for wearers with temporary limb pathology.

One aspect of the invention relates to an active orthotic or prosthetic apparatus that includes a thigh member, a lower leg member, and a knee joint for connecting the thigh member to the lower leg member. The apparatus also includes a rotary motor with a motor shaft output, a motor drive transmission assembly coupled to the motor shaft output, and a drive transmission assembly coupled to the output of the motor drive transmission, with an output of the drive transmission assembly coupled to the lower leg member for applying torque to the knee joint to rotate the lower leg member with respect to the thigh member. The apparatus also includes at least one sensor having at least one output from which a position of the knee joint with respect to an ankle joint can be determined while the wearer of the apparatus is in a seated position, and a controller that determines when the knee joint is moved to position that is forward of the ankle joint based on the least one output of the at least one sensor. In response to that determination, the controller controls the rotary motor so as to modulate impedance, position, or torque of the knee joint to help raise the person from the seated position to a standing position.

Another aspect of the invention relates to a method of controlling a knee orthosis or prosthesis having at least one actuator. This method includes the steps of detecting the position of the person's knee with respect to the person's ankle while the person is in a seated position, and determining when the knee is moved to position that is forward of the ankle based on a result of the detecting step, and generating an output indicative thereof. In response to the output, at least one actuator of the knee orthosis or prosthesis is actuated to help raise the person from the seated position to a standing position.

BRIEF DESCRIPTION OF THE DRAWINGS

FIG. 1A is a schematic illustration of the different phases of a wearer's gait cycle over level ground.

FIG. 10D is a schematic illustration of the mechanical impedance relation that governs the impedance control performed in FIG. 10A.

FIG. 10E is a schematic illustration of the impedance and reflex relation that governs the impedance and reflex control performed in FIG. 10B.

FIGS. 11B-11D are schematic illustrations of the components of an ankle prosthesis showing the force and moment relationships among the components necessary to determine the ground reaction forces and the zero moment pivot.

FIG. 17D is an illustration of the free-body diagram for the passive parallel elastic element of FIG. 17C, according to an illustrative embodiment of the invention.

FIG. 17G is an illustration of a method for computing the in-plane moment vector and axial force using a circular array of displacement sensors on a printed circuit assembly, according to an illustrative embodiment of the invention.

FIGS. 29A-D depicts a stand-up sequence for a healthy person.

FIGS. 30A-D depicts the problems in implementing the same stand-up sequence for impaired patients.

FIGS. 31A-D depicts how a knee apparatus is used to assist the stand-up sequence for impaired patients.

DETAILED DESCRIPTION OF THE PREFERRED EMBODIMENTS

The inventors have recognized that during the course of an ordinary day, a person's lower limbs are used to perform and adapt to many different activities in addition to ordinary walking, such as ascending and descending stairs, and walking on inclined ramps. The ankle-foot components require the most power and must exhibit the most terrain-adaptive behavior because these are in the most direct contact with the underlying terrain. The inventors have further recognized that the performance of AFPs can be dramatically improved by dynamically optimizing the mechanical characteristics of the device in different ways and dynamically controlling the device in different ways for each of those activities.

For example, when a person is walking on flat ground, it is better to control the angle of the foot so that the heel is lower than the toe when the foot touches down on the ground. However, when a person is ascending stairs, it is better to control the angle of the foot so that the toe is lower than the heel when the foot touches down on the next step.

This application describes various embodiments of AFPs that perform appropriately in each of these different situations by detecting the terrain that is being traversed, and automatically adapting to the detected terrain. In some embodiments, the ability to control the AFP for each of these situations builds upon five basic capabilities: (1) determining the activity being performed; (2) dynamically controlling the characteristics of the AFP based on the activity that is being performed; (3) dynamically driving the AFP based on the activity that is being performed; (4) determining terrain texture irregularities (e.g., how sticky is the terrain, how slippery is the terrain, is the terrain coarse or smooth, does the terrain have any obstructions, such as rocks) and responding to these with appropriate traction control and (5) a mechanical design of the AFP that can respond to the dynamic control and dynamic drive.

Figure 6A:
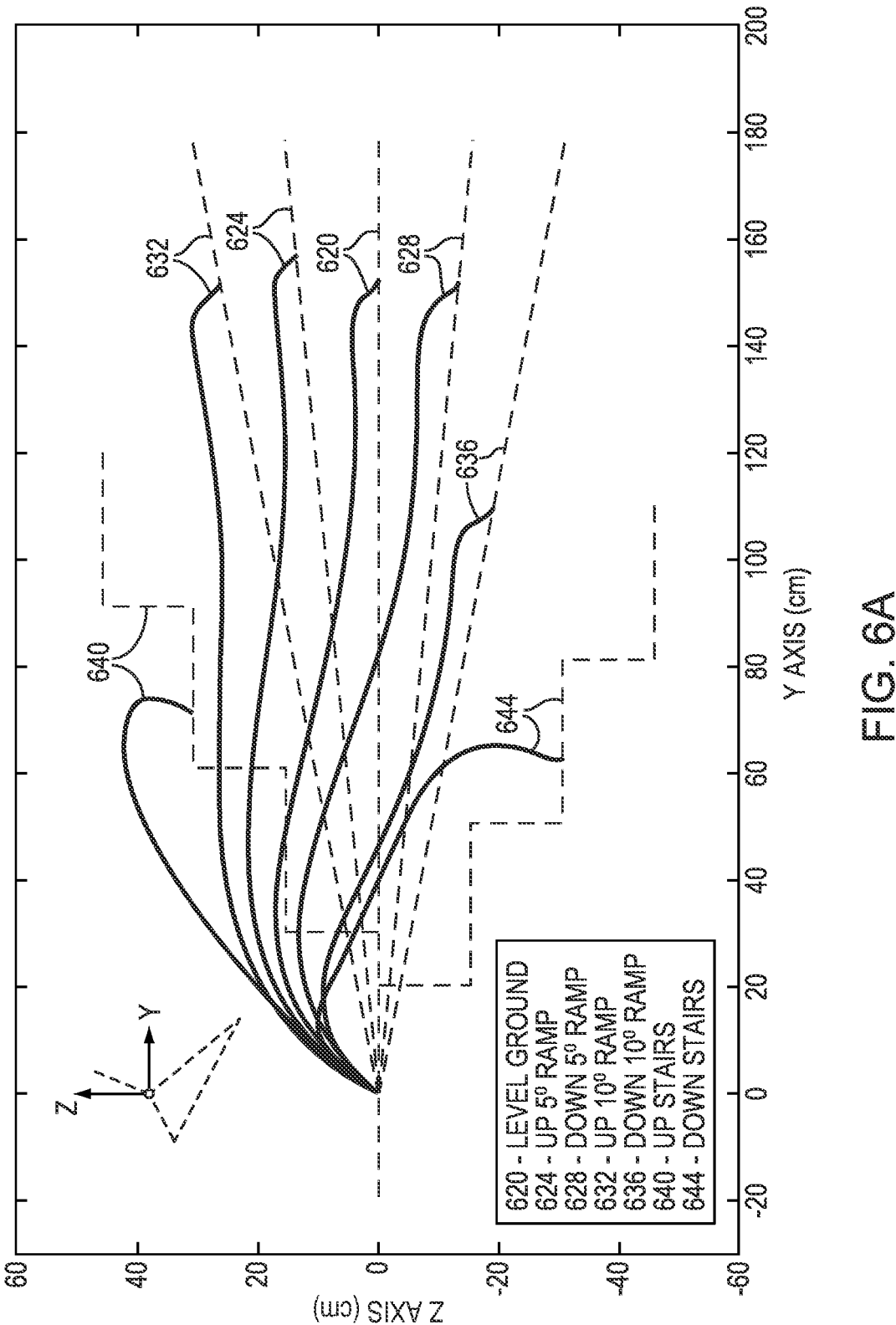
FIG. 6A illustrates the inertial measurement unit-computed ankle joint pivot trajectories in different ambulation contexts.

The inventors have determined that an exemplary way to figure out what activity is being performed is to track the trajectory of a spot (typically at the virtual center of rotation of the ankle joint) on the lower leg (or shank) between the ankle joint and knee joint. FIG. 6A shows the shank trajectories that correspond to five different activities, with additional ramp trajectories to distinguish between steep and shallow ramps. The system can use this information to figure out what activity is being performed by mapping the tracked trajectory onto a set of activities.

By looking at the trajectory of the lower leg (shank) it is possible to distinguish between flat terrain, ascending or descending stairs, or ascending or descending ramps. For example, when the system recognizes a trajectory it would switch into an appropriate mode, and dynamically control (drive) the AFP as previously established for the mode. Where a trajectory does not fall neatly within a classification, the AFP controller would optimize the response to minimize an objective function in a stochastic control sense or would apply fuzzy logic or ad hoc controls based upon the likelihood the terrain falls into a classification.

One suitable way to track the trajectory of the shank is by mounting an inertial measurement unit (IMU) at the forward face at the top of the lower leg member (shank), and processing the signals that are output by the IMU. A suitable way to distinguish the various trajectories is to monitor the velocity of the ankle joint angle of attack. These topics are described in greater detail below.

In addition to dynamically optimizing the mechanical characteristics and dynamically controlling the device in different ways for each of the different activities, the inventors have recognized that the performance of the device can be further improved by fine-tuning the characteristics and control of the AFP based on various parameters.

For example, when a person is walking slowly (e.g., at a rate of less than 0.9 meters per second), performance can be improved by increasing the impedance of the ankle joint with respect to the impedance used for normal walking. Or when a person is walking quickly (e.g., at a rate of 1.7 meters per second), performance can be improved by decreasing the impedance of the ankle joint with to the impedance used for normal walking.

In addition, when the controller determines that the ankle joint is not responding as we would expect it to when traversing normal terrain, the controller can take into account (and modify the output of the controller) that there may be features, texture or irregularities in the terrain (e.g., how sticky is the terrain, how slippery is the terrain, is the terrain coarse or smooth, does the terrain have any obstructions, such as rocks).

Each of the five capabilities identified above (i.e., figuring out what activity is being performed; figuring out whether there are features, texture or irregularities of the terrain; dynamically controlling the characteristics of the AFP; dynamically driving the AFP; and the mechanical design of the AFP) is described in greater detail below.

Determining Activity Being Performed

Inertial Pose and Trajectory Estimation

Figure 1B:
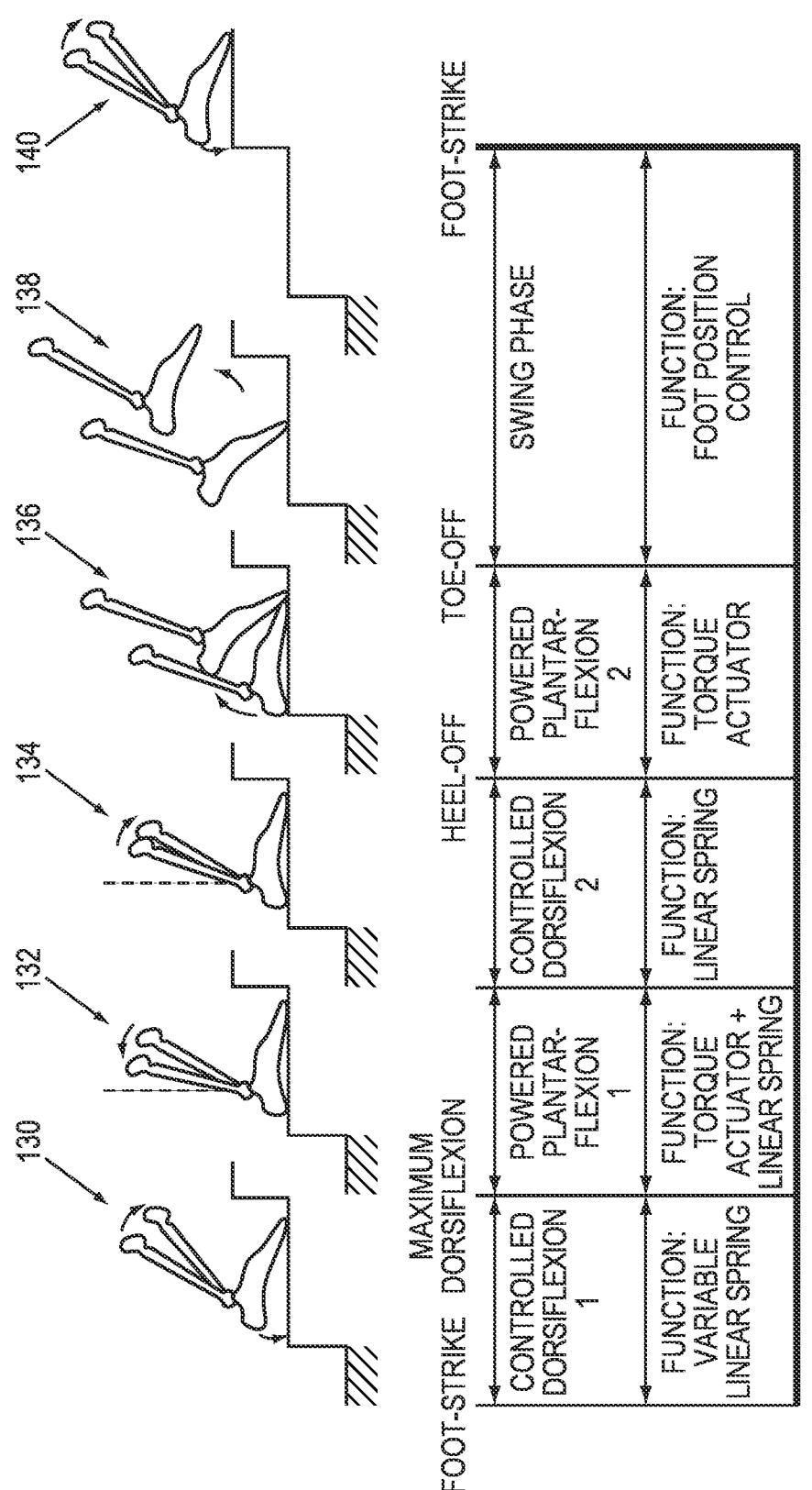
FIG. 1B is a schematic illustration of the different phases of a wearer's gait cycle ascending stairs.
Figure 1C:
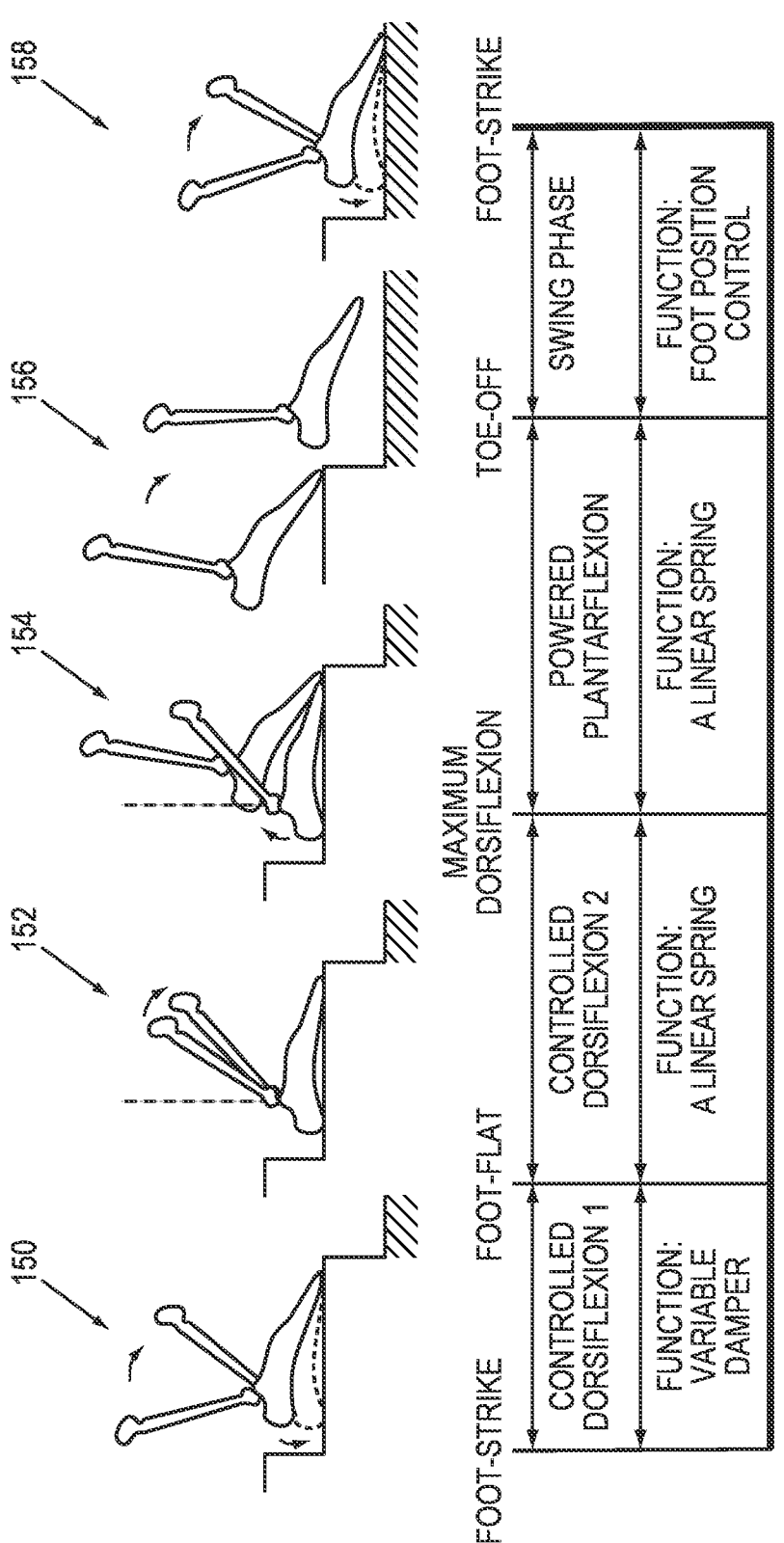
FIG. 1C is a schematic illustration of the different phases of a wearer's gait cycle descending stairs.
Figure 2A:
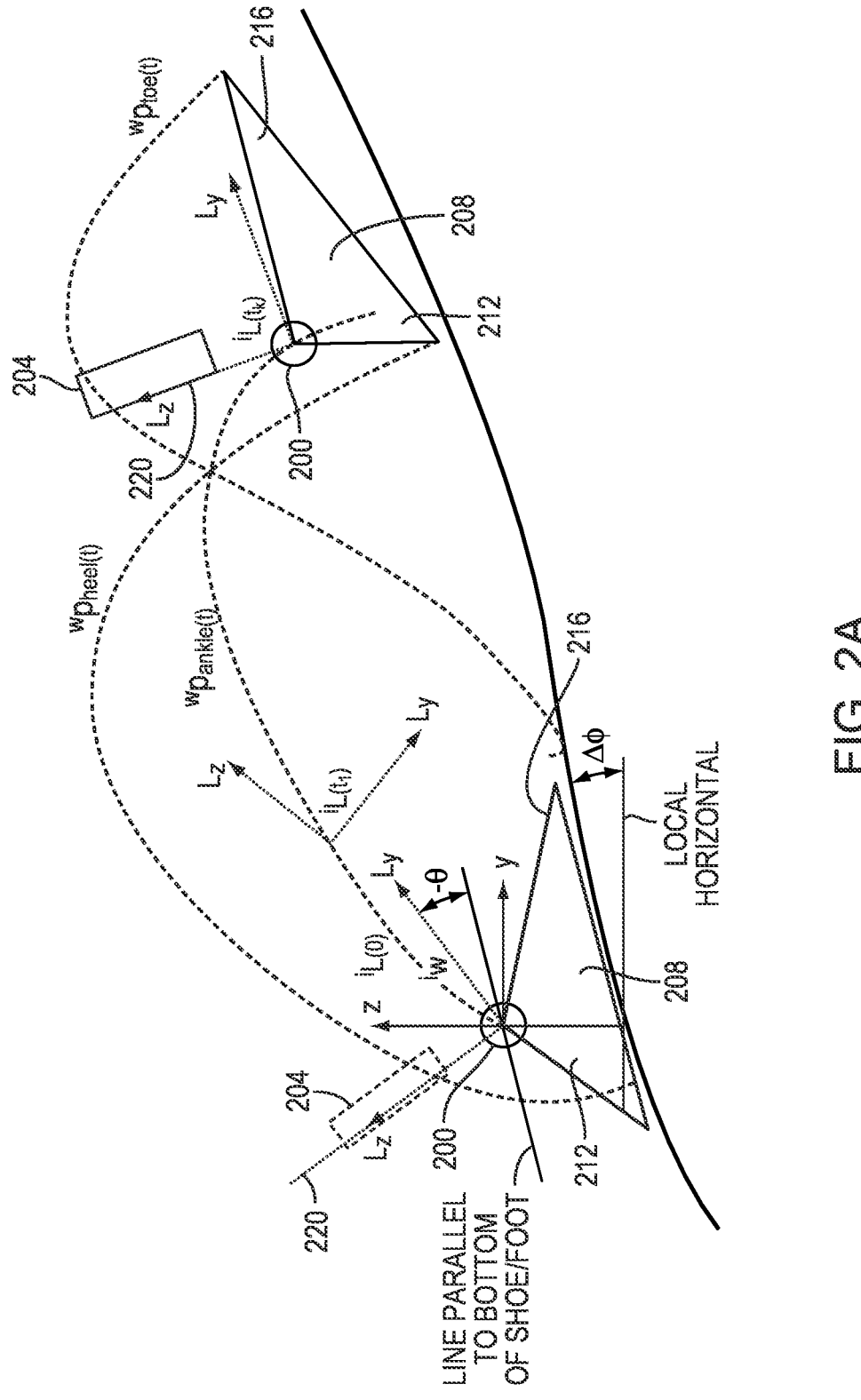
FIG. 2A is a schematic illustration of a method for determining ankle joint, heel and toe trajectories of a prosthetic, orthotic, or exoskeleton apparatus, according to an illustrative embodiment of the invention.

FIG. 2 is a schematic illustration of a method for determining ankle joint 200, heel 212 and toe 216 trajectories of a prosthetic, orthotic, or exoskeleton apparatus (for example, apparatus 1700 of FIG. 17A) based on the inertial pose of a lower leg member 220 coupled to the ankle joint 200, and the angle between the lower leg member 220 and foot member 208. Pose is the position and orientation of a coordinate system. The apparatus 1700 includes an inertial measurement unit 204 coupled to the lower leg member 220. The inertial measurement unit 204 includes a three-axis rate gyro for measuring angular rate and a three-axis accelerometer for measuring acceleration. Placing the inertial measurement unit on the lower leg member 220 collocates the measurement of angular rate and acceleration for all three axes of the lower leg member 220. The inertial measurement unit 204 provides a six-degree-of-freedom estimate of the lower leg member 220 pose, inertial (world frame referenced) orientation and ankle-joint 200 (center of rotation of the ankle-foot) location.

In some embodiments, the lower leg member 220 pose is used to compute the instantaneous location of the knee joint. By using knowledge of the ankle joint 200 angle ($\theta$) the instantaneous pose of the bottom of the foot 208 can be computed, including location of the heel. 212 and toe 216. This information in turn can be used when the foot member 208 is flat to measure the terrain angle in the plane defined by the rotational axis of the ankle joint/foot member. Mounting the inertial measurement unit 204 on the lower leg member 220 has advantages over other potential locations. Unlike if it were mounted on the foot member 208, the lower leg member 220 mounting protects against physical abuse and keeps it away from water exposure. Further, it eliminates the cable tether that would otherwise be needed if it were on the foot member 208—thereby ensuring mechanical and electrical integrity. Finally, the lower leg member 220 is centrally located within the kinematic chain of the hybrid system (referring to FIG. 15), facilitating the computation of the thigh and torso pose with a minimum of additional sensors.

The inertial measurement unit 204 is used to calculate the orientation, $^w_{ankle}O$, position, $^w_{ankle}P$, and velocity, $^w_{ankle}V$, of the lower-extremity prosthetic apparatus in a ground-referenced world frame. $^w_{ankle}O$ may be represented by a quaternion or by a 3×3 matrix of unit vectors that define the orientation of the x, y and z axes of the ankle joint in relation to the world frame. The ankle joint 200 coordinate frame is defined to be positioned at the center of the ankle joint axis of rotation with its orientation tied to the lower leg member 220. From this central point, the position, velocity and acceleration can be computed. For points of interest in, for example, the foot (e.g., the heel 212 or toe 216), a foot member-to-ankle joint orientation transformation, $^{ankle}_{foot}O$ ($\theta$) is used to derive the position using the following relation:

$$^w_{point-of-interest}P = {}^w_{ankle}P + {}^w_{ankle}O(\gamma)^{ankle}_{foot}O(\theta)\left({}^{foot}r_{point-of-interest}\right)$$ EQN. 1 where $$^{ankle}_{foot}O(\gamma) = \begin{bmatrix} 1 & 0 & 0 \\ 0 & \cos(\gamma) & -\sin(\gamma) \\ 0 & \sin(\gamma) & \cos(\gamma) \end{bmatrix}$$ EQN. 2 where $\gamma$ is the inertial lower leg member angle, and $$^{ankle}_{foot}O(\theta) = \begin{bmatrix} 1 & 0 & 0 \\ 0 & \cos(\theta) & -\sin(\theta) \\ 0 & \sin(\theta) & \cos(\theta) \end{bmatrix}$$ EQN. 3 where $\theta$ is the ankle joint angle.

Figure 17A:
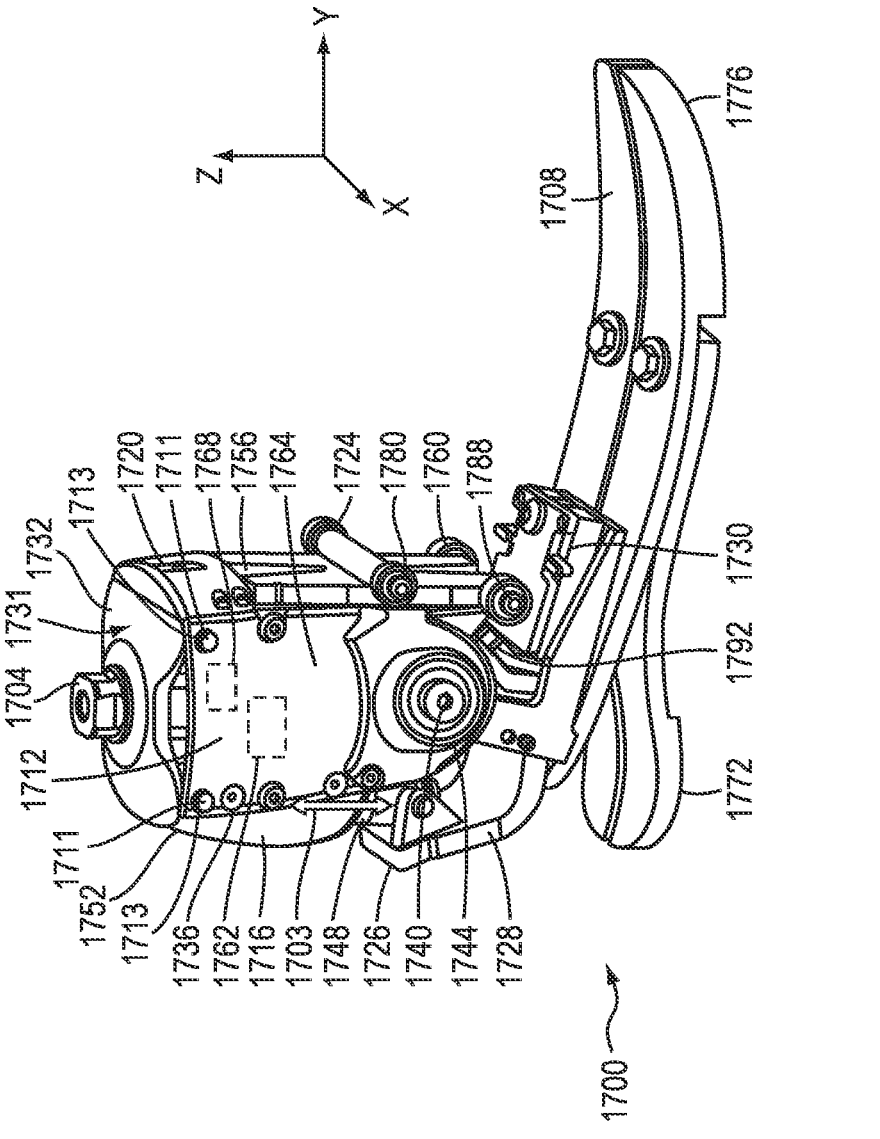
FIG. 17A is an illustration of a lower-extremity prosthetic apparatus, according to an illustrative embodiment of the invention.

In this embodiment, the inertial measurement unit 204, including the three-axis accelerometer and three-axis rate gyro, is located on the forward face at the top of the lower leg member 220 (as shown in, for example, FIG. 17A). It is necessary to remove the effect of scale, drift and cross-coupling on the world-frame orientation, velocity and position estimates introduced by numerical integrations of the accelerometer and rate gyro signals

Zero-Velocity Update

Inertial navigation systems typically employ a zero-velocity update (ZVUP) periodically by averaging over an extended period of time, usually seconds to minutes. This placement of the inertial measurement unit is almost never stationary in the lower-extremity prosthetic apparatus. However, the bottom of the foot is the only stationary location, and then only during the controlled dorsiflexion state of the gait cycle. An exemplary zero-velocity update method, which is not impacted by this limitation, for use with various embodiments of the invention is described further below.

To solve this problem, orientation, velocity and position integration of ankle joint is performed. After digitizing the inertial measurement unit acceleration, $^{IMU}a$, the ankle joint acceleration ($^{IMU}a_{ankle}$) is derived with the following rigid body dynamic equation:

$$^{IMU}a_{ankle} = {}^{IMU}a + {}^{IMU}\vec{\omega} \times {}^{IMU}\vec{\omega} \times_{ankle}{}^{IMU}\vec{r} + \vec{\omega} \times_{ankle}{}^{IMU}\vec{r}$$ EQN. 4 where IMU$_{\vec{\omega}}$ and IMU$_{\vec{\alpha}}$ are the vectors of angular rate and angular acceleration, respectively, in the inertial measurement unit frame and X denotes the cross-product.

The relationship is solved $^w_{ankle}O = {}^w_{IMU}O$ similarly as in EQNS. 1-3 using standard strapdown inertial measurement unit integration methods, in accordance with the following relationships known to one skilled in the art:

$$^w_{ankle}\dot{\hat{\Phi}} = {}^w\Omega({}^w\hat{\omega})^w_{ankle}\hat{\Phi}$$ EQN. 5

$$^w\hat{v}_{ankle} = {}^w\hat{a}_{ankle} - [0, 0, g]^T$$ EQN. 6

$$^w\dot{p}_{ankle} = {}^w\hat{v}_{ankle}$$ EQN. 7

$$^w_{foot}\hat{\Phi} = {}^w_{ankle}\hat{\Phi}^{ankle}_{foot}\hat{\Phi} = {}^w_{ankle}\hat{\Phi} \text{ Rotation}_x (\hat{\Theta})$$ EQN. 8

$$^w\hat{v}_{heel} = {}^w\hat{v}_{ankle} + {}^w\hat{\Omega}\left({}^w_{ankle}\hat{\Phi}\left[\hat{\Theta} \ \ 0 \ \ 0\right]^T\right)^w r_{heel-ankle}$$ EQN. 9

$$^w\hat{v}_{toe} = {}^w\hat{v}_{ankle} + {}^w\hat{\Omega}\left({}^w_{ankle}\hat{\Phi}\left[\hat{\Theta} \ \ 0 \ \ 0\right]^T\right)^w r_{toe-ankle}$$ EQN. 10

$$^w\hat{p}_{heel} = {}^w\hat{p}_{ankle} + {}^w r_{heel-ankle}$$ EQN. 11

$$^w\hat{p}_{toe} = {}^w\hat{p}_{ankle} + {}^w r_{toe-ankle}$$ EQN. 12

$$^w r_{heel-ankle} = {}^w_{foot}\hat{\Phi}^{foot}(r_{heel} - r_{ankle})$$ EQN. 13

$$^w r_{toe-ankle} = {}^w_{foot}\hat{\Phi}^{foot}(r_{toe} - r_{ankle})$$ EQN. 14

In equations 5-14 above, the matrix, $\Phi$, will be used interchangeably with the orientation matrix, $^w_{IMU}O$.

The world frame-referenced ankle joint velocity and position are then derived at a point in time after the time of the previous zero-velocity update ($i^{th}$ zero-velocity update) based on the following:

$$^w v_{ankle}(t) = \int_{ZVUP(i)}^t ({}^w_{IMU}O)IMU_{a_{ankle}}dt$$ EQN. 15

$$^w p_{ankle}(t) = \int_{ZVUP(i)}^t {}^w v_{ankle}dt$$ EQN. 16 where $^w p_{ankle}$(t=ZVUP(i)) is reset to zero for all i.

Figure 2B:
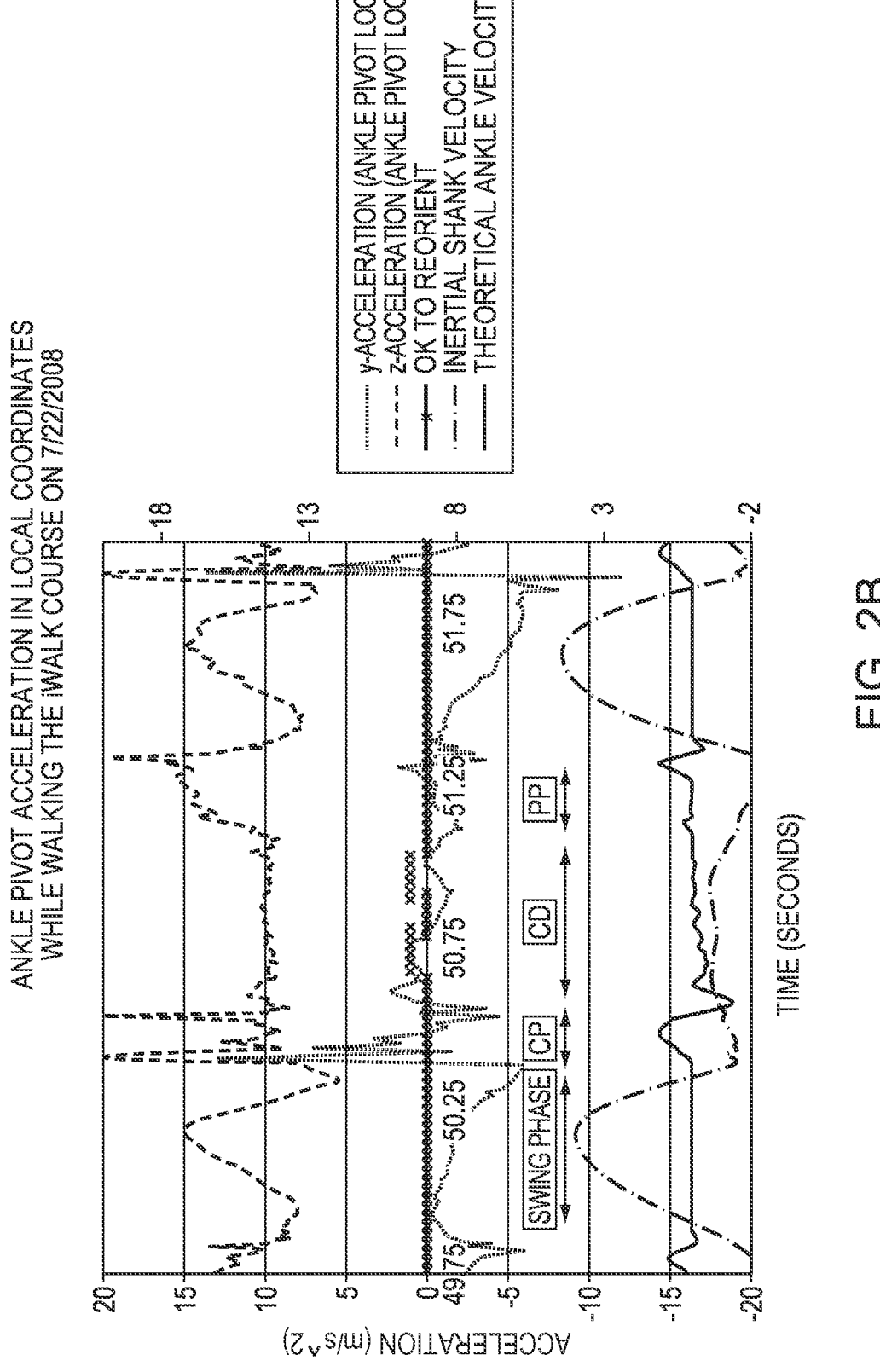
FIG. 2B is a plot of experimental data showing ankle joint acceleration during walking.

Through experimentation, using logs of inertial measurement unit data acquired from an exemplary lower-extremity prosthetic apparatus (e.g., lower-extremity prosthetic apparatus 1700 of FIG. 17A), we determined that the inertial measurement unit-referenced accelerations were sufficiently quiet early (see FIG. 2B at approximately 50.75 seconds and 50.9 seconds when the z-acceleration is equal to about 1 g (approximately 9.8 m/s²) in the controlled dorsiflexion state and the variance of the z-acceleration is less than a predetermined value (<0.005 g²) indicating a period in time where the lower leg member 220 is rotating about a stationary ankle joint 200. In another embodiment of this technique, a suitable quiet period can be detected on some part of the foot. Knowledge of the acceleration, angular rate and angular acceleration of the ankle joint can be combined with the knowledge of the sensed ankle angle (angle between the foot member and the lower leg member), angle rate and angle acceleration to calculate the acceleration of any point on the foot. Some point on the bottom of the foot can often be used to perform a zero velocity update on successive gait cycles. Once this velocity is known, the velocity of the ankle joint can be computed a posteriori. This velocity (rather than zero) can be used as a reference from which the zero velocity update can be performed.

In the lower-extremity prosthetic apparatus, a quiet period nearly always exists in the Controlled Dorsiflexion state, so a zero-velocity update may be performed for every step that the wearer takes. During each zero-velocity update, the velocity error contribution from each of three terms are preferably evaluated—the tip, $\delta\theta_x$ of the world frame z-axis about the x-axis (the vector aligned with the ankle joint axis of rotation during the zero-velocity update on the previous step); the tilt, $\delta\theta_y$ of the world frame z-axis about the y-axis (a vector defined as the cross-product of the world-frame vertical (opposing the gravity vector) and the world frame x-axis); and the inertial measurement unit scaling along the vertical axis, $\delta g$. The values of these terms are used to correct the computed pose, inertial orientation and previous computed poses and inertial orientations of the different components of the apparatus (e.g., the lower leg member 1712 of FIG. 17A).

While performing the orientation, velocity and position integration, a sensitivity matrix, M(t) is calculated that relates the velocity error that would be introduced by the vector of errors, $\alpha=[\delta\theta_x\delta\theta_y\delta g]^T$. M(t) based on the following relationship:

$$M(t) = \frac{\partial}{\partial\alpha}\left({}_{IMU}^{w}O^{IMU}a_{ankle}\right) \qquad \text{EQN. 17}$$

in which, M(t) is integrated numerically to generate the overall terminal velocity sensitivity, M*, $$M^* = \int_{ZVUP_{i-1}}^{ZVUP_i}M(t)dt \qquad \text{EQN. 18}$$

In some embodiments, the vector of errors is expanded to include accelerometer bias offsets if these errors are significant, thereby increasing the number of columns in M(t) and in M*. In this case, $M^{*-1}$ takes the form of the Penrose pseudo-inverse or, by an optimal innovations gain, K*.

K* can be computed using standard optimal linear filtering methods. To one skilled in the art, other terms can be included or used without loss of generality.

At the zero-velocity update for step i, the value of $\alpha$ that would have generated the estimated non-zero ankle joint velocity, ${}^{w}v_{ankle}(ZVUP_i)$, is determined based on:

$$\alpha=M^{*-1w}v_{ankle}(ZVUP_i) \qquad \text{EQN. 19}$$

where $\alpha$ is the innovations correction vector. Since the non-zero velocity results in part from noise in the accelerometers and angular rate measurements, not all of the innovations correction ($\alpha$) is applied. Instead, the correction is scaled by a filtering constant (fraction), k, depending on the magnitude of the noise. At this point, the new orientation matrix (ankle$^w$O) and gravity magnitude (g) are determined based on:

$$_{ankle}{}^{w}O(ZVUP_i{}^+)=O_x(-k\alpha(1))O_y(-k\alpha(2))_{ankle}{}^{w}O \\ (ZVUP_i{}^-) \qquad \text{EQN. } \mathbf{20}$$

$$g(ZVUP^+)=g(ZVUP^-)-k\alpha(3) \qquad \text{EQN. 21}$$

where $O_x$(tip) and $O_y$(tilt) denote incremental rotations of tip and tilt about the x and y axes respectively, and ZVU $P_i^+$ and ZVU $P_i^-$ denote the times after and before the ZVUP, respectively.

It is possible to extend the zero velocity update to estimate accelerometer and rate gyro bias offsets using linear estimators. Consistent angular alignment errors (e.g., about a given axis) could be used to estimate the rate gyro bias about that axis. In one embodiment, this is performed by creating linear stochastic models of accelerometer and rate gyro bias and using the zero-velocity update prediction residuals as inputs to the linear filter applied to those models.

The above method is a method for continually updating the orientation and apparent gravity magnitude. An initialization procedure is used in this embodiment when the lower-extremity prosthetic apparatus is first powered on. In this method, the wearer will, when requested by the apparatus (e.g., by a vibration code transmitted by the apparatus or an alternative user interface), take one step forward and stop, then take one step back to the original position. In this process, the steps will be taken on the affected leg (for bilateral amputees, this calibration will be executed in a serial fashion as selected by the amputee). The calibration will invoke two ZVUP's-one to initialize the orientation and gravity magnitude, the second to check the result. This will ensure integrity of the inertial measurement unit signals, processing and controller communication.

The above process accomplishes an initialization of the inertial orientation. It is, however, of general interest to accomplish a full calibration of the IMU, to account for the vector (c) of error sources a vector that includes bias offset, scale and cross-sensitivity embodied within the accelerometer and gyro signals. In manufacturing, a robot or other six degree-of-freedom machine can carry the IMU and apply reference trajectories in succession as a means of measuring the effect of these error sources. The sensitivity matrix (M($\varepsilon$)) of the sensed reference trajectories to each of the error sources can be easily computed by those skilled in the art. By measuring the sensed deviations from a rich set of reference trajectories typically the deviation of the end-point of each trajectory segment the vector (c) can be estimated using regression or other linear estimation methods-provided that the set of reference trajectories is rich enough to excite the influence of each error source. The inventors have found that reference trajectories that include closed paths like polygons and circles in three orthogonal planes are sufficient to calibrate the full vector of error sources. Such reference trajectories can also be conducted by the wearer to recalibrate key elements of the vector (accelerometer bias, scale and cross-sensitivity) by, for example, walking in a sequence of closed patterns on a horizontal plane and by rotating in sequence about a vertical axis.

Figure 16:
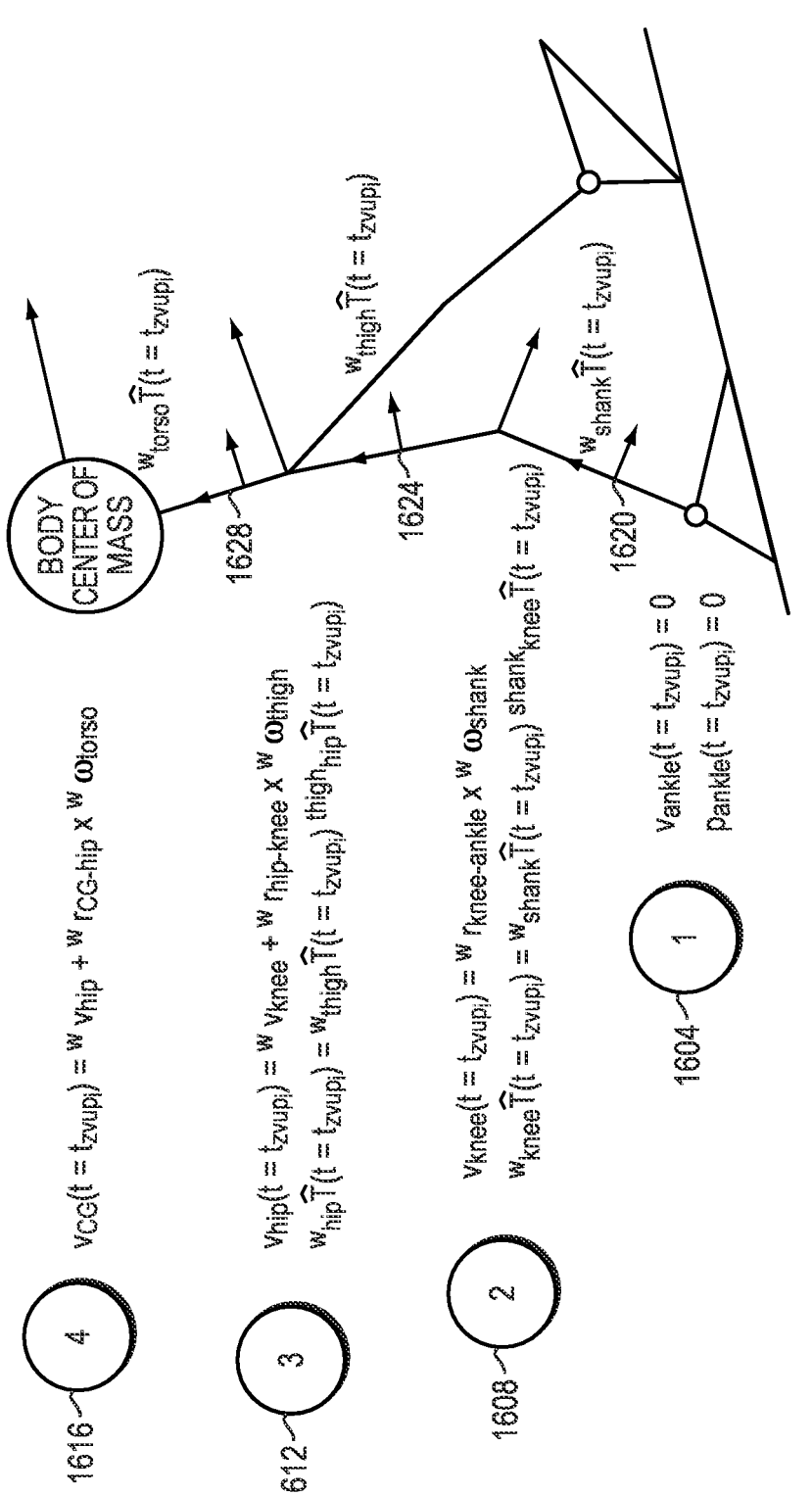
FIG. 16 illustrates a method of pose reconstruction for torso pose, thigh pose and torso/body center-of-mass pose, according to an illustrative embodiment of the invention.

In some embodiments of the invention, these principles of the method are similarly applied to correcting or minimizing the effect of accelerometer and rate gyro drift error associated. with accelerometers and rate gyros located on, for example, the thigh member and/or torso of a wearer in which the prosthetic, orthotic, or exoskeleton apparatus treats or augments performance of these portions of a wearer's body. In one embodiment, the method includes determining offset values for an accelerometer signal and rate gyro signal output by an accelerometer and rate gyro coupled to a thigh member of the prosthesis or orthosis when the ankle joint is substantially stationary during a walking cycle of the prosthesis or orthosis. The method also can include measuring the angle of the lower leg member relative to the thigh member. In another embodiment, the method also includes determining offset values for an accelerometer signal and rate gyro signal output by an accelerometer and rate gyro coupled to a wearer's torso when the ankle joint is substantially stationary during a walking cycle of the prosthesis or orthosis. The method also can include measuring the angle of the thigh member relative to the wearer's torso. The methods can therefore be extended to the thigh member and/or torso of a wearer by performing these measurements and relying on the linkage constraint relationships and related methods, as shown in FIG. 16. At the time of the zero velocity update, the linkage constraints enable propagation of the joint velocity references backwards from the ground-referenced zero velocity of the lowest link in the kinematic chain (e.g., the linkage that defines the hybrid human-robot system). These velocity references can be used as the input to the pose realignment and gravity compensation as defined above.

Exemplary Ankle Joint Trajectories and Terrain Context Discrimination

Figure 3:
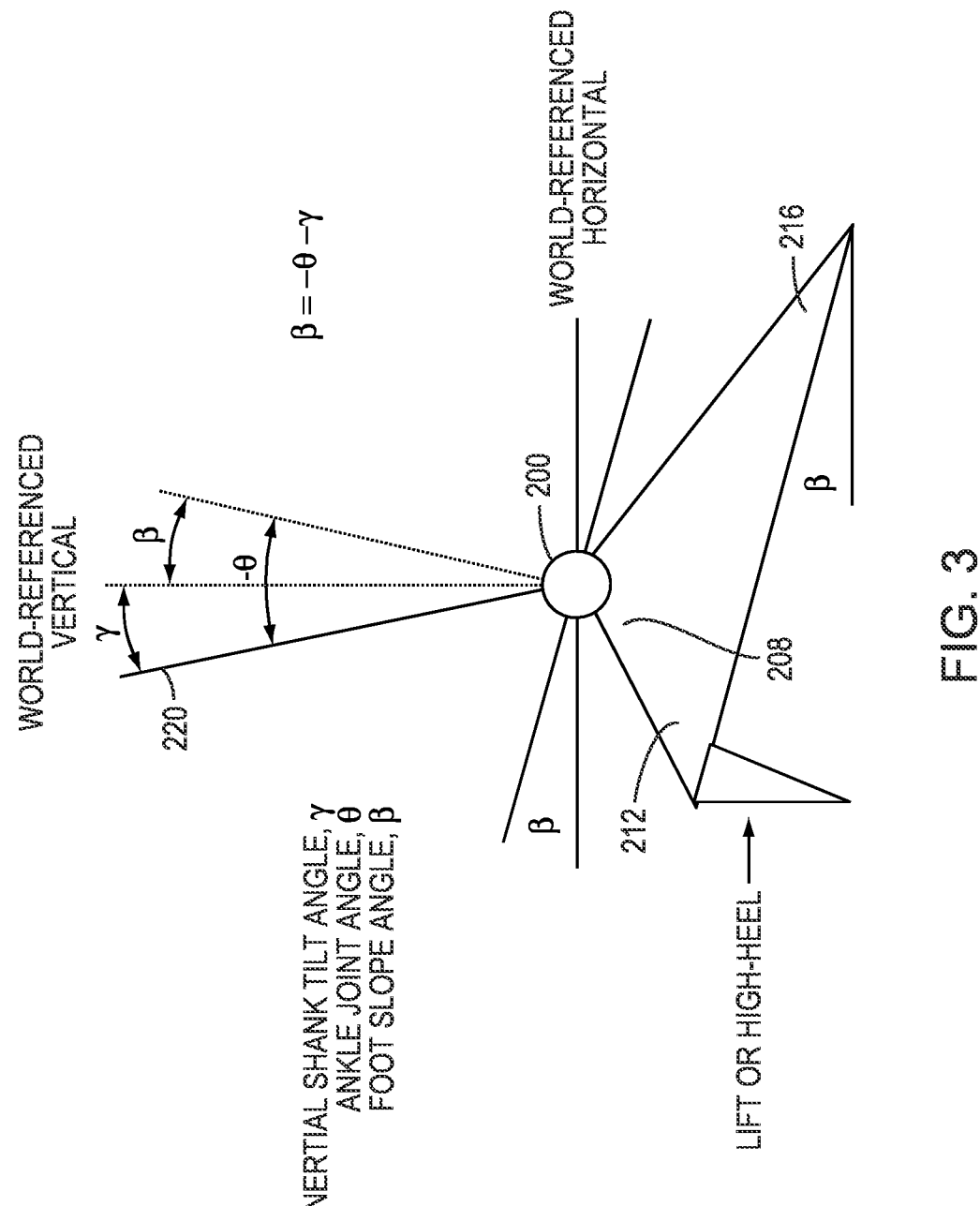
FIG. 3 is a schematic illustration of a method for determining foot slope (heel height), according to an illustrative embodiment of the invention.

Once the inertial measurement unit offsets have been calculated and corrected (zeroed), the foot-slope ($\beta$) (alternatively referred to as heel height) is determined as illustrated in, for example, FIG. 3. From the illustration it is easy to see that when the wearer is standing with her foot flat on the ground that $\beta = -(\theta + \gamma)$. By averaging over a period of about a tenth of a second an accurate estimate of $\beta$ can be determined. Thereafter, the orientation component of the transformation that defines the foot to ankle coordinate system, $_{foot}^{ankle}O$, is computed based on the following:

$$_{foot}^{ankle}O(\beta, \gamma) = \begin{bmatrix} 1 & 0 & 0 \\ 0 & \cos(\beta+\gamma) & -\sin(\beta+\gamma) \\ 0 & \sin(\beta+\gamma) & \cos(\beta+\gamma) \end{bmatrix} \qquad \text{EQN. 22}$$

As before, the translational component of this transform will remain zero.

Once the foot-slope is defined, it is then necessary to determine the heel 212 and toe 216 coordinates in the foot coordinate system. In one exemplary method for determining this, $^{foot}\hat{p}_{heel}$ and $^{foot}\vec{p}_{toe}$ are defined as the vector coordinates of the heel and toe in the new foot coordinate system. Because the rotational contribution of $\beta$ has already been incorporated, the z-component of these vectors is the same. It can be assumed that the x-component of these vectors are both zero. So these vectors take the form:

$$^{foot}\vec{p}_{heel} = \begin{bmatrix} 0 \\ y_{heel} \\ z_0 \end{bmatrix} \qquad \text{EQN. 23}$$

$$^{foot}\vec{p}_{toe} = \begin{bmatrix} 0 \\ y_{toe} \\ z_0 \end{bmatrix} \qquad \text{EQN. 24}$$

where $z_0$ defines the z-coordinate of the bottom of the foot (shoe).

Figure 4:
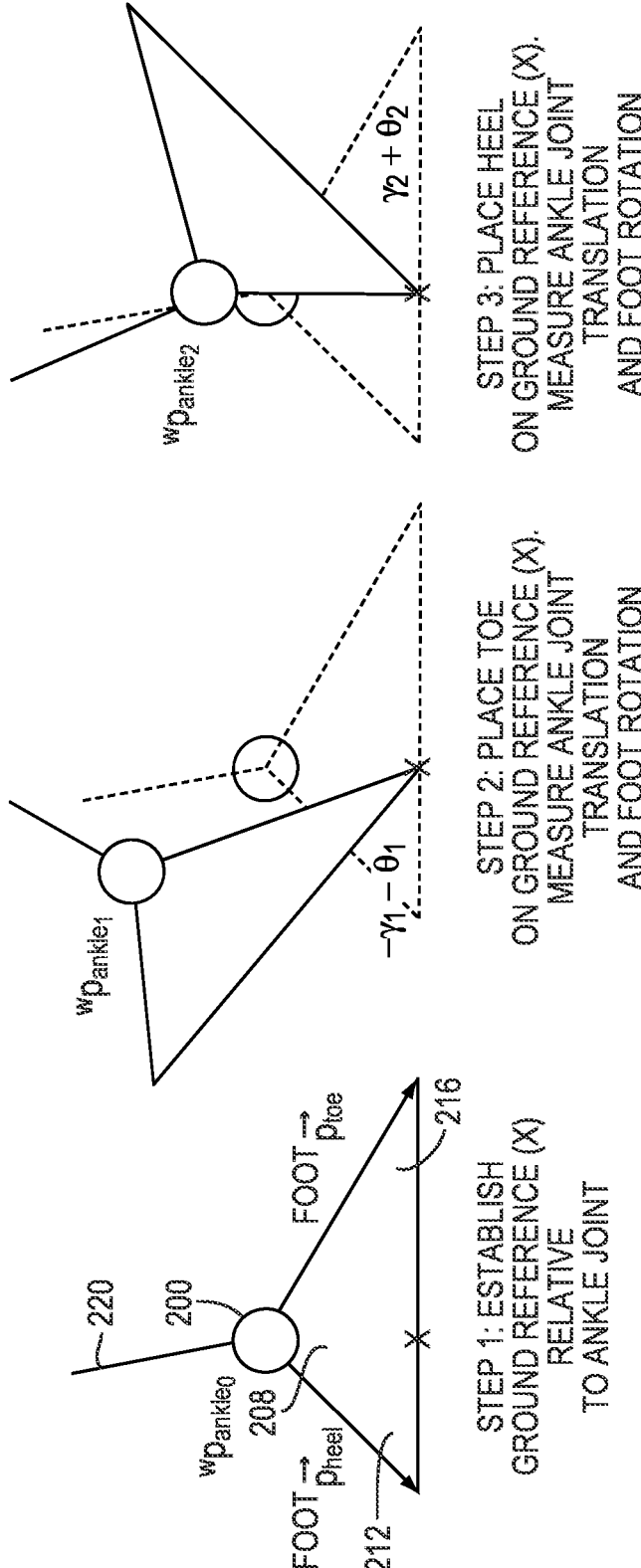
FIG. 4 is a schematic illustration of a method for determining the coordinates of the heel and toe in relation to the ankle joint in the foot frame of reference, according to an illustrative embodiment of the invention.

FIG. 4 is a schematic illustration of a method for determining the coordinates of the heel 212 and toe 216 in relation to the ankle joint 200 in the foot frame of reference, according to an illustrative embodiment of the invention. In the first step of the foot calibration method defined in FIG. 4, they-coordinate of the ankle joint 200 is aligned to a ground reference (e.g., seam in the pavement, a prominent feature on a rug or on a linoleum surface). We arbitrarily define this ground reference to be the origin of the world coordinate system. In mathematical notation, this alignment takes the form:

$$^{world}p_{ankle_0} = \begin{bmatrix} 0 \\ 0 \\ -z_0 \end{bmatrix} \qquad \text{EQN. 25}$$

where $^{world}p_{ankle_0}$ is the starting position for the moves that take place in steps 2 and 3. In the second step, the toe 216 is placed onto the ground reference.

In mathematical notation, this alignment takes the form:

$$\begin{bmatrix} 0 \\ 0 \\ 0 \end{bmatrix} = {}^{world}p\,ankle_1 + O(\gamma)O(\theta+\beta)\begin{bmatrix} 0 \\ y_{toe} \\ z_0 \end{bmatrix} \qquad \text{EQN. 26}$$

or $$^{foot}\vec{p}_{toe} = \begin{bmatrix} 0 \\ y_{toe} \\ z_0 \end{bmatrix} = -O^{-1}(\gamma)O^{-i}(\theta+\beta)^{world}p_{ankle_1} \qquad \text{EQN. 27}$$

A similar relationship is determined during the alignment in step 3. When the equations above are solved independently, two different estimates of $z_0$ are obtained. By combining the two constraint equations into one, a least-squares estimate of $y_{heel}$, $y_{toe}$ and $z_0$ can be obtained.

The heel 212 and toe 216 calibration method described above involves a series of steps that would be used the first time a new pair of feet/shoes are worn. Such a calibration could be performed at, for example, the prosthetist office.

Figure 5:
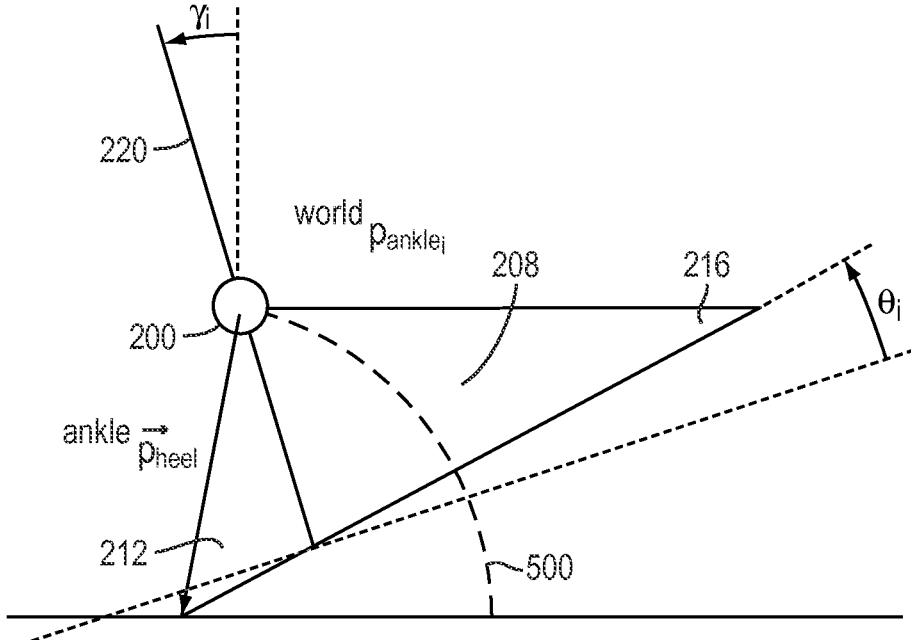
FIG. 5 is a schematic illustration of a method for estimating a heel vector, according to an illustrative embodiment of the invention.

In another exemplary method, the heel and toe vectors are calculated on-the-fly. As shown in FIG. 5, the ankle joint 200 traces an arc 500 in the early stance phase between foot-strike and foot-flat. The radius and orientation (midpoint angle) of the arc 500 fully determine the heel and toe vectors. Mathematically, this is described as a series of ankle positions ($^{world}p_{ankle_i}$) that are recorded during early stance. Two ankle position measurements are needed, corresponding to two statistically distinct lower leg member 220 ($\gamma_i$) and ankle joint 200 angle ($\theta_i$) positions, yielding:

$$^{world}p_{heel_1} = {}^{world}p_{ankle_1} + O(\gamma_1)O(\theta_1)^{foot}\vec{p}_{heel} \qquad \text{EQN. 28}$$

$$^{world}p_{heel_2} = {}^{world}p_{ankle_2} + O(\gamma_2)O(\theta_2)^{foot}\vec{p}_{heel} \qquad \text{EQN. 29}$$

Then, by differencing the equations, the vector solution becomes:

$$^{foot}\vec{p}_{heel} = (O(\gamma_2)O(\theta_2) - O(\gamma_1)O(\theta_1))^{-1}(^{world}p_{ankle_2} - {}^{world}p_{ankle_1}) \qquad \text{EQN. 30}$$

The solution requires that $(O(\gamma_2)O(\theta_2) - O(\gamma_1)O(\theta_1))$ is invertible. And from an optimal linear filtering standpoint, this "gain matrix" must be large enough so as to yield a statistically significant result.

Considering the fact that the lower-extremity prosthetic apparatus undergoes significant vibration during the early stance phase, the equations above can be extended to N sets of ankle joint position/angle measurements. The resulting N−1 equations can be solved using least-squares techniques to get an optimal estimate of the vector. The equations above are similarly adapted to solve for the toe vector when toe-strike initiates the early stance phase.

FIG. 6A illustrates the inertial measurement unit-comp ted ankle joint pivot trajectories in different ambulation contexts for a wearer walking on various terrain: level ground (620), up a 5° ramp (624), down a 5° ramp (628), up a 10° ramp (632), down a 10° ramp (636), up stairs (640), and down stairs (644). Context is the shape of the terrain and how the wearer interacts with the terrain.

Figure 6B:
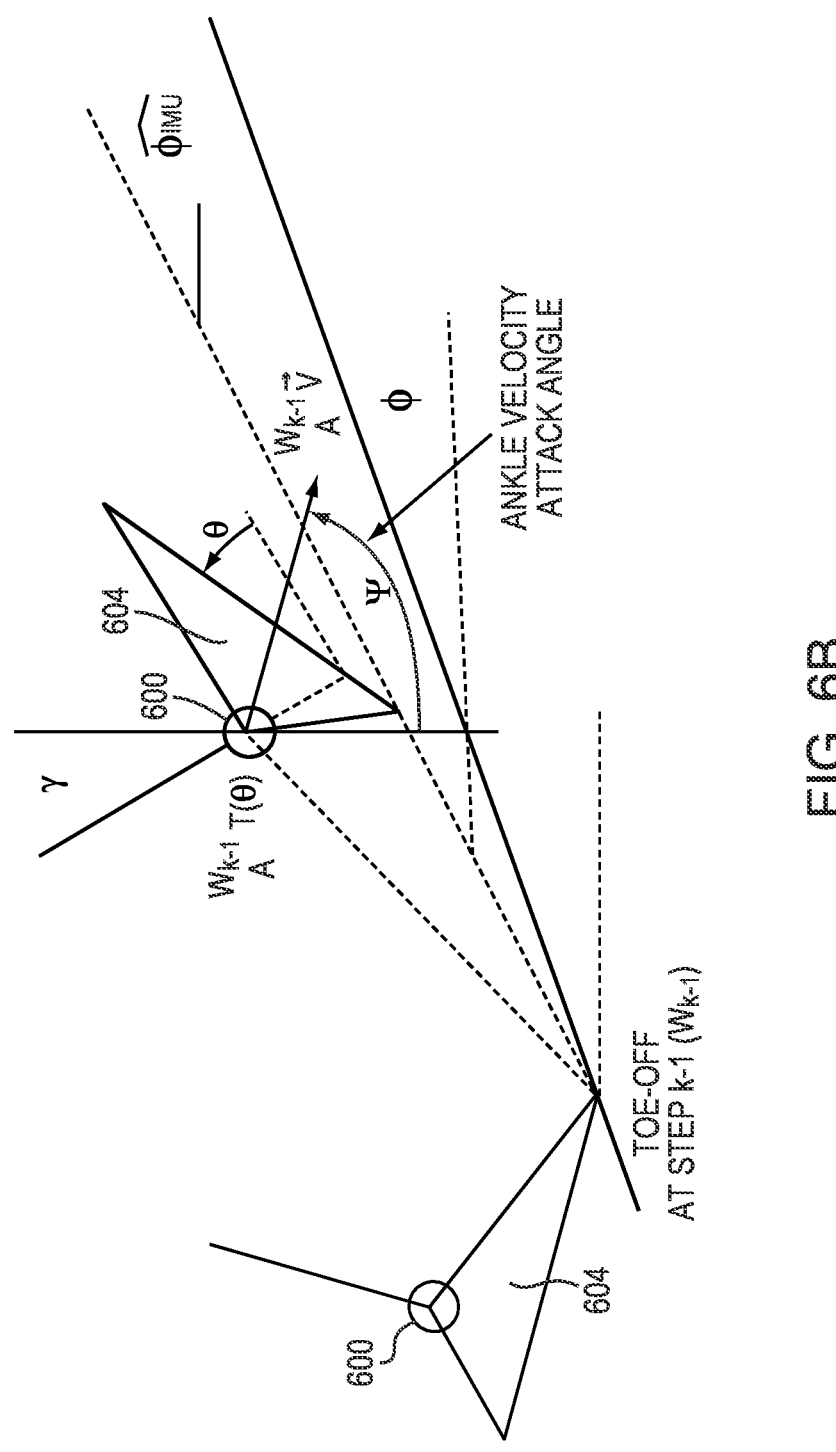
FIG. 6B illustrates the 2-D geometry that describes the in-flight trajectory of the ankle joint of the prosthetic apparatus.

FIG. 6B illustrates the 2-D geometry that describes the in-flight trajectory of the ankle joint of the prosthetic apparatus. If we treat level-ground walking as a subset of the ramp ascent/descent ambulation context (in which level ground is a zero degree ramp), then context discrimination devolves into discrimination of stair ascent/descent from ramp ascent/descent. This discrimination is important because typically in the stair context, plantarflexion (rather than dorsiflexion) of the ankle joint 600 is required to optimize foot-strike kinetics whereas in ramp ambulation typically the ankle joint 600 is dorsiflexed (or held neutral) to optimize foot-strike kinetics. In the latter context, it is only in extremely steep descent that a plantar flexed ankle would be the appropriate orientation.

Figure 6C:
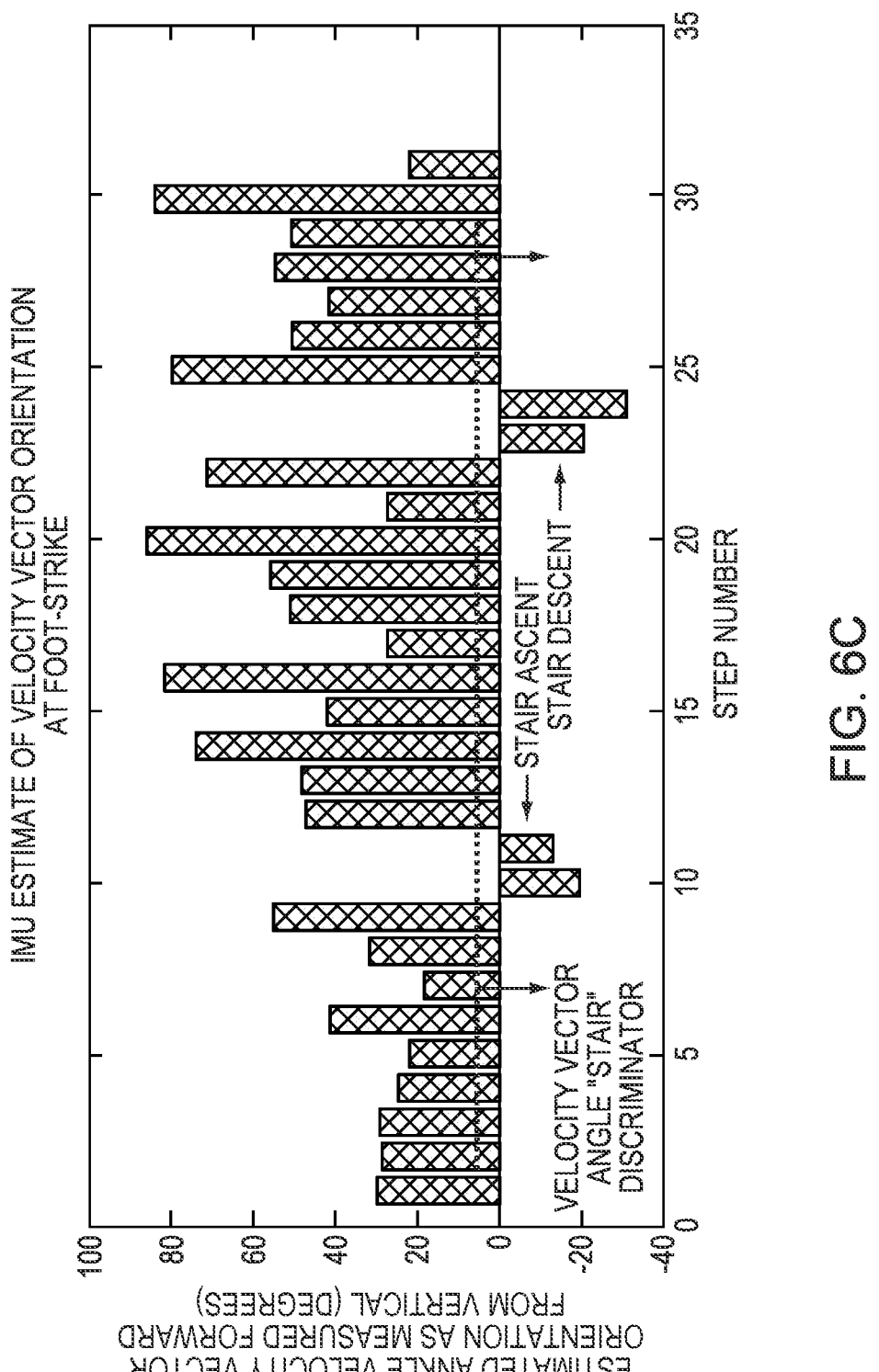
FIG. 6C illustrates how a stair-ramp discriminator can be built using the ankle angle attack angle as the trajectory feature that discriminates between the stair and ramp ambulation context, according to an illustrative embodiment of the invention.

FIG. 6C illustrates how a stair-ramp discriminator can be built using the ankle angle attack angle ($\Psi$) as the trajectory feature that discriminates between the stair and ramp ambulation context in a set of recorded data. FIG. 6C is a plot of the estimated velocity vector attack angle of the ankle joint 600 of the apparatus throughout a gait cycle versus each step taken by the wearer. In this data, an amputee fitted with the prosthetic apparatus 1700 of FIG. 17A on his right foot took thirty-one (31) steps (meaning walking cycles referenced to the right foot) in the following manner:

1. Steps 1-6: Six (6) steps up the 5° ramp
2. Step 7: One (1) step on the landing
3. Steps 8-9: Two (2) steps down the 10° ramp
4. Recording gap
5. Steps 10-11: Two (2) steps up the stairs
6. Steps 12-13: Two (2) steps on the landing
7. Step 14-17: Four (4) steps down the 5° ramp
8. Steps (18-19): Two (2) steps on level-ground
9. Steps (20-21): Two (2) steps up the 10° ramp
10. Step (22): One (1) step from the 10° ramp to the landing
11. Steps (23-24): Two (2) steps down the stairs
12. Steps (25-31): Seven (7) steps on level-ground.

The steps taken during this recording included both ramp and stair ascent and descent. FIG. 6C shows that stairs can be differentiated from ramps while the ankle is in-flight prior to foot-strike by monitoring the ankle velocity attack angle ($\Psi$). When ($\Psi$) drops below a small positive value in this recording (and other similar recordings) the foot 604 always lands on a stair. In all other cases, the foot lands on a ramp, irrespective of ramp angle (0°, −5°, +5°, −10°, +10°). $\Psi$ is therefore a suitable ambulation task context discriminator that can be used by the processor to determine what activity is being performed.

Alternative methods for stair-ramp discrimination can be employed in other embodiments of the invention. The attitude (orientation in inertial space) lower leg member 608 (shank) and the ankle velocity attack angle ($\Psi$) can be used in one embodiment of the invention to distinguish between stairs or a ramp/level ground. The trajectory of the ankle joint 600 in the y-z plane (referring to FIG. 6A) could be used in an alternative embodiment of the invention for stair-ramp discrimination.

Swing Phase Ankle Positioning

The stair ramp discriminator provides a real-time prediction of the terrain slop angle, $\hat{\phi}(t)$. If the discriminator detects a step, including level-ground, then $\hat{\phi}(t)=0$. Otherwise, the slope angle is assumed to be:

$$\hat{\phi}(t) = \min\left(\tan^{-1}\left(\frac{({}^{w}p_{heel}(t) - {}^{w}p_{toe}(0))_z}{({}^{w}p_{heel}(t) - {}^{w}p_{toe}(0))_y}\right),\right.$$ EQN. 31

-continued
$$\left.\tan^{-1}\left(\frac{({}^{w}p_{toe}(t) - {}^{w}p_{toe}(0))_z}{({}^{w}p_{toe}(t) - {}^{w}p_{toe}(0))_y}\right)\right|$$

This slope angle corresponds to the minimum value possible given that the foot has not struck the ground. $\hat{\phi}(t)$ is this the minimum value of two possible slope angles—the angle that the heel currently makes relative to the toe position from the last step and the angle that the toe makes relative to the toe position from the last step.

Once $\hat{\phi}(t)$ is known, it is possible to apply various different methods to position the ankle in a way that adapts to this predicted terrain slope. Two examples of such methods are described below. In one embodiment of the invention, the discriminator methodology described above is used to control at least one of joint impedance, position or torque of a lower extremity prosthetic, orthotic, or exoskeleton apparatus worn by a wearer (e.g., the apparatus 1700 of FIG. 17A). The method involves estimating a velocity vector attack angle of the ankle joint of the apparatus throughout a late swing (e.g., the y-axis values of the data in FIG. 6C). In one embodiment, the method also involves adjusting the position of the foot member of the apparatus to a toe down position when the velocity vector attack angle has a predetermined sign (e.g., a negative value in the case of the data in FIG. 6C). In an another embodiment of the invention, the method involves adjusting the position of the foot member of the apparatus to a heel down position when the velocity vector attack angle has an opposite sign as the predetermined sign (a positive sign).

In some embodiments, the method includes adjusting the impedance of the apparatus (e.g., the ankle joint impedance) to minimize a cost function based on projected force imparted on the lower leg member during a period of time between when a heel of the foot member strikes the underlying terrain to when the foot member is positioned in a flat-foot position relative to the underlying terrain.

Figure 7A:
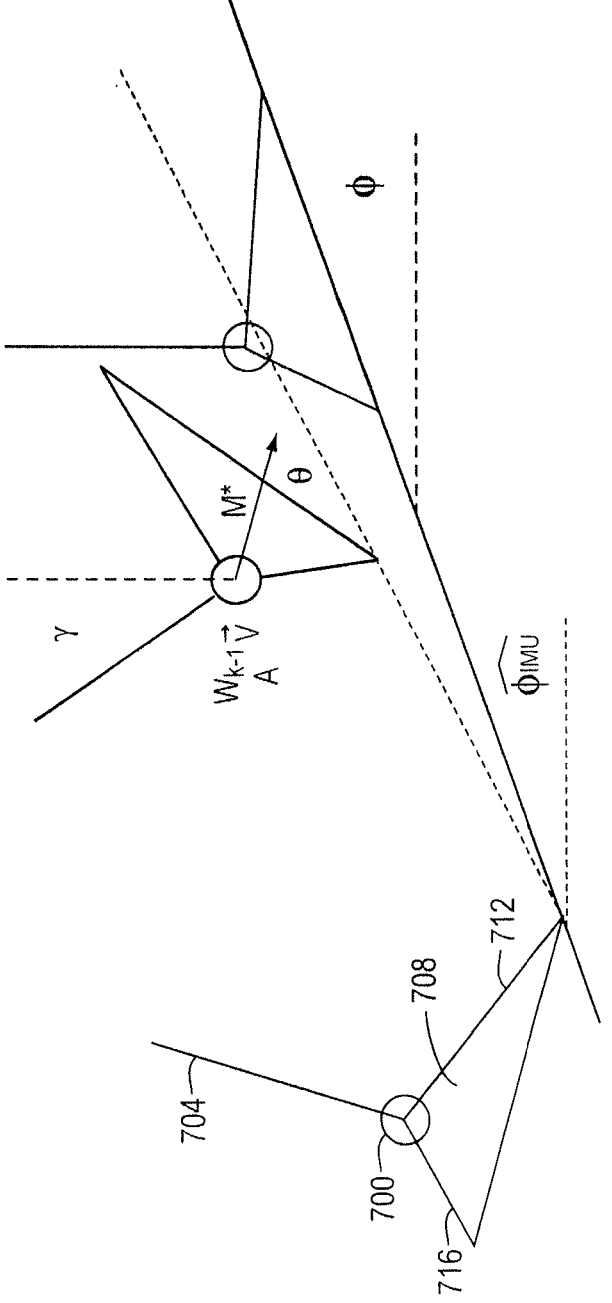
FIG. 7A illustrates a method for positioning an ankle joint prior to foot strike, according to an illustrative embodiment of the invention.

FIG. 7A illustrates a method for positioning the ankle joint 700 prior to foot strike. In this method, the ankle joint angle is optimized so as to minimize a cost functional based upon the projected force (f(t)) imparted on the ankle joint 700 from foot member 708 strike to foot-flat. Both heel-first 716 and toe-first 712 strategies are evaluated, and a strategy, including optimal ankle joint 700 angle, which minimizes the cost functional is selected. FIG. 7A describes the method used.

Figure 7B:
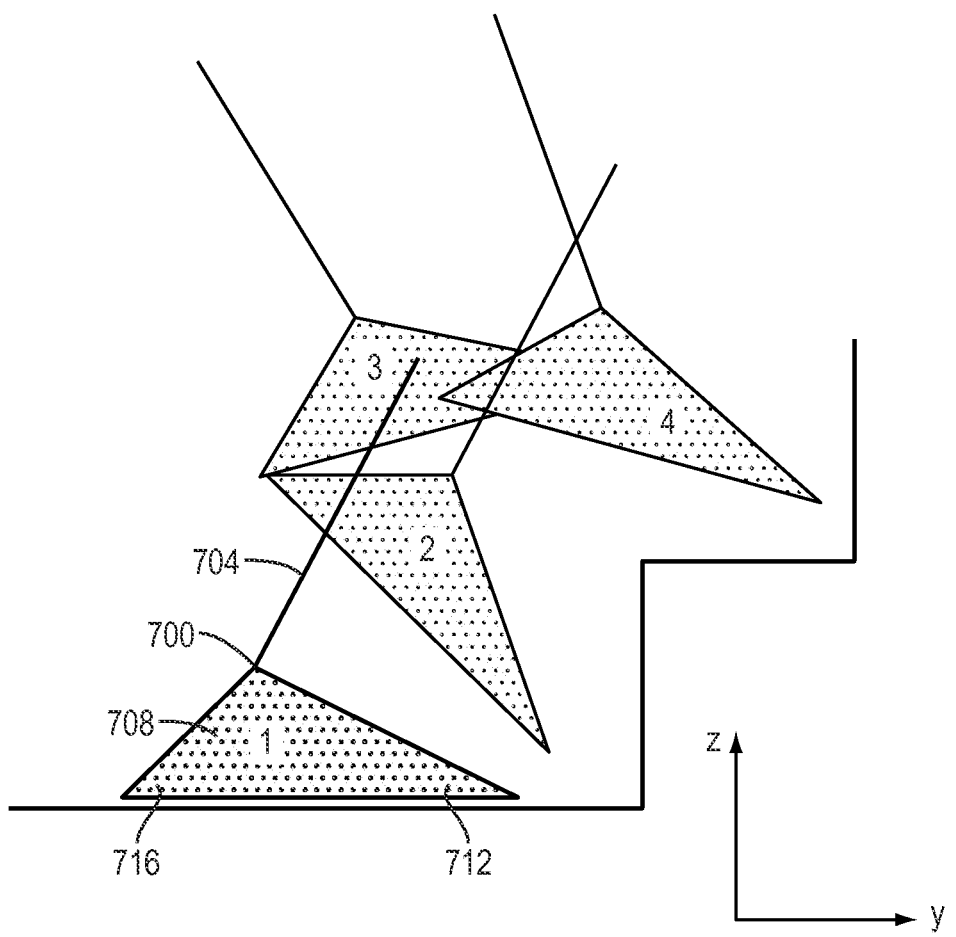
FIG. 7B illustrates how the method of FIG. 7A can be used to sense the presence of stairs and overhang of the foot on the landing of the stair, according to an illustrative embodiment of the invention.

In another embodiment, the method of FIG. 7A is augmented as shown in FIG. 7B to sense the presence of stairs, and to constrain the angle-of-attack optimization to toe-strike only in the event of stairs with short landing areas. For ascending or descending a steep, narrow set of stairs, the prosthetic apparatus is programmed to keep track of the volume swept by the foot during ascent-a volume for which there has been no contact between the foot and the stairs. If in late swing, there is determined to be no landing area for, for example, the heel, the optimization is constrained to be the toe-down solution. In this embodiment, a z-rotation is a rotation about the longitudinal axis of the lower leg member 704 (e.g., the z-axis of FIG. 17A) of the apparatus. If one descends stairs and rotates the foot member 708 in this way, it is likely that the landing area is limited and the foot member 708 must be rotated to land squarely on the stair. In this case, the toe 712 down landing yields the only available minimum force solution for the method of FIG. 7A. Such z-rotation would signal the system that the landing area is limited, making a toe-down landing the safest alternative when compared to heel-down.

The complex impedance computation employed in the method above can be applied to any adaptive ankle positioning method as a means of minimizing foot slap or use of excessive braking force as the ankle joint 700 rotates to the foot down state. FIG. 7D illustrates how the method of FIG. 7A is adapted to use the optimized impedance. Once the optimum angle-of-attack ($\psi^*$) is found, an optimal control ($\Gamma_c^*(t)$) is found that will bring the linear and angular momentum of the ankle joint to zero without foot-slap. The corresponding ankle angle response ($\theta^*(t)$) is then used as the equilibrium trajectory. A corresponding optimal impedance, in relation to this optimal trajectory, can be derived to accommodate the uncertainty in the momentum and the local terrain angle.

Figure 7C:
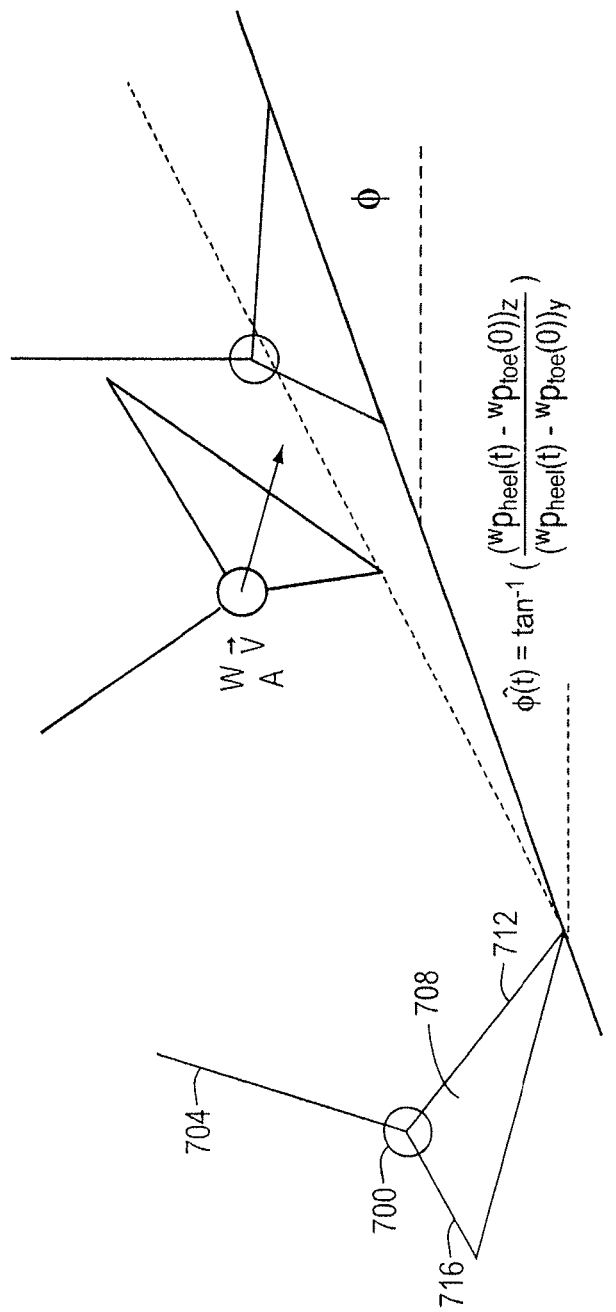
FIG. 7C illustrates a method for positioning an ankle joint in a ramp ambulation context, according to an illustrative embodiment of the invention.
Figure 7D:
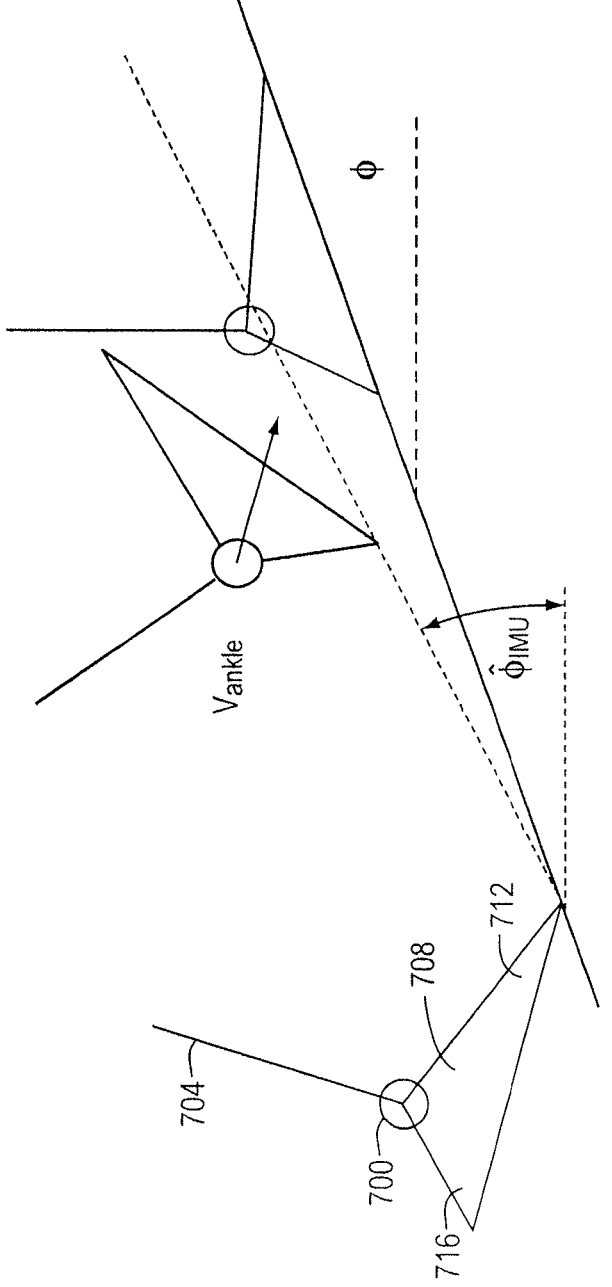
FIG. 7D illustrates how the method of FIG. 7B is adapted to use the optimized impedance, according to an illustrative embodiment of the invention.

A simpler method can also be used as shown in FIG. 7C. FIG. 7C illustrates a method for positioning the ankle joint in a ramp ambulation context. In this method, the ankle joint 700 angle is articulated so as to be in the foot-flat position on a sloped-terrain (with slope angle $\hat{\phi}(t)$) when the lower leg member 704 is vertical. It is also useful to generalize this method to adjust the ankle angle to be linearly related to the predicted slope angle by the relation:

$$\theta(t) = k\overrightarrow{\phi}(t) + \theta_0 \qquad \text{EQN. 32}$$

Using this relationship the ankle angle can be adjusted to suit the wearer preferences.

In either of the two methods described above, the ankle joint angle 700 prior to foot-strike will be controlled (steered) continuously to coincide with the desired ankle joint 700 angle until the foot strikes the ground.

Stance Phase Impedance and Torque Control

Figure 8:
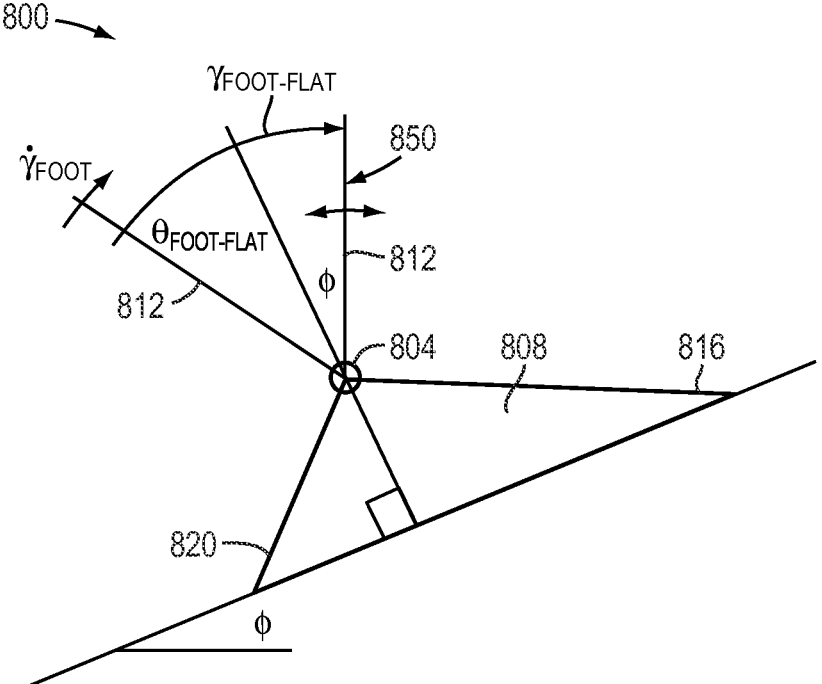
FIG. 8 illustrates a method for determining the inertially-referenced spring equilibrium based on the terrain angle at foot-flat.

The next step involves restoring the orientation of the lower leg (shank) to align with the local vertical during stance phase. FIG. 8 illustrates a method for determining the inertially-referenced spring equilibrium based on the terrain angle at foot-flat of a lower-limb prosthesis 800, for example, the prosthesis apparatus 1700 of FIG. 17A. The prosthesis 800 has a foot member 808 with a toe 816 and heel 820. The prosthesis also has an ankle joint 804 and lower leg member (shank) 812. The terrain angle ($\phi$) is an input to the control system. The control system shifts the curve ($\Gamma-\Theta$) (thereby altering the impedance of the ankle joint $K_{controlled\ plantarflexion}$) in FIG. 10A based on the change in terrain angle ($\phi$) to maintain or improve the overall balance (as described an illustrated in FIG. 10F) of the wearer during controlled plantarflexion. The control system sets the impedance of the ankle joint 804 of the prosthesis such that the ankle equilibrium angle is equal to the terrain angle ($\phi$); and the control system restores the orientation of the lower leg member 812 (shank) to align with the local vertical 850.

Figure 9:
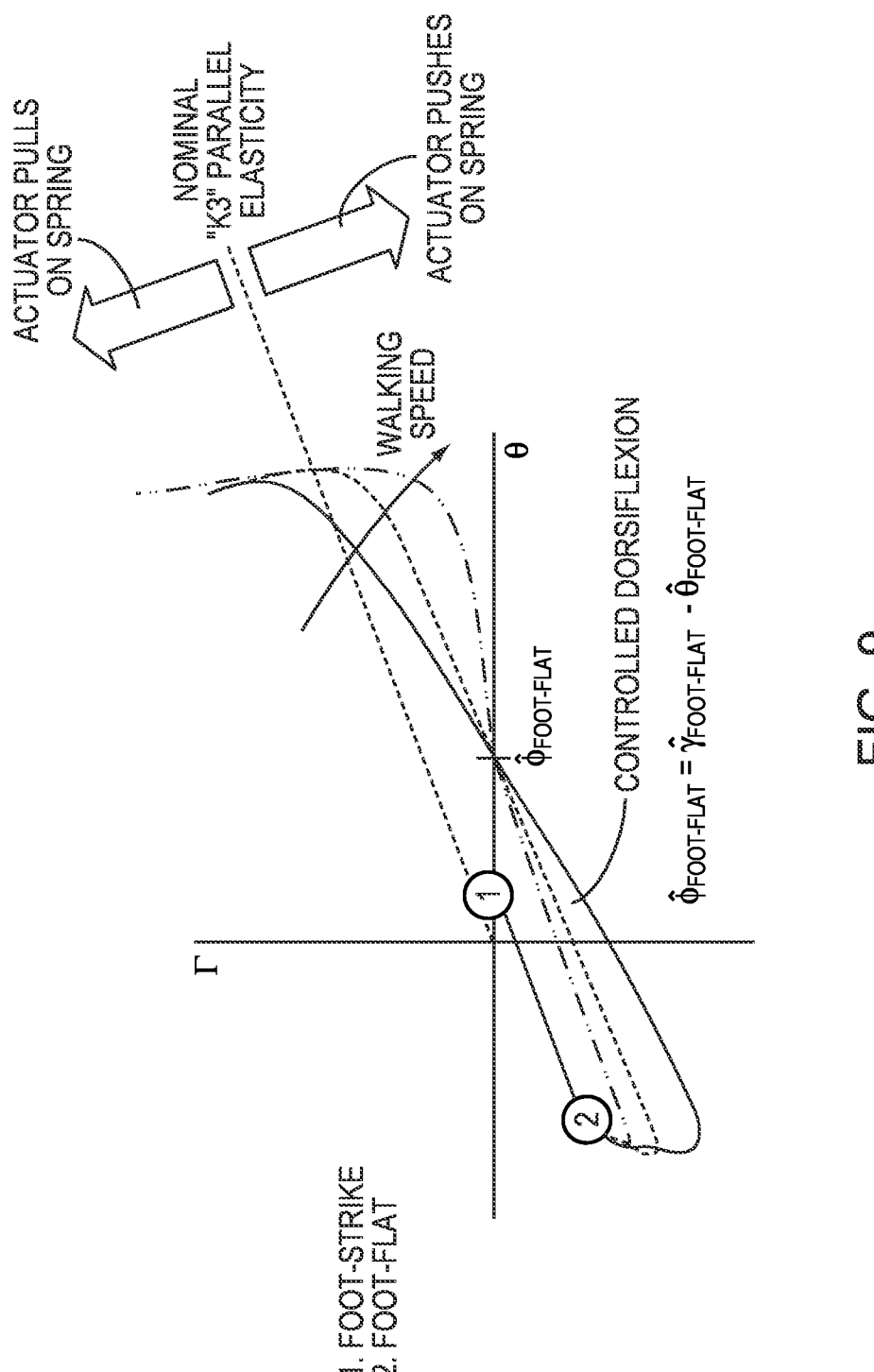
FIG. 9 illustrates the effect of walking speed on ankle torque versus ankle angle and shows how a push-pull actuator control applies to an appropriately selected parallel elastic element.

FIG. 9 illustrates the effect of walking speed on ankle torque versus ankle angle during controlled dorsiflexion. The control system shifts the curve ($\Gamma-\Theta$) (thereby altering the impedance of the ankle joint 804 $K_{controlled\ dorsiflexion}$) in FIG. 10A based on the change in terrain angle ($\phi$) to maintain or improve the overall balance of the wearer during controlled plantarflexion by commanding the ankle joint 804 to move the lower leg member (shank) 812 towards the equilibrium point.

Figure 10A:
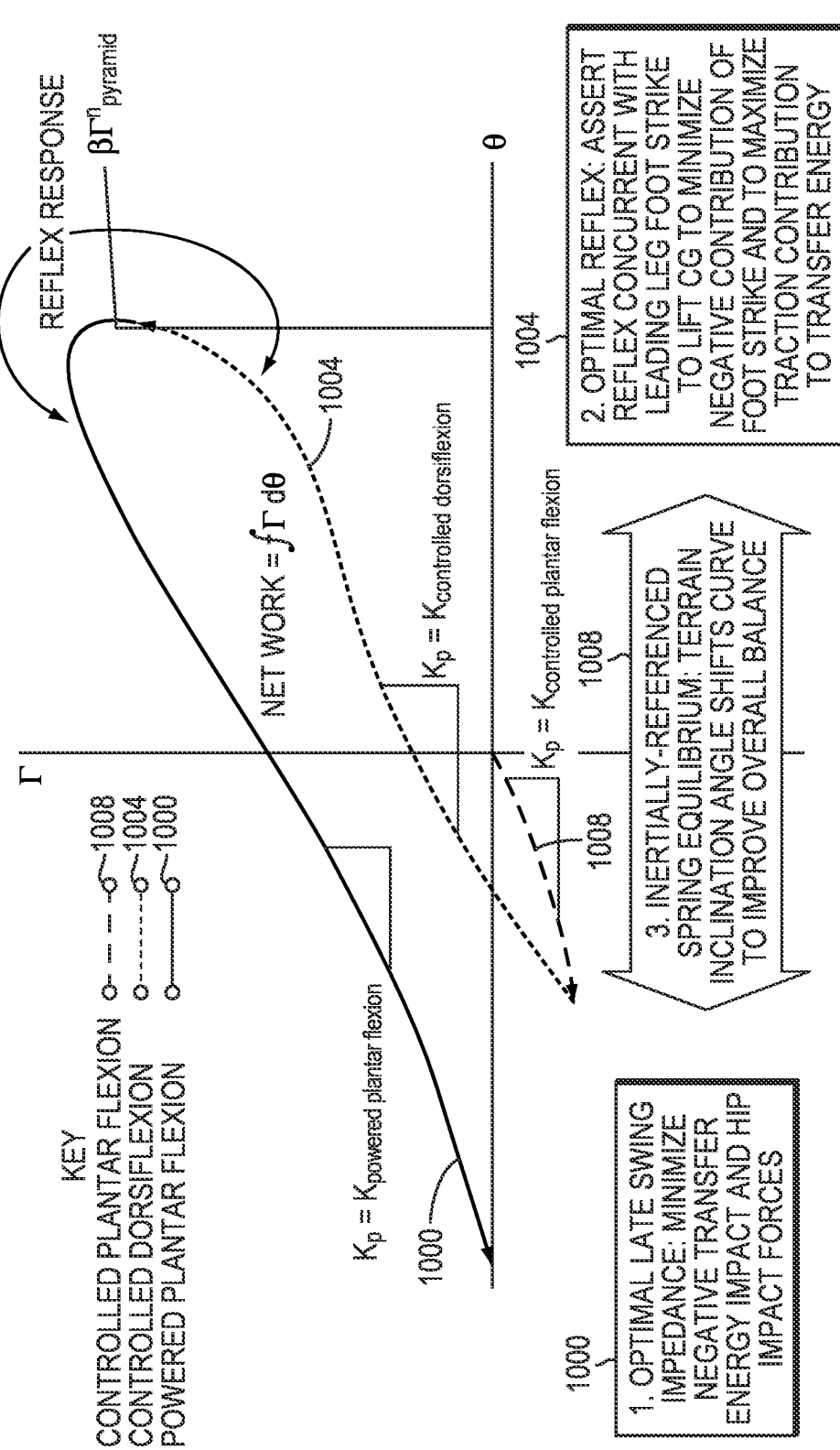
FIG. 10A illustrates a method for controlling a lower-extremity apparatus, according to an illustrative embodiment of the invention.

FIG. 10A illustrates a method for controlling a lower-extremity apparatus, according to an illustrative embodiment of the invention. As shown in FIG. 10A, this is achieved in the control system by 1) adjusting the late swing impedance (step 1000) (the dynamic stiffness and ankle-angle equilibrium angle) so as to soften the impact between the time interval between foot-strike and foot-flat, as described herein with respect to FIG. 7A (the controller shifts the curve ($\Gamma-\theta$) (thereby altering the impedance of the ankle joint $K_{powered\ plantarflexion}$) based on a minimization of the negative transfer energy impact and hip impact forces during powered plantarflexion.

2) introducing a lifting force in the trailing leg accomplished by asserting a reflex response in the ankle (and knee) at or before the time of impact of the leading leg (step 1004); and 3) maintaining an inertially-referenced equilibrium angle in the controlled dorsiflexion phase to maintain balance (equilibrium) (as described an illustrated in FIG. 10F) on sloping terrain (step 1008).

Figures 10B, 10C:
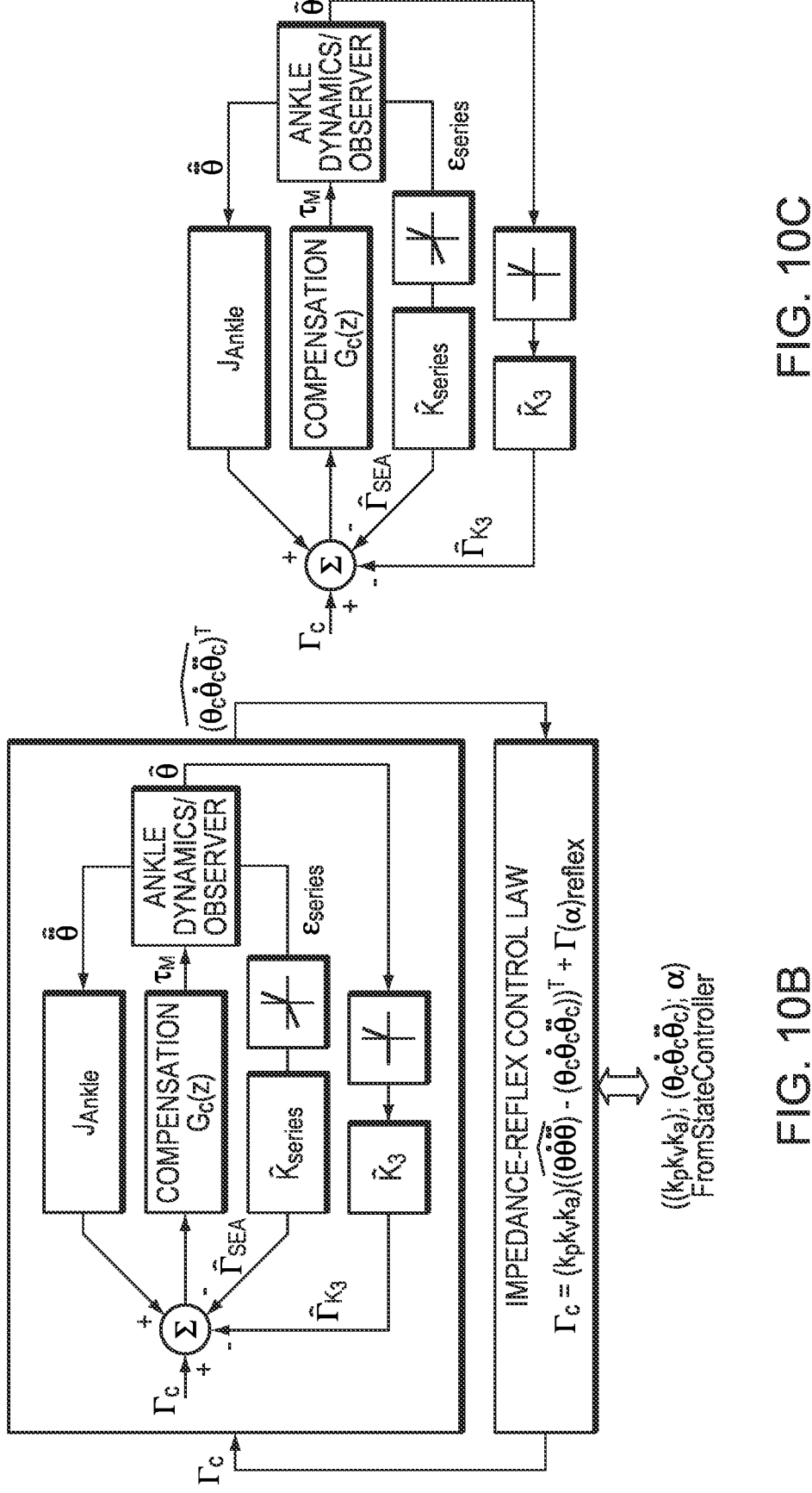
FIG. 10B is a schematic illustration of a model-based controller for implementing impedance and torque control in a lower-extremity prosthetic apparatus, according to an illustrative embodiment of the invention.
FIG. 10C is a schematic illustration of a model-based controller for implementing torque control in a lower-extremity prosthetic apparatus, according to an illustrative embodiment of the invention.

FIG. 10B is a schematic illustration of controller for implementing impedance and torque control in a lower-extremity prosthetic apparatus (e.g., the apparatus 1700 of FIGS. 17A-17E), according to an illustrative embodiment of the invention. FIG. 10E is a schematic illustration of the impedance and reflex relation that governs the impedance and reflex control performed in FIG. 10B.

As shown, the spring, damping and inertial components of the impedance are defined in relation to a trajectory, $\theta_0(t)$. Both the impedance gain matrix and trajectory illustrated in FIG. 10B are loaded adaptively and in real-time from the state controller processor in accordance with the phase in the gait cycle, the terrain context, terrain texture and walking speed as described above.

Studies have shown that intact limbs exhibit reflex responses that arise from non-linear positive torque (force) and non-linear positive joint velocity feedback. The reflex relations as illustrated in FIG. 10E employ both types of feedback. Other non-linear implementations of these positive feedback relations can be used, including piece-wise linear and piece-wise non-linear as would be obvious to those skilled in the art. In the preferred embodiment, positive torque feedback is achieved by measuring the torque in the shank of the ankle prosthesis and employing this as the non-linear feedback signal, $\hat{\Gamma}$. In other implementations, this reflex torque input can be estimated using a model-based computation of ankle dynamics.

The inventors have observed that the biomimetic impedance and reflex in stance are coupled when the effects of walking speed and terrain slope are taken into account as shown in FIG. 9. For this reason, in one preferred embodiment, the parallel elasticity (e.g., parallel, or K3 spring) for the prosthesis is picked so as to represent the stiffness for the slow walking speed as shown. In biomimetic systems, the stiffness component of the prosthesis is attenuated at higher walking speeds and the reflex response is steeper as shown in FIG. 9. Through this-optimal biomimetic control and mechanical implementation, the response then requires the actuator to push on the parallel spring in controlled dorsiflexion and to pull on it in powered plantar flexion. We call this bipolar, or push-pull, operation. In non-optimal control and mechanical implementations, the reflex is implemented by a unipolar, pulling-force-only of twice the magnitude. The preferred embodiment thereby reduces the peak actuator force and motor current by a factor of two, thereby extending the actuator design-life by 8× and reducing ball-nut speed by nearly a factor of two when an appropriate bilateral series spring response is chosen. This has tremendous advantages in increasing the actuator durability, reducing actuator weight—the number of ball-bearings and ball-nut diameter needed to achieve a design life target are reduced—and reducing acoustic noise.

FIG. 10C is a schematic illustration of a controller for implementing impedance control in a lower-extremity prosthetic apparatus (e.g., the apparatus 1700 of FIGS. 17A-17E), according to an illustrative embodiment of the invention. FIG. 10D is a schematic illustration of the mechanical impedance relation that governs the impedance control performed in FIG. 10C. $\tau_M$ is the torque applied by the linear actuator to the ankle joint of a lower extremity prosthetic apparatus. Through suitable "high-gain" compensation, $G_c(z)$, where z denotes a discrete-time signal transform, it is obvious that the motor torque will work to make the sum of the torques applied by 1) the series-elastic actuator, 2) the "K3" parallel elasticity and 3) the acceleration torque on the ankle equal to the torque command, $G_c$, which is the desired result. The $\hat{K}_3$ and $\hat{K}_s$ are used to denote model estimates for these mechanical parameters, hence the reference to model-based control.

Figure 10F:
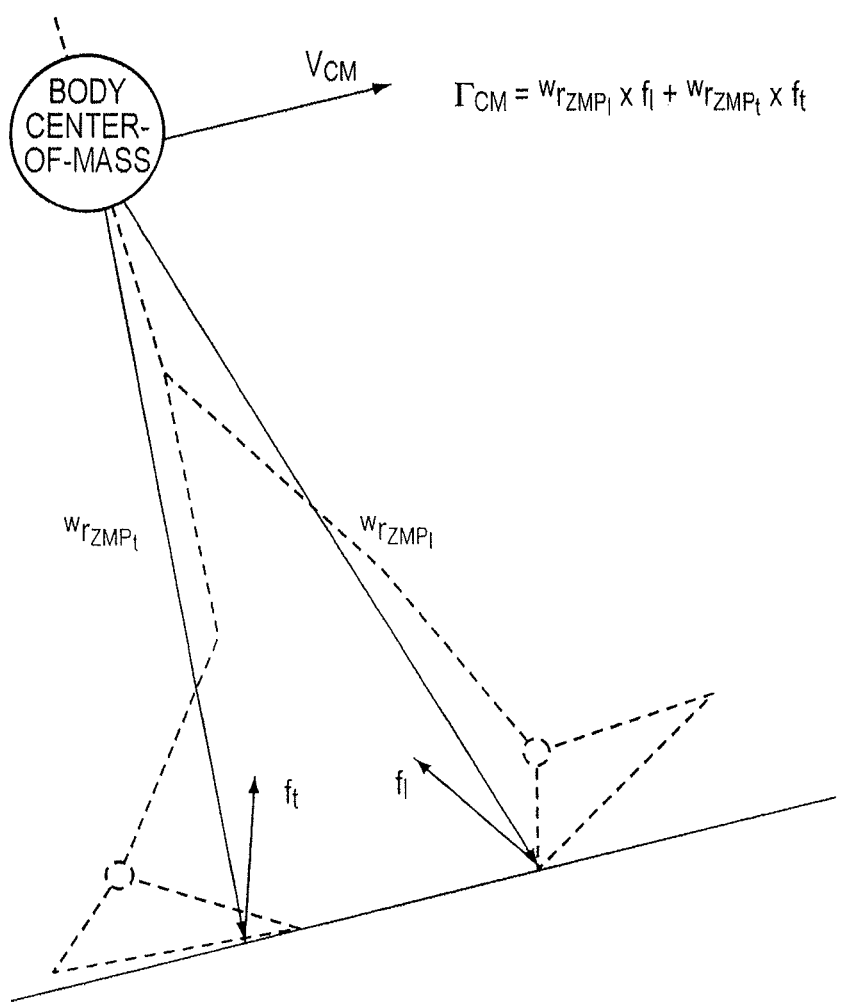
FIG. 10F is a schematic illustration of how zero moment pivot referenced ground reaction forces are used to determine the restoring torque necessary to stabilize inverted pendulum dynamics of a person wearing a prosthetic apparatus.

FIG. 10F is a schematic illustration of how zero moment pivot referenced ground reaction forces are used to determine the restoring torque necessary to stabilize inverted pendulum dynamics of a person wearing a prosthetic apparatus. The torque ($\Gamma_{CM}$) is applied at the center-of-mass of the system (combination of, for example, the person wearing the prosthetic and the prosthetic) to maintain the balance of the wearer based on the following:

$$\gamma_{CM} = {}^{w}r_{ZMP_l} \times f_l + {}^{w}r_{ZMP_t} \times f_t \qquad \text{EQN. 33}$$

where $f_l$ and $f_t$ are the ground reaction forces acting on the leading and trailing feet, respectively. $v_{CM}$ is the velocity vector of the wearer center-of-mass. $ZMP_l$ and $ZMP_t$ denote the zero moment pivot on the leading and trailing feet. ${}^{w}r_{zMPl}$ and ${}^{w}r_{zMPt}$ denote the world coordinate. referenced vectors between the center-of-mass and the zero moment pivots on the leading and trailing feet respectively. The term zero moment pivot refers to the inertially-referenced point on the foot about which the moment of the ground reaction force distribution is zero. We will also refer to this point as the center-of-pressure (CoP) interchangeably throughout the remainder of this document.

Ground Reaction Forces and Zero Moment Pivot

Ground reaction forces (GRF) are the forces imparted by and underlying surface onto the foot (or foot member of a lower-extremity apparatus). Ground reaction forces are important biomechanical inputs during stance. By knowing the aggregate ground reaction force acting at the zero moment pivot (referred to as ZMP and CoP herein), the control system (e.g., controller 1712 of FIG. 17A) of a lower-extremity prosthetic apparatus has a direct way of improving balance (of the wearer) and of optimizing power delivery during the stance phase. U.S. Pat. No. 7,313,463, issued to Herr et al. further describes estimating ground reaction forces and the zero moment pivot position as well as biomimetic motion and balance controllers for use in prosthetics, orthotics and robotics and methods (the entire contents of which are hereby incorporated by reference in its entirety).

Figure 11A:
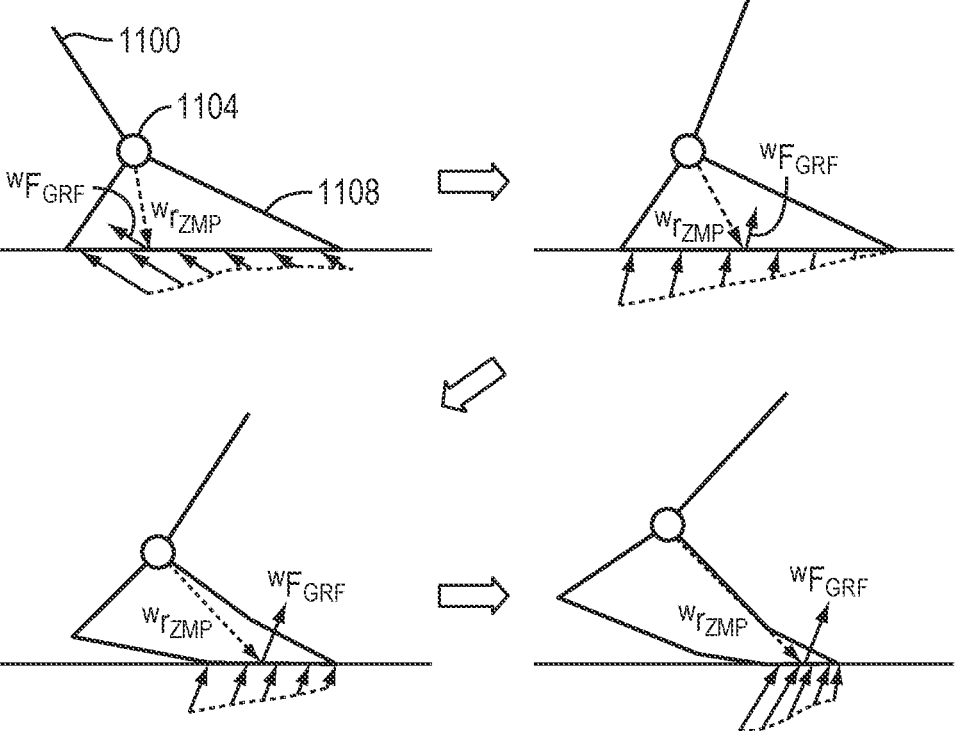
FIG. 11A is a schematic illustration of a lower leg foot member, ankle joint, and foot member of an ankle prosthesis showing ground reaction forces and the zero moment pivot.

FIG. 11A is a schematic illustration of a lower leg foot member 1100, ankle joint 1104, and foot member 1108 of a prosthesis (e.g., apparatus 1700 of FIG. 17A) that shows how the GRF components (specifically the vector from the ankle joint 1104 to the ZMP, ${}^{w}r_{ZMP}$, and the GRF vector, ${}^{w}F_{GRF}$) change during the stance phase in a typical walking cycle. The GRF estimation in research settings is often accomplished by applying sensors on the sole of the shoe. But, such extrinsic sensing may not be practical in prosthetic and orthotic devices because reliable packaging means should preferably survive the contact stresses over millions of walking cycles; which the sensors typically used in a research setting are unable to do so. Further, such means often require customization of the shoe which is often not acceptable to the wearer.

Figure 17B:
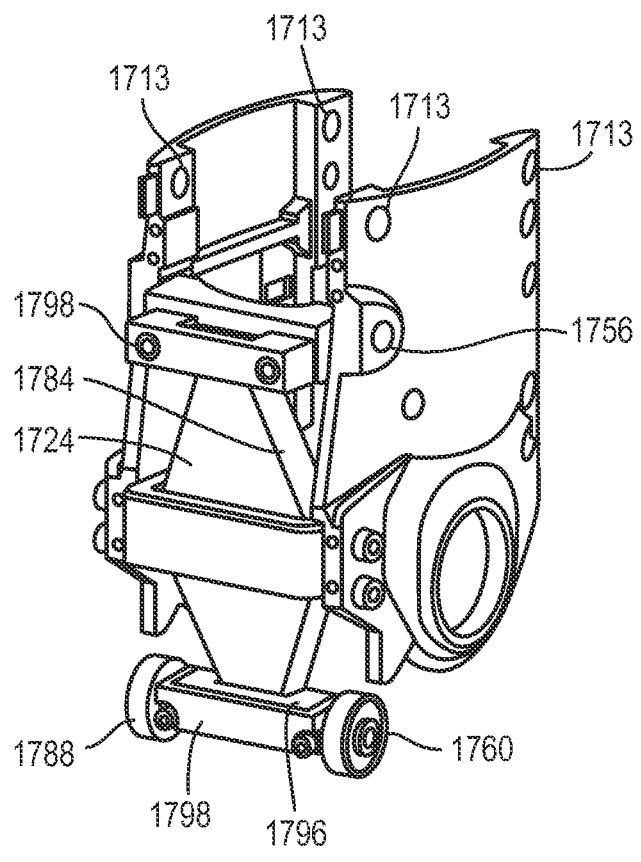
FIG. 17B is an illustration of a portion of the lower extremity apparatus of FIG. 17A that depicts a passive parallel elastic element.
Figure 17C:
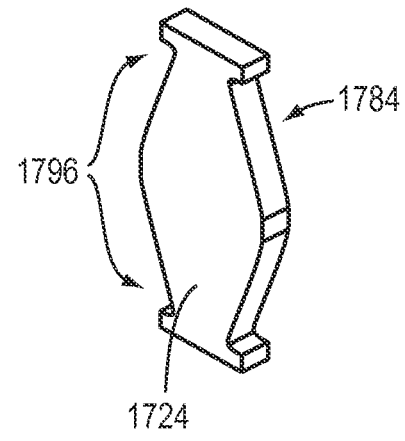
FIG. 17C is an illustration of the passive parallel elastic element of the apparatus of FIG. 17B.
Figure 17E:
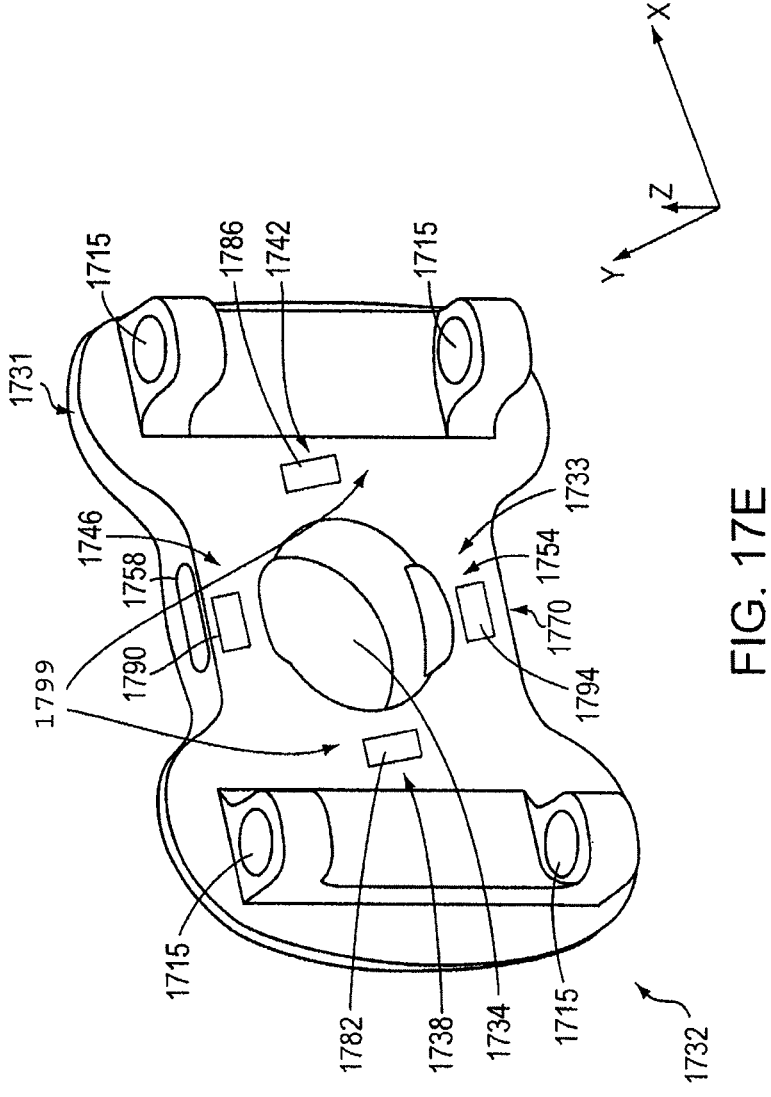
FIG. 17E is an illustration of a perspective view of the structural element (pyramid) of the apparatus of FIG. 17A, according to an illustrative embodiment of the invention.

In another embodiment of the invention, intrinsic sensing of the GRF is accomplished in a novel way by combining inertial state and lower leg member force/torque inputs 1112 (using, for example, the structural element 1732 of FIGS. 17A and 17E).

Figure 11B:
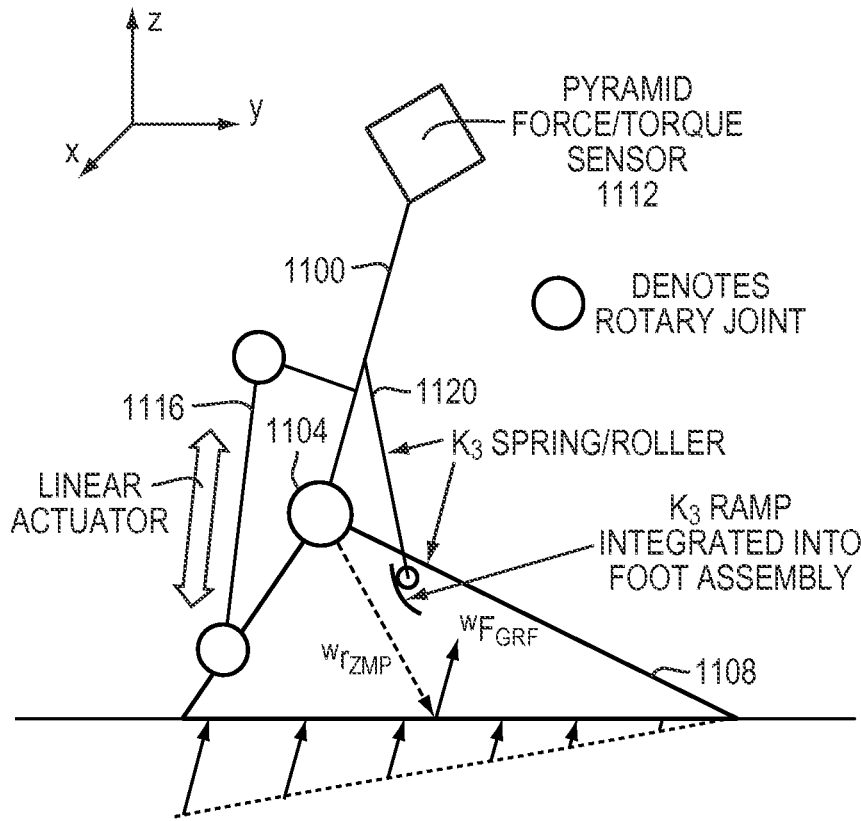
Figure 11D:
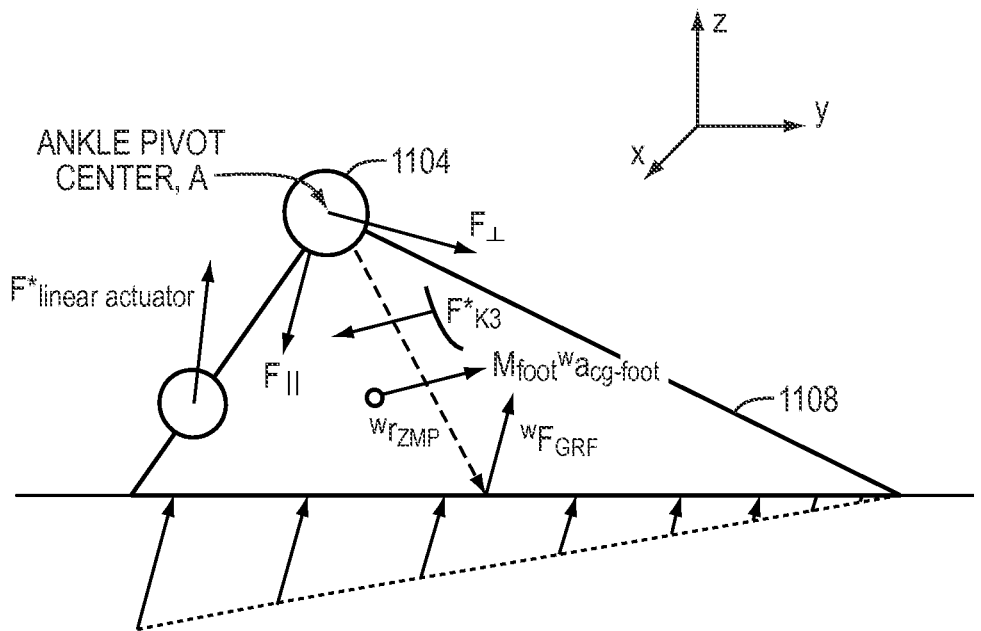

FIGS. 11B, 11C, and 11D are schematic illustration of the components of the apparatus 1700 of FIG. 17A. The figures also show the force and moment relationships among the components (linear series elastic actuator 1116 (e.g., combination of linear actuator 1716 plus series elastic member 1724 of FIG. 17A) and parallel spring 1120 (e.g., passive elastic member 1724 of FIG. 17A) necessary to determine the ground reaction forces and the zero moment pivot. ${}^{w}r_{ZMP}$ and ${}^{w}F_{GRF}$ are computed based on the following steps:

1. Update inertial state of the lower leg member 1100 and foot member 1108 using inertial measurement unit and ankle joint 1104 angle inputs. Using rigid-body assumptions, further calculate the world-referenced acceleration measured at the center-of-mass (CM) of the lower leg member 1100 and foot member 1108 and the angular velocity and acceleration of the lower leg member 1100 and foot member 1108.

2. Solve for $F_l^l$ as a function of the forces acting upon the lower leg member 1100 as these are resolved along the lower leg member 1100 axis.

3. Solve for F− as a function of the moments applied by each of the force and moment components acting upon the lower leg member 1100.

4. Solve for ${}^{w}F_{GRF}$ using the values for $F_l^l$ and F− computed in steps 2 and 3 above and then balancing the forces applied on the foot member 1100.

5. Balance the moments about the ankle joint 1104 assuming that ${}^{w}F_{GRF}$ is applied at the foot-ground boundary (i.e., ${}^{w}r_{ZMP}^{z}=0$).

6. Solve for ${}^{w}r_{ZMP}^{v}$.

Ankle Joint Behavior Due to Terrain Texture

Figure 12A:
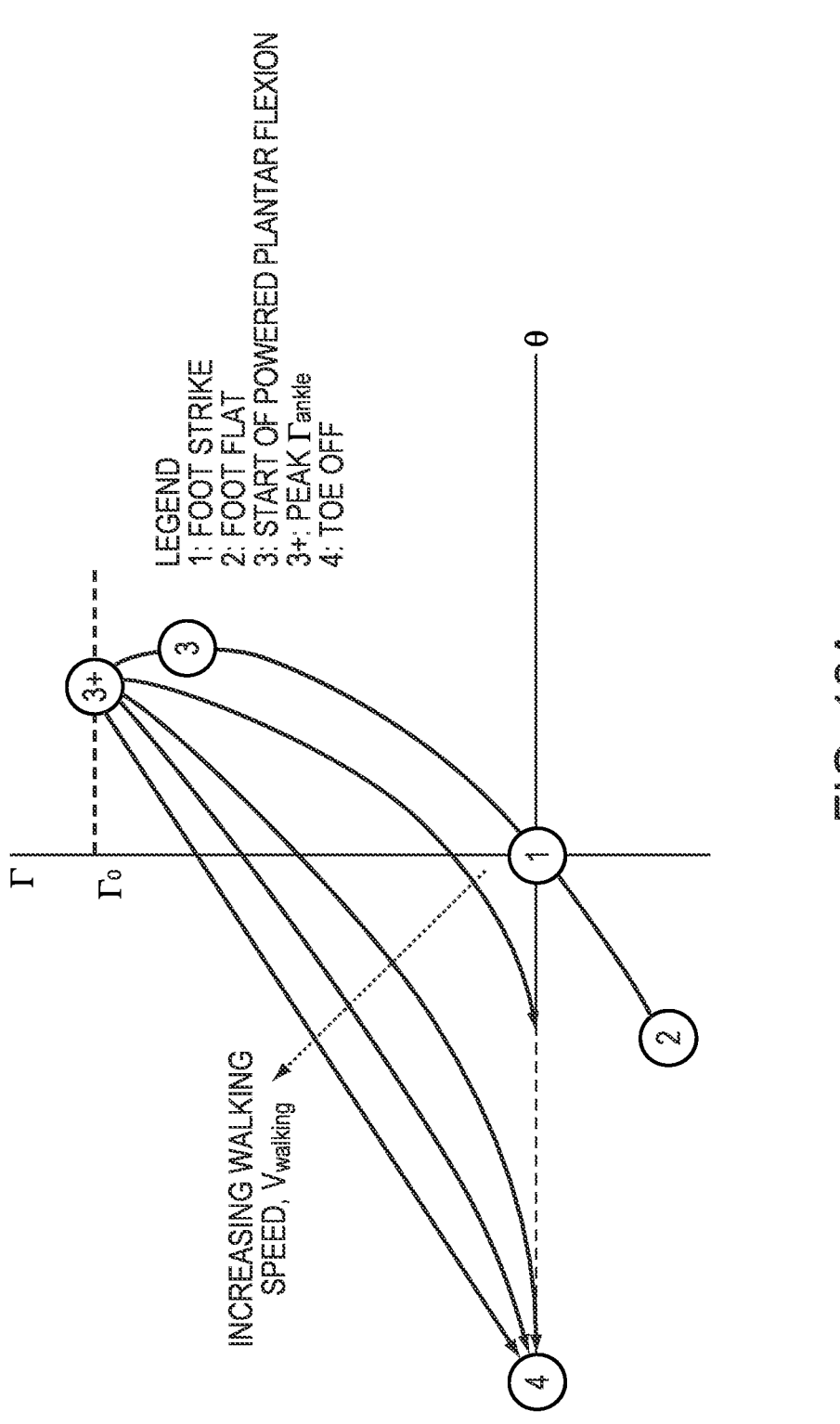
FIGS. 12A-12B illustrate the biomimetic ($\Gamma_0$) behavior of an ankle prosthesis on level ground as a function of walking speed during powered plantarflexion.
Figure 12B:
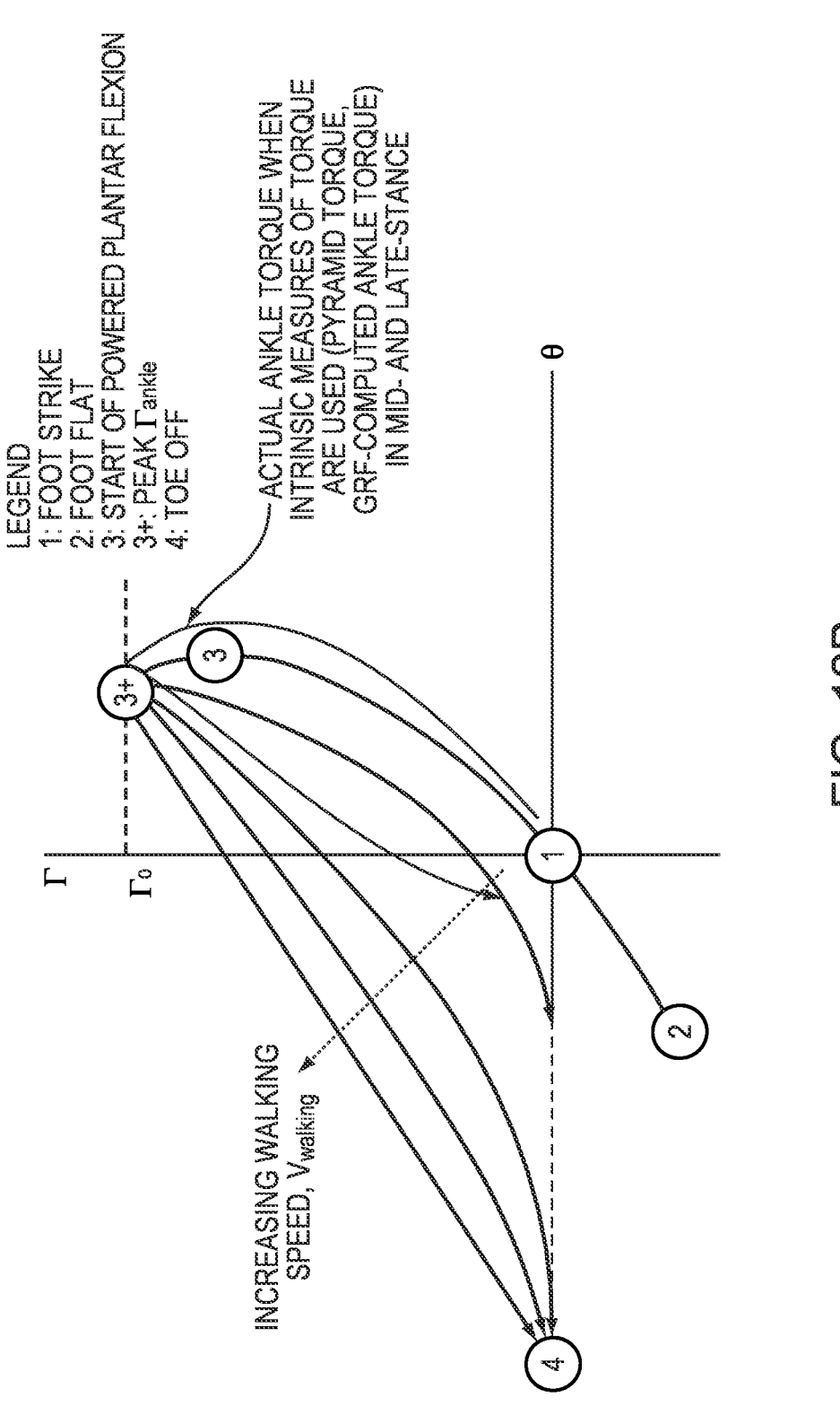

FIG. 12A illustrates the biomimetic [[G?]] $\Gamma_0$ behavior of a prosthetic apparatus (e.g., apparatus 1700 of FIG. 17A) on level ground as a function of walking speed. FIG. 12B shows that the applied ankle joint torque diminishes rapidly with angle during powered plantarflexion, thereby departing from the ideal biomimetic response and thereby significantly reducing the net work performed (area under the [[G?]] $\Gamma_0$ curve), particularly when walking at high speed.

In conventional robotic systems, trajectories or other playback means are employed to deliver repeatable and programmable responses. Such means are not preferable in prosthetic and orthotic devices because wearer intent may change in the middle of a playback segment. For instance, the wearer might be walking fast, then suddenly stop in front of a patch of ice for instance. If pre-programmed trajectories or other are played back, there is no easy way of aborting them without rapid changes of force and torque—and without introducing hazards. Indeed, that is why the intrinsic means are used.

Figure 12C:
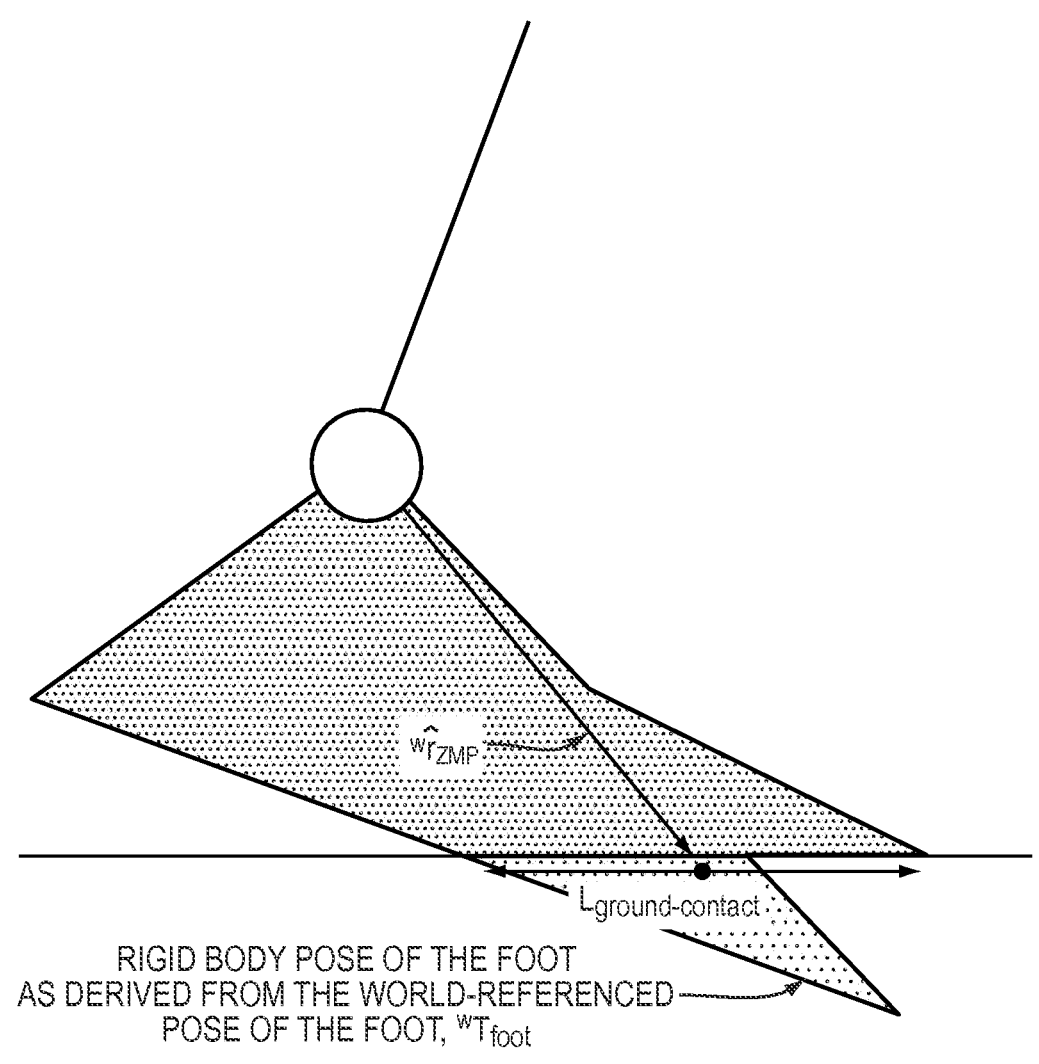
FIG. 12C-12D illustrate the effect of foot transitions on ground contact length.
Figure 12D:
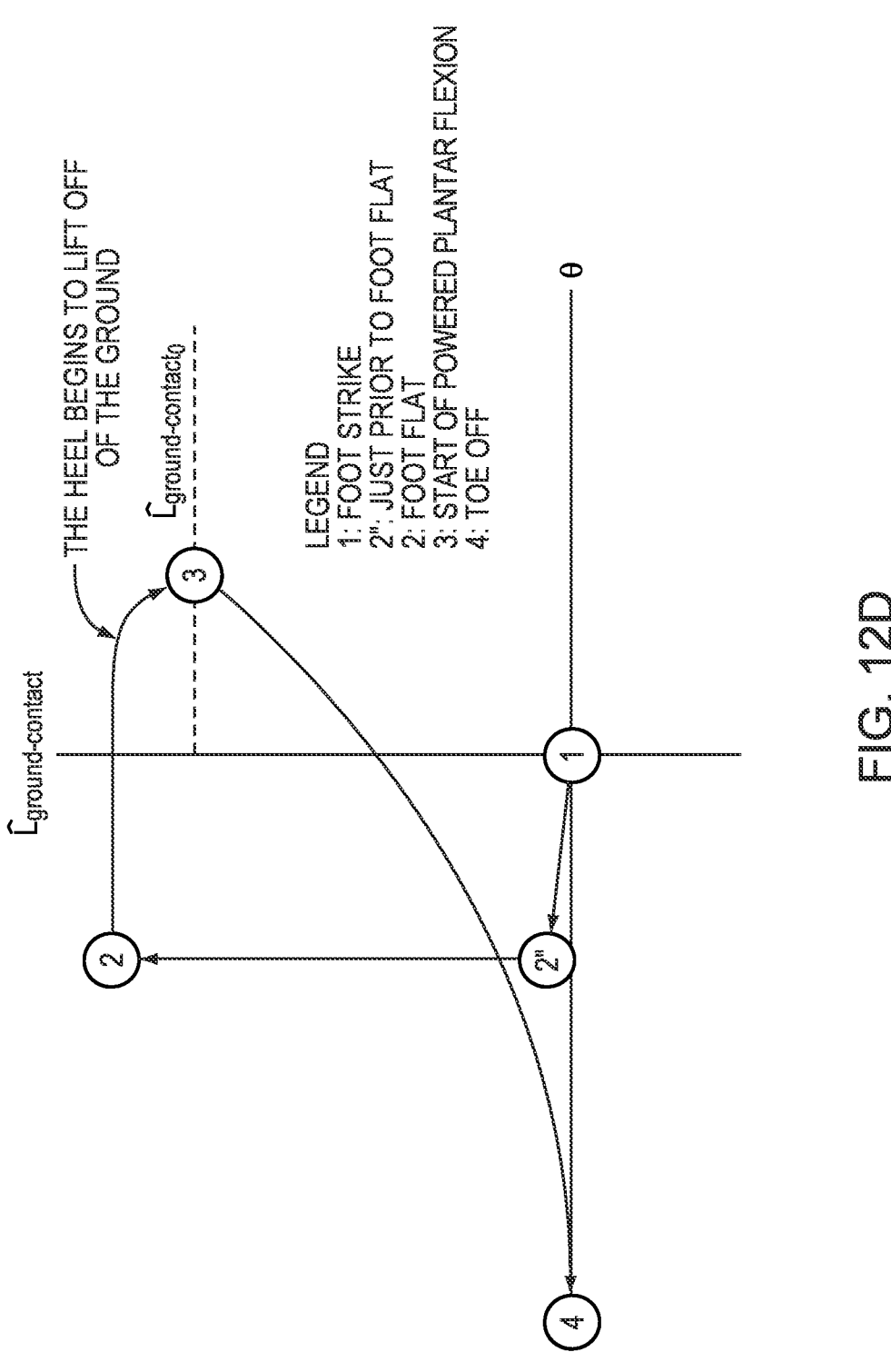

To extend the application of ankle joint torque during powered plantarflexion, walking speed-dependent normalized ground contact length are used as the means of attenuating the peak plantarflexion torque, $G_0$. Ground contact length is estimated by using an idealized model of the foot derived per the description related to FIGS. 2A-5 and by measuring the inertial pose of the foot member during controlled dorsiflexion and powered plantarflexion. As shown in FIG. 12C, as the foot transitions from foot flat to toe-off, sections of the idealized foot will fall below the terrain, enabling an estimate of ground contact length. FIG. 12D shows how $L_{ground-contact}$ changes from foot flat to toe off.

Figure 12E:
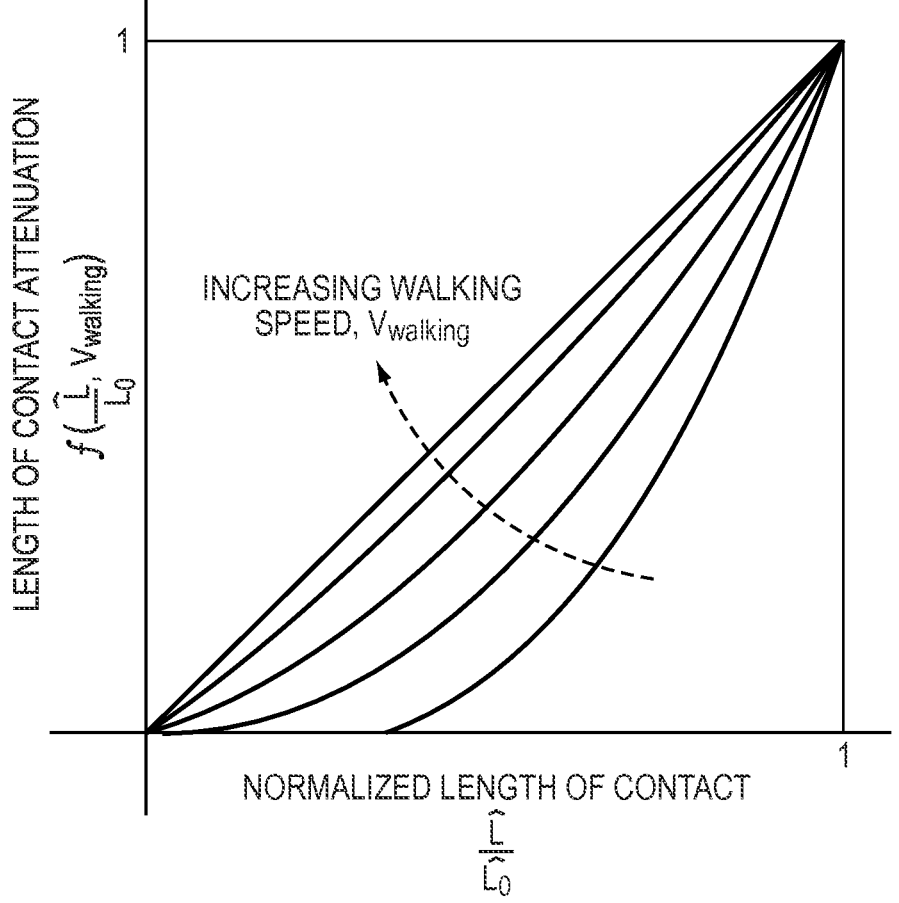
FIG. 12E illustrates how velocity-dependent tables of length of contact attenuation can use normalized ground contact length as a means to achieve biomimetic behavior during powered plantarflexion.

FIG. 12E illustrates how velocity-dependent tables of Length of Contact Attenuation can use normalized ground contact length as a means to achieve biomimetic behavior during powered plantarflexion. The tables can be computed by dynamically measuring the ground reaction force and foot member pose of non-amputees in controlled environments as a function of walking speed. The functional relationships between the attenuation function and ground contact length can be computed for each walking speed. These tables can be stored in the controller of the prosthetic apparatus as reference relationships. The functions can be shaped to suit specific wearer needs when the prosthetic apparatus is fitted to the wearer.

As described earlier, one of the motivations to use intrinsic feedback as opposed to explicit trajectory or playback means is to accommodate changes in wearer intent (e.g., decision to stop quickly). Intrinsic sensing using ground contact length as a means of attenuating ankle joint torque is not sufficiently general to accommodate changes in wearer intent involving stopping and changing direction. Referring to FIG. 12G, in one embodiment of the invention implemented on a prosthetic apparatus, a time-dependent attenuation factor $e\tau^{-t}$ is used in series with the ground contact length attenuation. The time constant for this attenuation, $\tau$, can be picked so as to extinguish the powered plantarflexion drive torque so as to prevent hazards associated with changes in wearer intent. $\tau$ will typically range from 50-100 msec.

Preferably, the prosthetic apparatus enables the wearer to walk faster with less effort on all terrain. It is not sufficient to accommodate just changes in terrain context (stairs, sloping ascent/descent). Changes in terrain texture as this might introduce slipping (e.g., Ice/snow) or sinking (mud, snow, sand, fine gravel) hazards should preferably be accommodated. Intrinsic sensing of the zero moment pivot trajectory can be used to optimize walking performance and/or to eliminate hazards while walking on varying terrain texture.

Figure 12F:
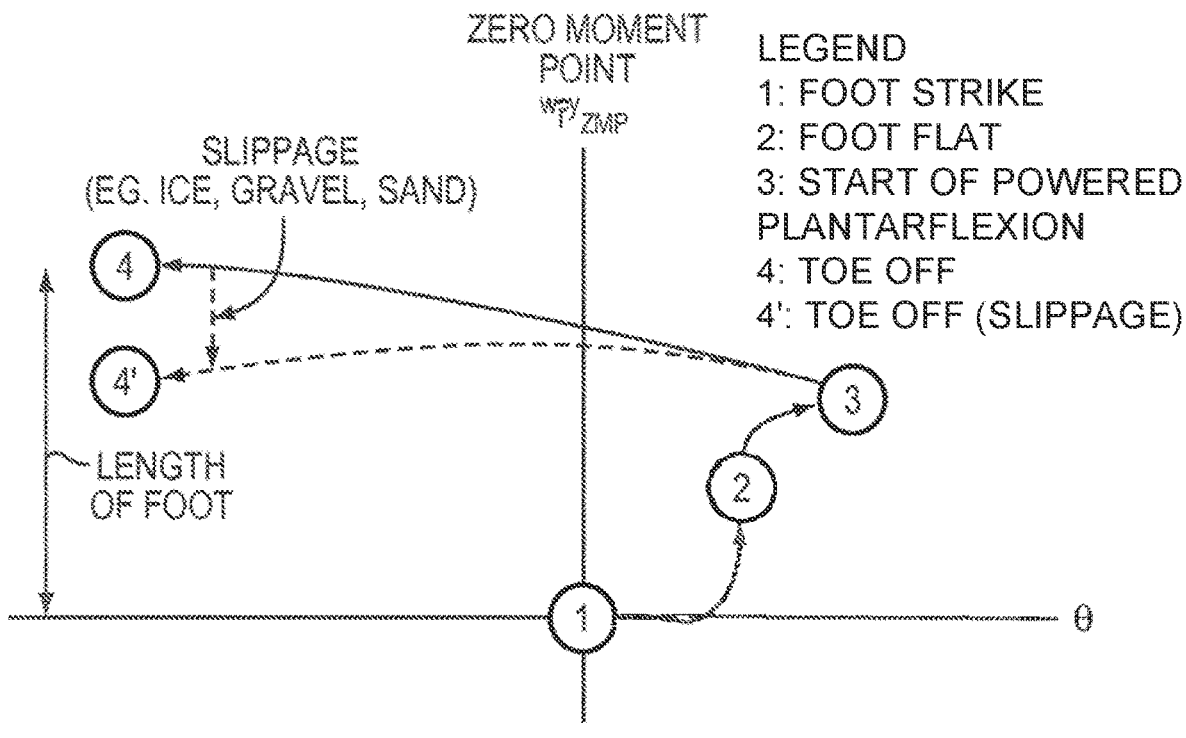
FIG. 12F illustrates how the estimated, y-component of the zero moment pivot vector changes during a typical walking motion.
Figure 12G:
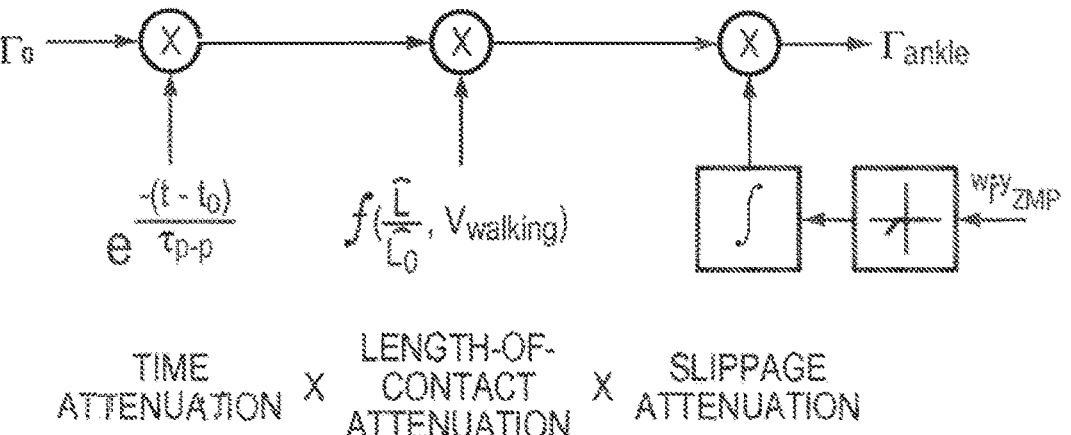
FIG. 12G illustrates a method for incorporating an attenuation factor into performance of an apparatus, according to an illustrative embodiment of the invention.

FIG. 12F illustrates how the estimated, y-component of the zero moment pivot vector, $^{w}r^{y}_{CoP}$, changes during a typical walking motion. As shown, in a no-slip condition $^{w}r^{y}_{CoP}$ must increase monotonically between the conditions of foot-flat (3) and toe-off (4). This is because it is the heel that is lifting off of the terrain surface during this period (increasingly as the walking cycle progresses). If the velocity of the zero moment pivot ever moves along the negative y-axis, the foot is slipping. In a fashion similar to how anti-lock brakes are implemented in vehicles, the prosthetic apparatus can reduce torque by an attenuation factor derived from the integral of the negative zero moment pivot velocity.

In one embodiment, so as to reduce noise sensitivity, only negative velocities below a noise threshold are integrated.

Figure 13A:
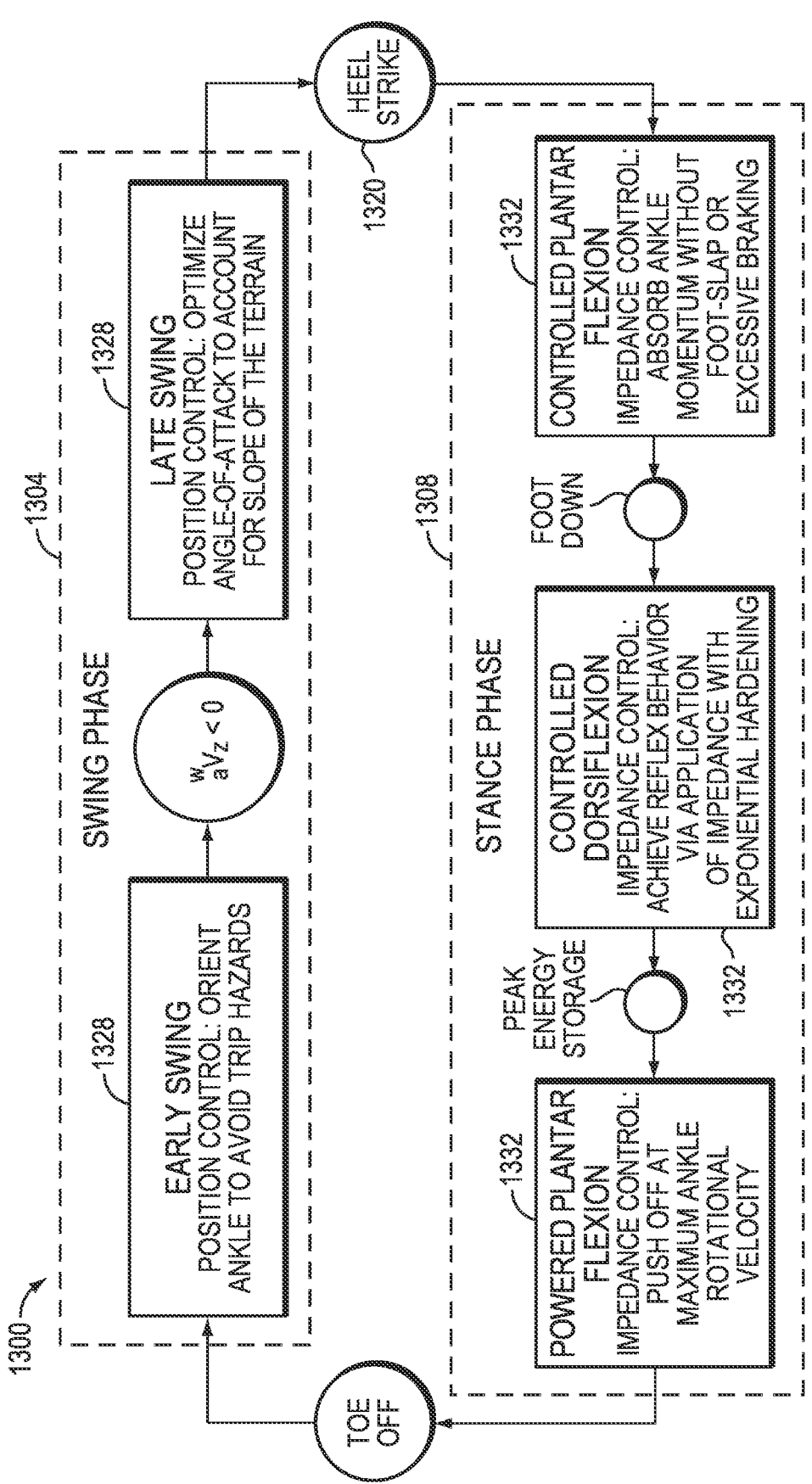
FIG. 13A is a schematic representation of a control system scheme for a heel strike case, according to an illustrative embodiment of the invention.
Figure 13B:
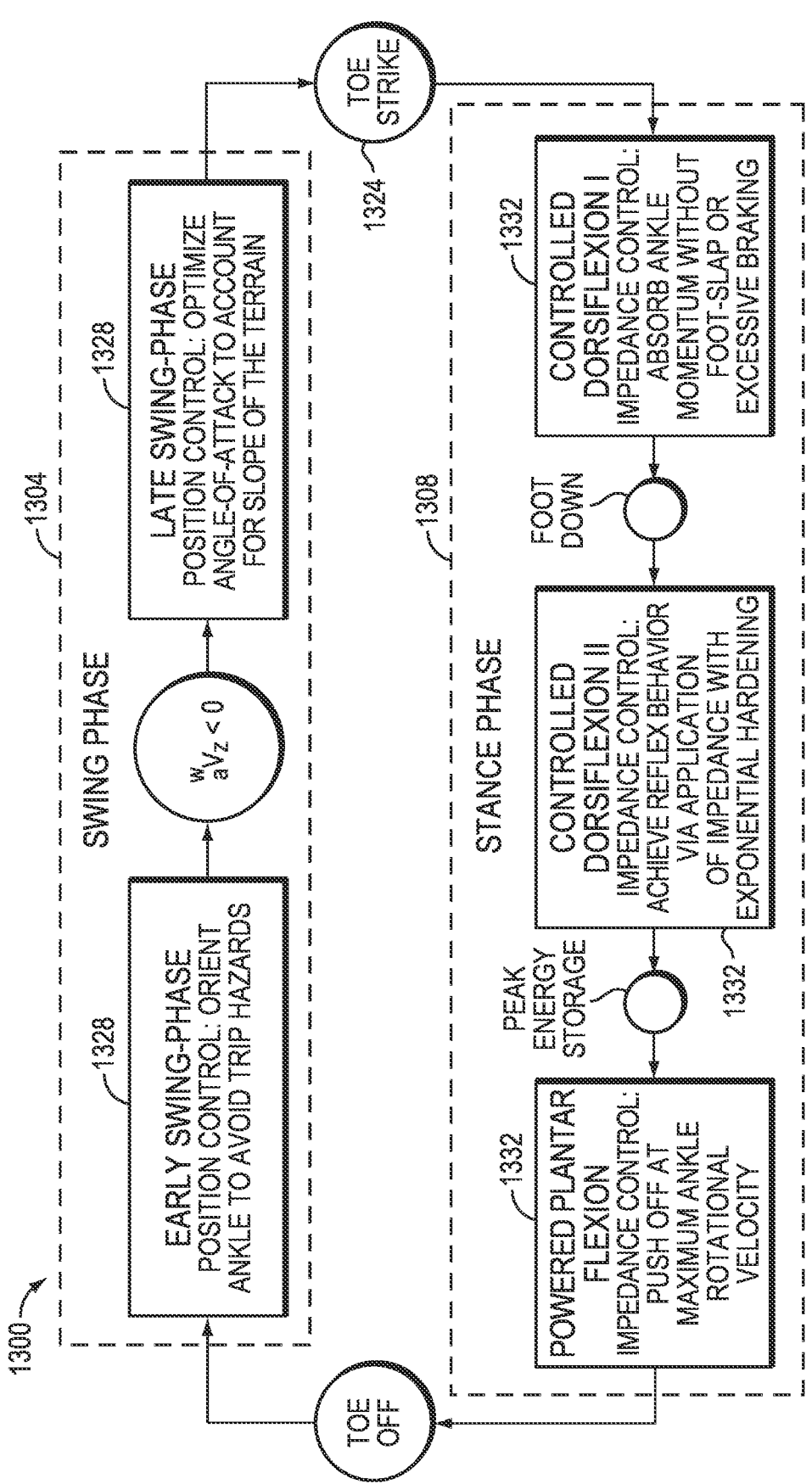
FIG. 13B is a schematic representation of a control system scheme for a toe strike case, according to an illustrative embodiment of the invention.

FIGS. 13A and 13B provide the state control context for an illustrative embodiment of the invention applied to, for example, apparatus 1700 of FIGS. 17A-17E. Normal walking involves the cycling between two phases: the swing phase and the stance phase. FIG. 13A depicts a control system scheme involving a walking motion in which the stance phase, is initiated by the heel striking 1320 the ground. $_a^{w}V_z$ denotes the z-component of the ankle joint velocity in the ground-referenced, world frame. FIG. 13B shows a walking motion in which the stance phase is initiated by the toe striking 1324 the ground.

Exemplary Control System Behavior for Driving Prosthesis or Orthosis Through Gait Cycle FIGS. 13A and 13B illustrate that the control system 1300 changes ankle behavior as the ankle transitions between states in the swing 1304 and stance phases 1308. The control system 1300 applies position control 1328 in the swing phase positioning the ankle so as to avoid trip hazards in the early swing phase state and so as to optimize heel-toe strike attack angle (adaptive ankle positioning) for specific terrain conditions (slope, stairs, steps) in the late swing phase state. The control system 1300 applies impedance and torque control 1332 in the stance phase optimizing the inertial, spring and damping characteristics of the ankle as the ankle transitions through the heel/toe strike, foot down, peak energy storage (dorsiflexion with exponential hardening), powered plantarflexion and toe-off events.

Figure 13C:
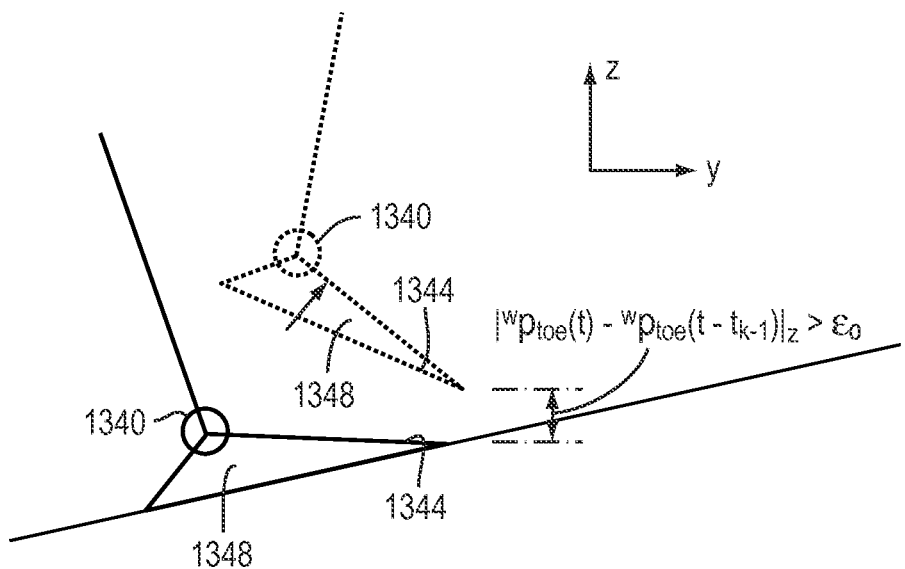
FIG. 13C illustrates a method for position control applied to an ankle prosthesis (e.g., apparatus 1700 of FIG. 17A), according to an illustrative embodiment of the invention.

FIG. 13C illustrates a method for position control applied to a lower limb apparatus (e.g., apparatus 1700 of FIG. 17A), according to an illustrative embodiment of the invention. It is desirable to not move the foot member 1348 forward until the wearer and/or the controller of the apparatus are sure the toe 1344 is going to clear the terrain in front of the wearer. One exemplary way to accomplish this is to wait until the toe 1344 of the foot member 1348 is a sufficient distance above the last known position of the toe 1344 with respect to the underlying terrain. In this embodiment, the control system 1300 applies position control 1328 by beginning to rotate the ankle joint 1340 only after the clearance distance measured along a normal vector to the terrain surface between the toe 1344 of the foot member 1348 at time t and at time $t_{k-1}$ is determined to be greater than ($\varepsilon_0$). This minimizes the risk that the toe 1344 will encounter a trip hazard. In one embodiment, the position of the toe 1344 at the two different times (t and $t_{k-1}$) are determined using the inertial measurement unit measurements, as described previously herein. One skilled in the art would understand how to apply other schemes to determine when it is appropriate to move the foot member 1348 forward. In some embodiments, the controller may determine it is appropriate to move forward based on, for example, whether the swept volume of the foot, when dorsiflexed, achieves the desired clearance relative to the terrain surface.

Figure 14A:
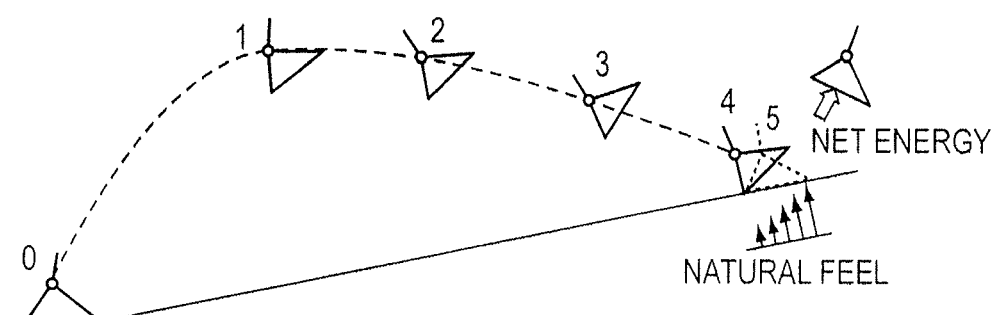
FIG. 14A illustrates a method for employing step-by-step terrain adaptation, according to an illustrative embodiment of the invention.

In summary, this embodiment of the invention, the prosthetic apparatus employs step-by-step terrain adaptation with the intent to achieve true biomimetic behavior in all ambulation task contexts; including level-ground walking, stair ascent/descent and ramp ascent/descent. FIG. 14A outlines the process by which the step-by-step adaptation is accomplished. In the swing phase, the inertial measurement unit supplies the intrinsic sensing input (as opposed to say extrinsic neuronal/myoelectric inputs) that enables the apparatus to discern terrain context from cues supplied by swing-phase trajectory features. Adaptive swing-phase ankle positioning refers to the articulation of the ankle angle, θ, so as to achieve a natural heel or toe touchdown that is optimized for the most likely terrain context as determined by the terrain context discrimination on the swing phase trajectory cues.

Figure 14B:
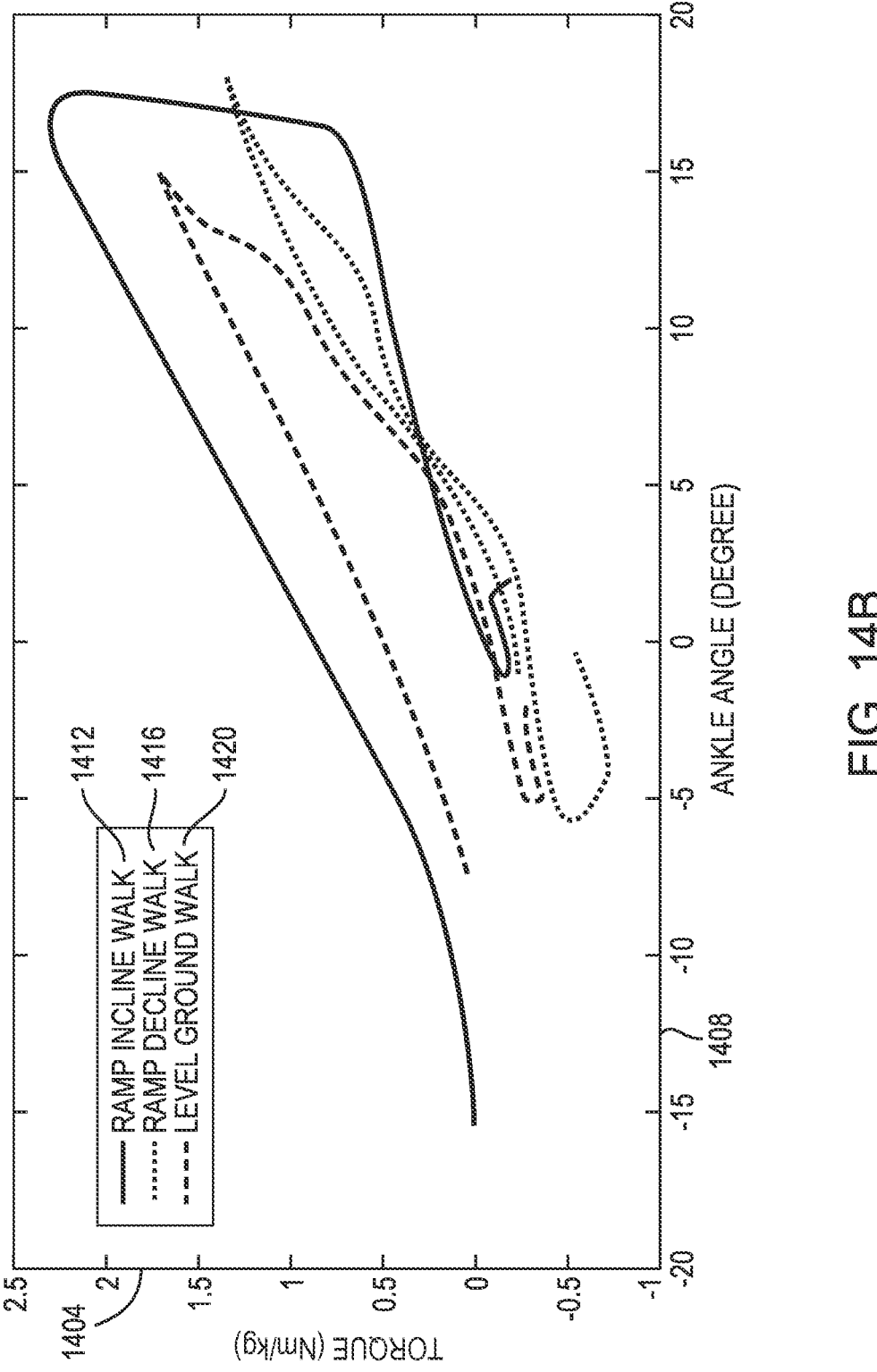
FIG. 14B illustrates exemplary impedance that an ankle joint prosthesis would apply for three different ambulation contexts.

FIG. 14B illustrates exemplary impedance that an ankle joint prosthesis would apply for three different ambulation contexts. FIG. 14B is a graph of required ankle torque 1404 (units of Nm/kg) versus ankle joint angle 1408 (units of degrees). The graph includes three curves 1412, 1416 and 1420. Curve 1412 illustrates the ankle joint torque 1404 versus ankle joint angle 1408 for walking on a ramp incline of 5 degrees. Curve 1416 illustrates the ankle joint torque 1404 versus ankle joint angle 1408 for walking on a ramp decline of 5 degrees. Curve 1420 illustrates the ankle joint torque 1404 versus ankle joint angle 1408 for walking on a ramp incline of 0 degrees (level ground). The slope of the curves is equal to the stiffness (or impedance in general). The area enclosed by the closed Γ-θ curve corresponds to the amount of non-conservative work required for the specific terrain context (e.g., slope, stairs) and walking speed. As can be seen in the graphs, an ankle joint prosthesis would be required to provide more work to accomplish the ambulation task of walking up an inclined ramp versus walking on level ground because the area within the curve 1412 is greater than the area within the curve 1416.

Generalization of the Hybrid Lower-Extremity Augmentation System

Figure 15:
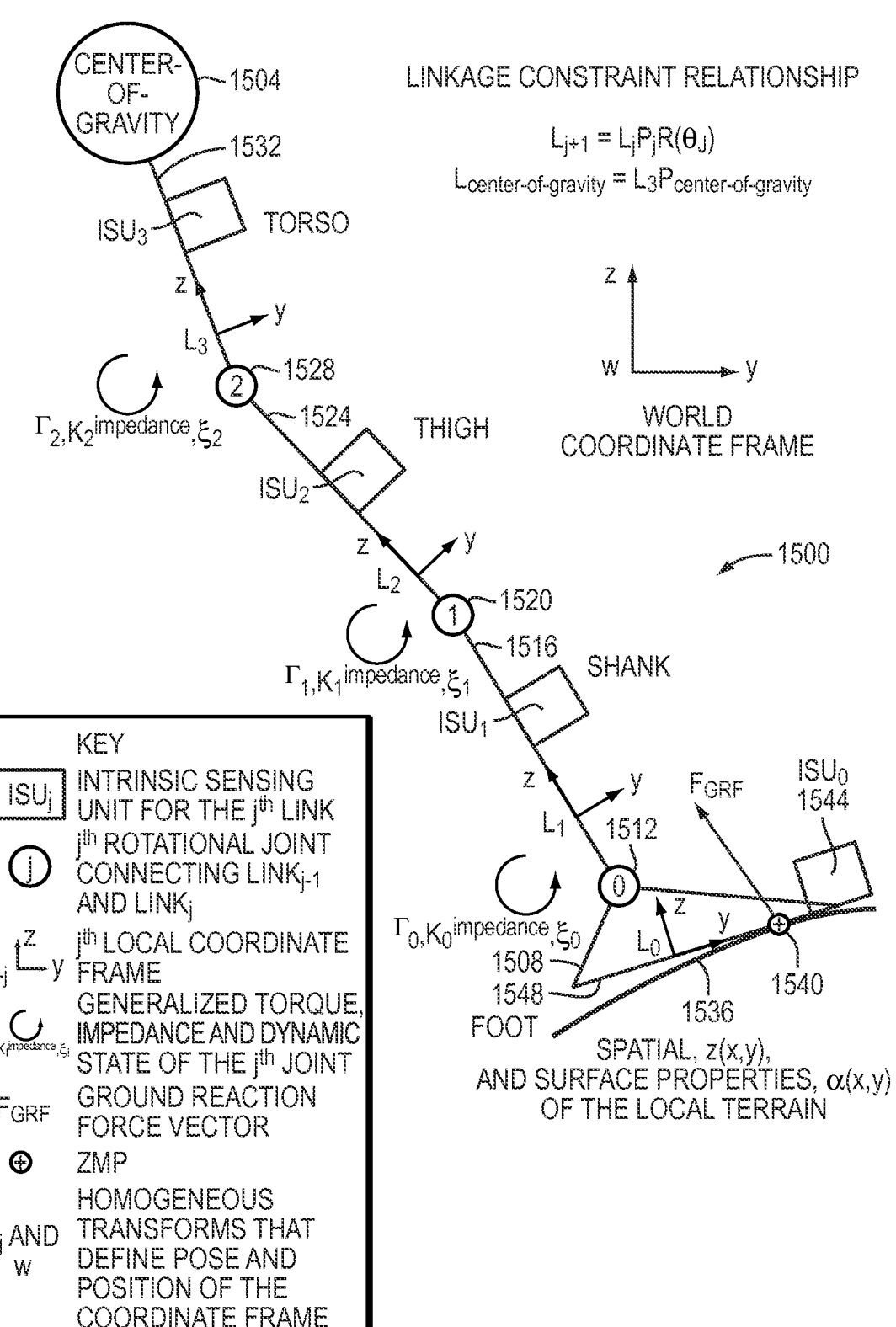
FIG. 15 is a schematic representation of a lower-extremity biomechanical system, according to an illustrative embodiment of the invention.

FIG. 15 is a schematic representation of a lower-extremity biomechanical apparatus 1500, according to an illustrative embodiment of the invention. In one embodiment, the apparatus 1500 is an orthotic apparatus that augments the ambulation abilities of the wearer. In another embodiment, the apparatus 1500 is an orthosis apparatus that attaches to a wearer's body to support and/or correct musculoskeletal deformities and/or abnormalities of a wearer's hip, thigh, lower leg and foot. In another embodiment, the apparatus 1500 is an exoskeleton apparatus that attaches to a wearer's body to assist or augment the wearer's lower-extremity biomechanical output (e.g., augment the lower-extremity strength or mobility of the wearer).

The apparatus 1500 is a linkage represented by a plurality of links (or members) and joints that connect the links. The apparatus 1500 includes a foot member 1508 ($L_0$) coupled to a lower leg member 1516 ($L_1$) by an ankle joint 1512. The apparatus 1500 also includes a thigh member 1524 ($L_2$) coupled to the lower leg member 1516 by a knee joint 1520. The apparatus also includes a hip joint 1528 that couples the thigh member 1524 to the torso 1532 ($L_3$) of the wearer. Center-of-mass 1504 is the center-of-mass of the combination of the apparatus 1500 and the wearer.

The foot member 1508 contacts the terrain 1536 underlying the foot member 1508 at the zero moment pivot 1540. The foot, member 1508 includes a toe portion 1544 and a heel portion 1548. Each joint of the apparatus 1500 also includes an actuator with a generalized vector of torque (force) $\Gamma_i$, displacement $\xi_i$, and impedance $K_i$, where i=0 corresponds to the ankle joint 1512, i=1 corresponds to the knee joint, and i=2 corresponds to the hip joint. Each joint actuator may include a machine element (e.g., ball-screw actuator or rotary harmonic drive), human muscle, or both. Joint displacements typically take the form of angular displacement (rotation) but may also include a combination of linear and angular displacements as found in, for example, a typical knee joint. The pose of a link, i, is represented by a 4×4 matrix that defines the location of the link origin and the unit vectors of its coordinate frame in terms of the unit vectors in the world coordinate frame, W.

The pose of each link, j, can thereby be determined via linkage constraint relationships-specifically by multiplying the pose of link, i–1, by a transformation defined by the generalized displacement, $\xi_j$, and specific link parameters (link length, skew and convergence angles). For example, if the pose of the shank is known, the pose of the foot, thigh and torso can be computed provided that the generalized displacements for those linkages are known, either by directly sensing these or through the use of inertial sensors. The vector of sensor information intrinsic to each link is encapsulated in what we will call an intrinsic sensing unit (ISU). Examples of intrinsic sensors include direct or indirect measurement of generalized displacements; measurement of the angular rate and acceleration of the link (e.g., using, for example, an inertial measurement unit); measurement or estimation of the components of force or torque on the link; multi-modal computer imagery (e.g., a range map) or measurement of the outputs of specific neural pathways on or adjacent to the link.

The terrain is modeled as a contour function, $z(x,y)$, with surface properties, $\alpha(x,y)$. In this context, the surface properties would include the elasticity/plasticity, damping characteristics and coefficient of friction of the surface sufficient to capture the ability of the foot to gain traction on the surface and to capture the surface energy as this would relate to the work required to touch down on the surface and to push off of it with the foot member.

FIG. 16 is a schematic illustration of a method for determining the pose of the thigh member, hip member and torso of a wearer; according to an illustrative embodiment of the invention. In lower-limb systems employing robotic knee prostheses or orthosis, the location of the human hip can also be computed, either by incorporating an inertial measurement unit on the thigh or by measuring the relative knee angle as referenced to the lower leg member. If an inertial measurement unit is further employed on the torso, the pose of the torso can also be instantaneously computed. Alternatively, the pose can be computed by measuring the two degree-of-freedom hip joint displacements. Compensation for the torso pose prediction errors arising from the rate gyro and accelerometer drift on the torso inertial measurement unit can be corrected during the lower leg member zero-velocity update through a chaining of velocity constraints through the hybrid system linkages.

FIG. 16 illustrates a method of pose reconstruction in which j, j–1 velocity constraints are used to correct the prediction of torso ($_{torso}{}^w\hat{T}(t=t_{zvupi})$), thigh pose ($_{thigh}{}^w\hat{T}$ ($t=t_{zvupi}$)) and torso/body center-of-mass pose ($^w v_{cg}$ ($t=t_{zvupi}$)). Step 1 (1604) captures the output of the zero velocity update on the lower leg member 1620 (link 1) to determine the lower leg member pose, as described above with respect to FIGS. 2A-5. The solutions (steps 2 and 3) for the thigh member 1624 (link 2) and torso member 1628 (link 3), respectively, follow the example of step 1 (1604), but in these cases the velocity constraints are non-zero and are predicted by the translational and rotational velocity from the prior link.

Exemplary Mechanical Designs

FIG. 17A is an illustration of a lower-extremity prosthetic apparatus 1700, according to an illustrative embodiment of the invention. The apparatus 1700 has a mounting interface 1704 making it capable of attaching to a complementary lower-extremity limb socket member of a wearer. The apparatus 1700 also includes a structural element 1732 (also referred to herein as the pyramid) coupled to the mounting interface 1704 and a first end 1752 of a lower leg member 1712 (also referred to herein as a shank). In some embodiments, the axial force and moment applied to the lower leg member of the apparatus is determined based on sensor measurements made using the structural member (pyramid) coupled to the lower leg member of the apparatus. The pyramid is an instrumented structure that is a component of the prosthesis and which couples to the limb socket of the wearer. In one embodiment, the pyramid (structural element) measurements are used by a controller to determine axial force and moment applied to the lower leg member. In this embodiment, the structural element 1732 is coupled to the first end 1752 of the lower leg member 1712 with a set of pins 1711. The pins 1711 pass through a set of holes 1713 in the lower leg member 1712 and a set of holes 1715 (shown in FIG. 17E) in the structural element 1732.

The structural element 1732 has a top surface 1731 located towards the mounting interface 1704 and a bottom surface 1733 located towards the lower leg member 1712. The lower leg member 1712 is also coupled to a foot member 1708 at an ankle joint 1740 at a second end 1744 of the lower leg member 1712. The ankle joint 1740 (e.g., a rotary bearing) permits the foot member 1708 to rotate about the x-axis relative to the lower leg member 1712. The foot member includes a heel 1772 and a toe 1776.

The apparatus 1700 also includes a linear actuator 1716 with a first end 1736 and a second end 1748. The linear actuator 1716 generates a linear motion 1703. The first end 1736 of the linear actuator 1716 is coupled (with, for example, a rotary bearing) to the first end 1752 of the lower leg member 1712. The apparatus 1700 also includes a first passive elastic member 1728 in series with the linear actuator 1716. The passive elastic member 1728 is coupled to the foot member 1708 and the second end 1748 of the linear actuator 1716. The passive elastic member 1728 is coupled to the foot member 1708 (with, for example, a rotary bearing) at the proximal end 1730 of the passive elastic member 1728. A distal end 1726 of the passive elastic member 1728 is coupled between the second end 1748 of the linear actuator 1716 (with, for example a rotary bearing). The linear actuator 1716 applies torque about the ankle joint 1740.

The apparatus 1700 also includes an optional second passive elastic member 1724 with a first end 1756 and a second end 1760. The second passive elastic member 1724 provides a unidirectional spring force in parallel (provides parallel elasticity) with the lower leg member 1712. The first end 1756 of the second passive elastic member 1724 is coupled to the first end 1752 of the lower leg member 1712. The second end 1760 of the second passive elastic member 1724 is coupled to the foot member 1708. However, during plantarflexion the spring is not engaged, and therefore only provides a unidirectional spring force to the apparatus.

In some embodiments, the second passive elastic member 1724 is a non-compliant stop that stores little or no energy and limits further rotation of the ankle beyond a predefined angle during powered plantar flexion.

FIGS. 17B and 17C are illustrations of a portion of the lower extremity apparatus of FIG. 17A depicting the second passive elastic element 1724. The second passive elastic element 1724 stores energy during dorsiflexion but, not in plantarflexion. The elastic element 1724 has a double-cantilever engagement (clamped at a location 1780 between the first end 1756 and the second end 1760). The elastic member 1724 has a tapered shape 1784 that causes the elastic member 1724 to provide efficient energy storage by maximizing bending strain along the entire length (along the y-axis) of the elastic element 1724. In some embodiments, the normalized spring constant ranges from 0-12 Nm/rad/kg. At the high end of the range, the energy storage is approximately 0.25 J/kg.

A cam/ramp arrangement of the elastic member 1724 facilitates tailoring of the spring constant to the weight of the wearer. The cam element 1788 is located at the second end 1760 of the elastic member 1724. The ramp element 1792 is located on the foot member 1708. The cam element 1788 engages the ramp element 1792 during dorsiflexion; however, the cam element 1788 does not engage the ramp element 1792 or another portion of the apparatus 1700 during plantarflexion. Because the cam element 1788 does not engage the ramp element 1792 or another portion of the apparatus 1700 during plantarflexion, the elastic member 1724 stores energy only during dorsiflexion. In one embodiment, the position of the ramp element 1792 is screw-adjustable to allow the wearer or a second party to tailor the ramp engagement of the cam element 1788 so as to align the energy storage characteristics to the wearer's walking habits. An operator may adjust the position of the ramp element 1792 relative to the position of the cam element 1788 in order to modify the energy storage characteristics of the passive elastic member 1724.

In alternative embodiments, an actuator is integrated into the ramp to adjust the ankle joint angle at which the second passive elastic member 1724 (elastic member engagement angle) engages. This would enable the ankle joint 1740 to be dorsiflexed during the swing phase without engaging the elastic member 1724 when, for example, the wearer is ascending ramps and stairs, and while running.

The passive elastic element 1724 also functions to increase the frequency response of the apparatus 1700 when the elastic element 1724 is engaged in dorsiflexion. The apparatus 1700 dynamics in dorsiflexion benefit from a fast response (bandwidth) series elastic actuator (i.e., combination of the linear actuator 1716 and first passive elastic element 1728). The spring constant associated with the second passive elastic element 1724 increases the bandwidth of the apparatus 1700 by a factor, β, where:

$$\beta = (K_3 + K_s/K_3)^{1/2}/K_s)^{1/2}| \qquad \text{EQN. 34}$$

where $K_3$ is the spring constant of the second passive elastic member 1724 and $K_s$ is the spring constant of the combination of the linear actuator 1716 and first passive elastic element 1728. In one embodiment of the invention, the second passive elastic element provides a β from 1 to 3;

thereby increasing the bandwidth of the apparatus 1700 from about 5 Hz to about 15 Hz.

The second passive elastic member 1724 employs a dovetail feature 1796 at both ends to enable clamping at both ends without use of mounting holes. In one embodiment, the second passive elastic member 1724 is fabricated from composite fiber materials. Mounting holes would form a stress intensity and cause fiber dislocations in the passive elastic member 1724 that would compromise the strength of the spring. The end clamps 1798 have complementary shapes that hold the passive elastic element 1724 in place. In one embodiment of the invention, epoxy is employed in the clamps to permanently secure the second passive elastic member 1724 in the end clamps. The epoxy joint would be more prone to failure in the absence of the dovetail features 1796.

The passive elastic element 1724 employs a tapered design to maximize energy storage in the element 1724 to ensure that energy storage density is constant over its length for a given deflection. Referring to FIG. 17D, we illustrate the free-body diagram for the passive elastic element 1724, showing how the roller force, $F_{roller}$, and the lower leg member force, $F_{shank}$, combine to create an equal and opposite force by the central pivot. In this embodiment, the roller force and the lower leg member force are applied equidistant from the center pivot. The forces at the end, F, combine to create a central pivot force of 17F. Using standard thin beam relationships, the moment acting at a distance of x from the central pivot varies linearly-starting at a value of FL in the center and falling to zero at x=L, where L is the length of the passive elastic element 1724 between the locations at which the forces are applied. Energy storage density along x is proportional to the product of moment (M(x)) and the strain at the surface ($\varepsilon_0(x)$), where:

$$M(x) = F\left(\frac{L}{2} - x\right) \qquad \text{EQN. 35}$$

$$\epsilon_0(x) = \frac{M(x)}{EI\omega^*} = \frac{F\left(\frac{L}{2} - x\right)}{EI\omega^*} \qquad \text{EQN. 36}$$

For a given layup of composite material, the surface strain is kept below a critical value, $\varepsilon^*$ For a given moment, the energy density in the beam will be maximized when the surface strain is set to this critical value. To keep the energy density constant and at its maximum value, the optimal width of the beam, w*(x), is defined by the relation:

$$w^* = w^*(x) = \frac{F}{EI\epsilon_0^*}\left(\frac{L}{2} - x\right) \qquad \text{EQN. 37}$$

In one embodiment, the taper 1784 varies linearly from the center of the beam. By using this design method, we have amplified the energy storage of the spring by over a factor of 2 when compared to a beam without a taper 1784. Because the composite spring material is not homogeneous and since the thin beam equations are not applicable, computational tools are used to estimate the energy storage density in the passive elastic member 1724. The shape that is able to store the most energy is highly dependent upon the fiber laminate, lamination design, thickness and the exact manner in which the passive elastic member 1724 is attached to the apparatus 1700. We have determined, however, that a linear taper delivers energy storage within about 10% of the optimal. In a preferred embodiment, the linear taper is used because of the relative ease by which a linear taper pattern maybe cut from a sheet of laminated ply composite material using a water-jet process. In alternative, less preferred embodiments, a non-tapered spring may be used.

FIG. 17E is an illustration of a perspective view of an embodiment of the structural element 1732 (also referred to herein as the pyramid). The structural element 1732 is coupled between the mounting interface 1704 and the first end 1752 of the lower leg member 1712. The structural element 1732 is coupled to the first end 1752 of the lower leg member 1712 with a set of pins 1711 (shown in FIG. 17A). The pins 1711 pass through the set of holes 1713 in the lower leg member 1712 and a set of holes 1715 in the structural element 1732. The pins 1711 allow a rotary degree of freedom for the strain in structural element 1732 from being falsely recorded as axial force and moment in the structural element 1732. In this embodiment, the structural element 1732 is capable of measuring the moment and axial load on the ankle joint 1740, enabling, for example, positive detection of "foot-down" for use by the controller 1762 state machine that controls the apparatus 1700 functions; measurement of applied moment for use by the positive-feedback reflex controls employed during powered plantarflexion; and positive detection of tripping for use by a safety system integrated into the controller 1762.

In this embodiment, the structural element 1732 is designed as a flexural element that amplifies the strain fields induced by the medial-lateral moment and axial force applied to the apparatus 1700 during operation. The structural element 1732 creates high magnitude strain fields of opposite sign (differential strain fields) in the regions 1738 and 1742 about the center adaptor mounting hole 1734 when a medial-lateral moment (moment about the x-axis) is applied. These differential strain fields are not present when only an axial force is applied. The structural element 1732 includes one strain gage (1782 and 1786) bonded to each of the two moment-sensitive regions (1738 and 1742, respectively) on the bottom surface 1733 of the structural element 1732. The gages are applied on opposing sides of a Wheatstone bridge. The controller 1762 is coupled to the Wheatstone bridge to measure the strains. The strain measurements are used to measure moment on the structural element 1732. In one embodiment, the sensitivity of the measurement is approximately in the 0.15 N-m range, where, in this context, sensitivity defines the minimum resolvable change (signal to noise$\cong$1) when digitally sampled at 500 Hz.

In contrast to the moment induced strains, high strains are introduced by axial forces along the medial-lateral axis in the regions 1746 and 1754 around the center adaptor mounting hole 1734. These strains appear in a 0.76 mm thickness region (regions 1746 and 1754) under the slots (1758 and 1770, respectively) machined along the medial-lateral axis. The section above the slot must be thick enough to transfer moment load with minimum strain in the thin lower section. The strain magnitude is significantly diminished in the thin section when a moment-only load is applied. The structural element 1732 includes one strain gage (1790 and 1794) bonded to each of the two axial load-sensitive regions (1746 and 1754, respectively) on. the bottom surface 1733 of the structural element 1732. The gages are applied on opposing sides of a Wheatstone bridge. The controller 1762 is coupled to the Wheatstone bridge to measure the strains. The strain measurements are used to measure axial force on the structural element 1732, and consequently, axial force on the lower leg member 1712. The machined slots 1758 and 1770 amplify the axially-induced strains without compromising the structural integrity of the structural element 1732.

Since the structural element 1732 is in the critical chain of structural support between the residual limb socket of the wearer (not shown) and the apparatus 1700, in one embodiment it is preferably designed to withstand more than 60 N/kg of axial load: In this embodiment, the sensitivity of the axial measurement is in the range of approximately 50 N, which is well below the approximately 100 N threshold normally used in the apparatus 1700 to sense that the apparatus has been placed firmly on the ground. During calibration of the apparatus 1700 a 2×2 sensitivity matrix is determined, enabling true moment and axial force to be derived from the pairs of strain measurements.

Figure 17F:
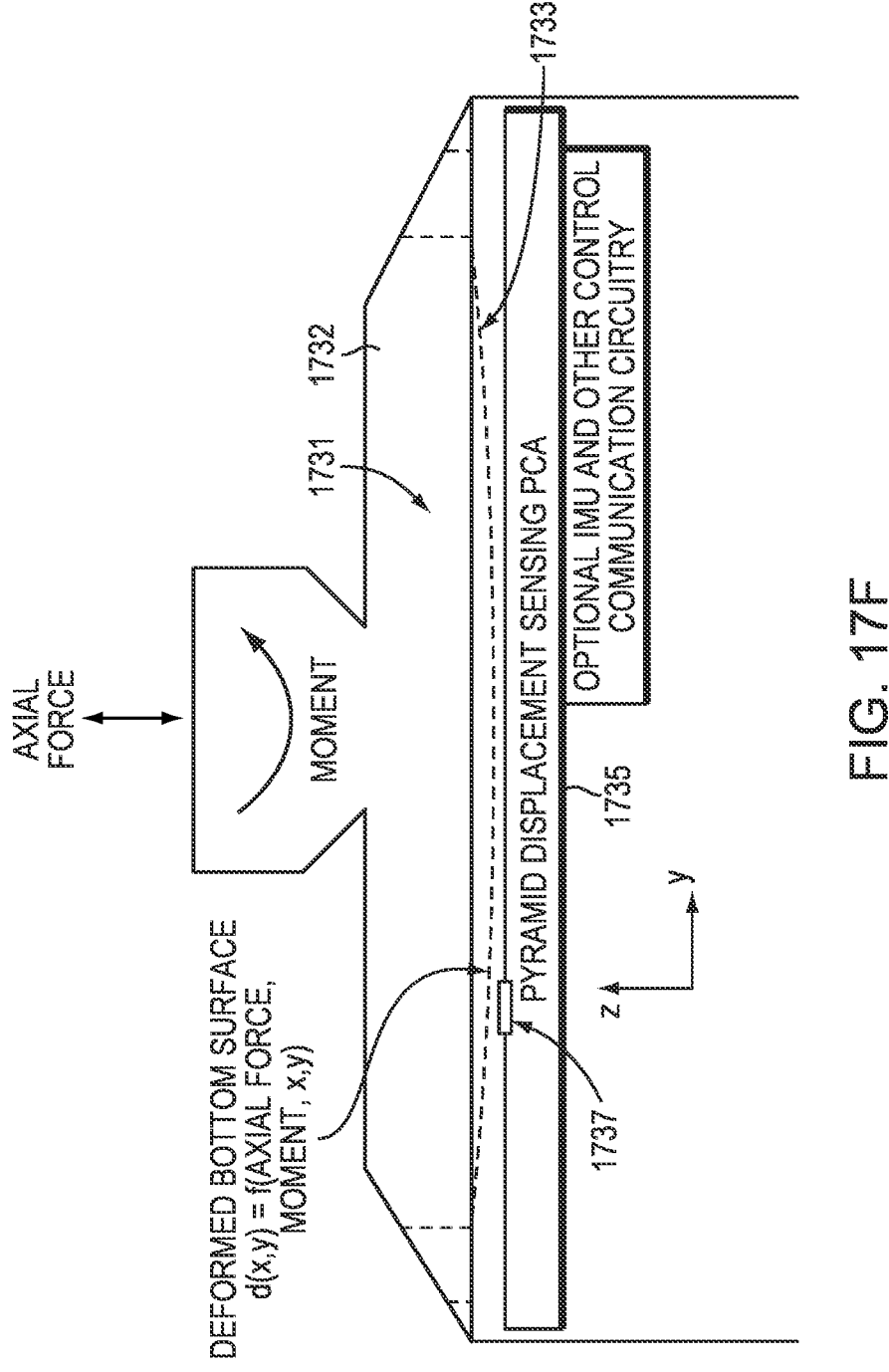
FIG. 17F is an illustration of a cross-sectional view of an alternative method for measuring axial force and moment applied to the lower leg member of FIG. 17A, according to an illustrative embodiment of the invention.

FIG. 17F is an illustration of a cross-sectional view of an alternative method for measuring axial force and moment applied to a lower leg member, according to an illustrative embodiment of the invention. In this embodiment, the structural element 1732 employs a flexural design that amplifies displacement of its bottom surface 1733 in such a way that the axial force and in-plane moment (two-degrees of freedom) can be derived in a redundant fashion. In this embodiment, the apparatus 1700 includes a displacement sensing apparatus 1735 for measuring deflection of the structural element 1732 to determine the. moment (torque) and axial force applied to the lower leg member 1712.

In this embodiment, the displacement sensing apparatus 1735 includes a printed circuit assembly (PCA) employing one or more displacement sensors 1737 (e.g., contact or non-contact displacement sensors). The sensors measure, at each sense coordinate, the distance between the sensor 1737 and the bottom surface 1733 of the structural element 1732.

In one embodiment, changes in mutual inductance of coils printed on the PCA with respect to the bottom surface 1733 of the structural element 1732 are used to measure the local surface deformation (displacement). In this embodiment, counter-circulating "eddy" currents in the structural element I 732 serve to reduce the coil inductance inversely with the distance between the coil and the bottom surface 1733 of the structural element 1732. Other displacement sensing technologies could be employed, including non-contact capacitance and optical sensors or contact-based sensors that employ force-sensitive resistors, piezo or strain-gages integral to the PCA. By sampling the array of displacement sensors, the axial force and moments can be estimated using a sensitivity matrix that is computed during an off-line calibration process.

In this embodiment, the structural element 1732 is fastened to the lower leg member 1712 with screws, eliminating the need for the pins 1711 employed in the embodiment illustrated in FIG. 17E. The screw fastening method reduces weight and manufacturing complexity. Furthermore, this fastening method amplifies displacements measured in the center of the structural element 1732 where the displacement sensing apparatus 1735 is located. FIG. 17G illustrates how the in-plane moment vector and axial force may be computed using a circular array of displacement sensors on the printed circuit assembly. As shown, demodulation of the bias and sinusoidal-like displacement function is used to estimate the moment and force. Other displacement sensor array configurations could be used as a means of intrinsic sensing of moment and force.

Moment and force sensing is useful as a means of signaling walking state changes. In addition, measurement of lower leg member 1712 moment serves as a feedback means by which reflexive behavior is achieved in powered plantarflexion. When combined with inertial and actuator feedback, the intrinsic moment and force measurements are used to calculate ground reaction force and zero moment pivot, which are useful for traction control and balance. For these reasons, it is beneficial to package the intrinsic moment and force sensing with the inertial measurement unit and state control processing functions. FIG. 17F shows how these functions could be implemented on a PCA. Such a PCA could be implemented as a sandwich of FR-4 material with a stable core material (Invar for instance) serving as a stiff interposing substrate between the top-side displacement sensing FR4-based layer and a bottom FR-4-based layer that incorporates the signal processing layer. Integrating the materials and functions in a single assembly eliminates the need for cabling and other potentially unreliable means for interconnecting these functions. Such integration also allows for a stand-alone tool that can be used by prosthetists to setup a passive prosthetic and study, gait parameters, including energy return and walking statistics Referring to FIG. 17A, the apparatus 1700 also includes a controller 1762 coupled to the linear actuator 1716 for controlling the linear actuator 1716. In this embodiment, the controller is located within a housing 1764 of the apparatus 1700 to protect it from the environment. A battery 1768 in the housing 1764 provides power to the apparatus (e.g., the controller 1762 and various sensors associated with the apparatus 1700).

The apparatus 1700 includes an inertial measurement unit 1720 to predict the inertial pose trajectory of the ankle joint 1740, heel 1772 and toe 1776 relative to the previous toe-off position. The inertial measurement unit 1720 is electrically coupled to the controller 1762 and provides inertial measurement signals to the controller 1762 for controlling the linear actuator 1716 of the apparatus 1700. In one embodiment, the inertial measurement unit 1720 employs a three-axis accelerometer and a three-axis rate gyro. The three-axis accelerometer measures local acceleration along three orthogonal axes. The three-axis rate gyro measures angular rotation about three orthogonal axes. Through use of well-established methods of numerical integration, the position, velocity and pose of any point on the foot structure can be computed.

In some embodiments, the inertial measurement unit 1720 is used to detect the terrain slope and the presence of steps and stairs thereby enabling optimization of the foot's "angle-of-attack" relative to the underlying terrain prior to touch-down and the ankle joint's spring equilibrium position in the stance phase. In some embodiments, the inertial measurement unit 1720 is used to determine ambulation speed of the wearer and conditions of the terrain (features, texture or irregularities of the terrain (e.g., how sticky is the terrain, how slippery is the terrain, is the terrain coarse or smooth, does the terrain have any obstructions, such as rocks)). This enables the wearer to walk confidently on all terrain types. The inertial pose comprises the three degree-of-freedom orientation of the lower leg member 1712 in a fixed ground-referenced (world) coordinate frame often captured as the orientation component of a homogeneous transformation (three unit vectors defining the x, y and z axes in the world reference frame) or as a quaternion; the translation of the ankle joint 1740 in the world frame; and the velocity of the ankle joint 1740 in the world frame. In this embodiment, the inertial measurement unit 1720 is physically coupled to the lower leg member 1712. In some embodiments, the inertial measurement unit 1720 is coupled to the foot member 1708 of the apparatus 1700.

Figure 17H:
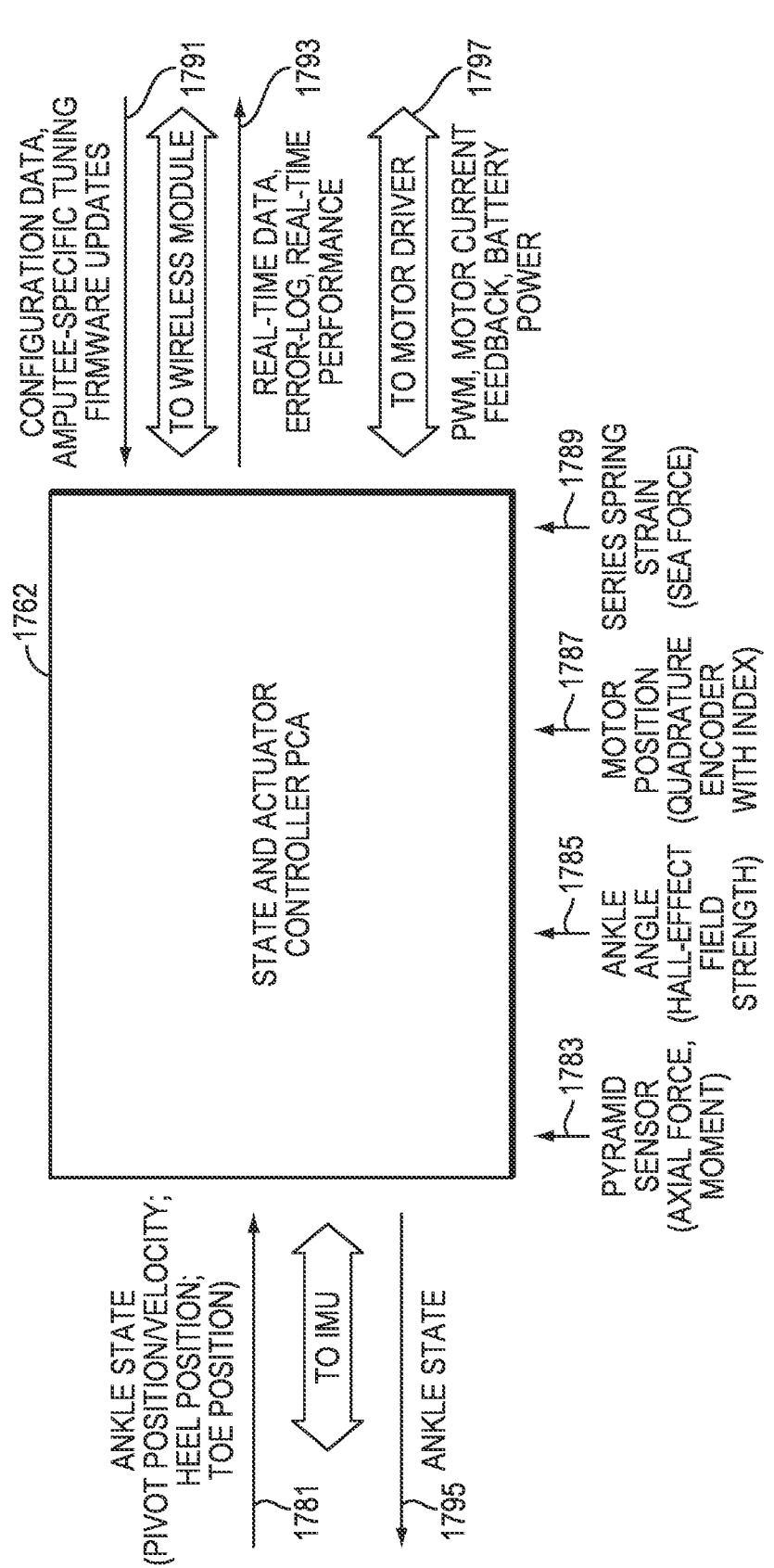
FIG. 17H is a schematic illustration of a state and actuator controller for use with the apparatus of FIGS. 17A-17G, according to an illustrative embodiment of the invention.

FIG. 17H is a schematic illustration of a state estimation and actuator controller (state and actuator control PCA SAC) for use with the apparatus of FIGS. 17A-17G, according to an illustrative embodiment of the invention. In this embodiment, the controller 1762 employs dual 40 MHz dsPIC (manufactured by Microchip™) processors to control and coordinate linear actuator 1716 (e.g., rotary motor of FIGS. 20A and 20B) and the inertial measurement unit 1720. In this embodiment, space-vector modulation is employed to implement the brushless motor control to create an optimum pulse width modulated drive that maximizes motor RPM. Space vector modulation is a PWM control algorithm for multi-phase AC generation, in which a reference signal is sampled regularly. PWM of a signal or power source involves the modulation of the three-phase motor winding voltage duty cycles (e.g., the rotary motor 2004), After each sampling of the reference signal, non-zero active switching vectors adjacent to the reference vector and one or more of the zero switching vectors are selected for the appropriate fraction of the sampling period in order to synthesize the reference signal.

Figures 18A, 18B:
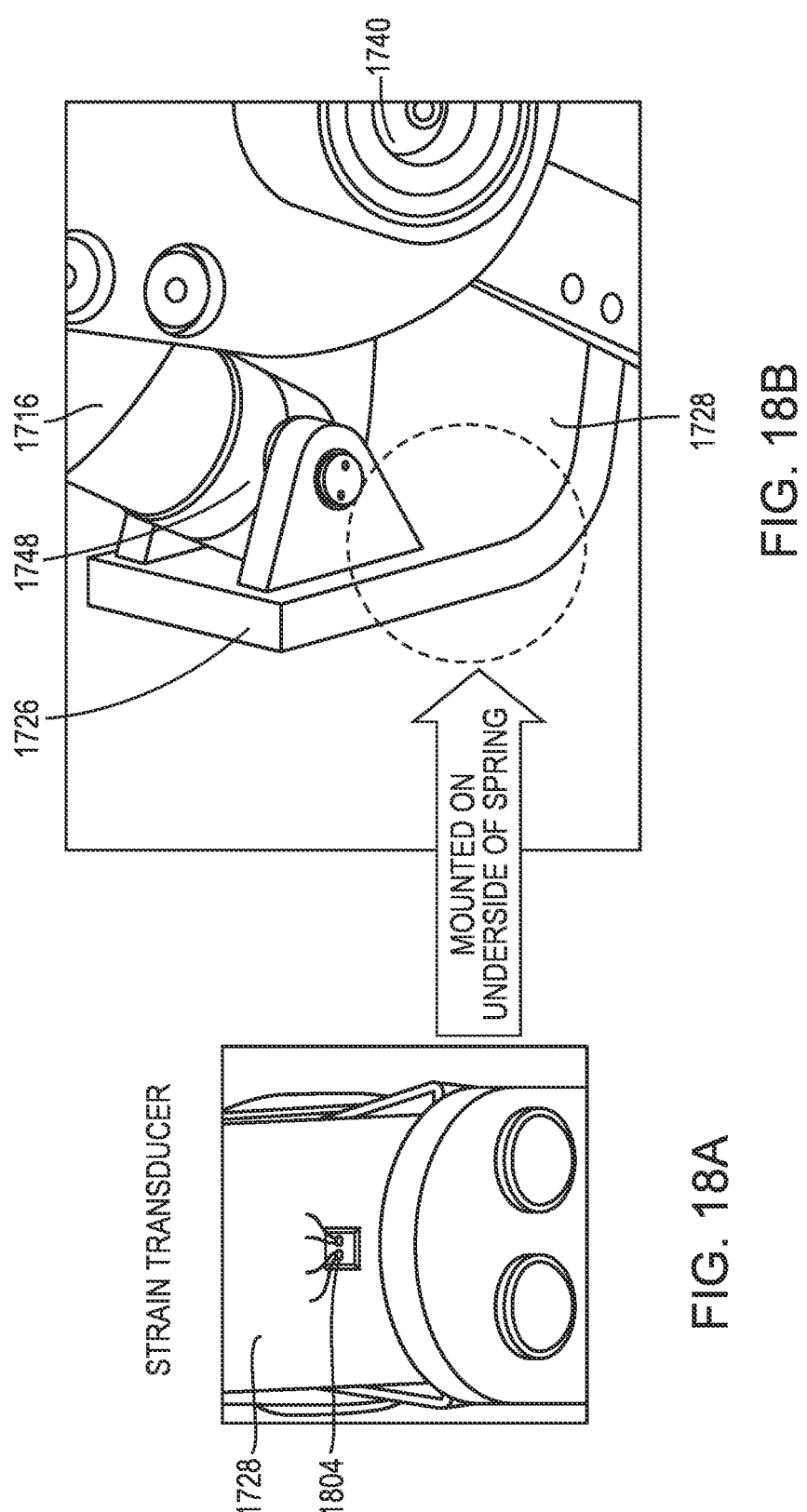
FIGS. 18A-18D are illustrations of a passive series-elastic member, according to an illustrative embodiment of the invention.

The controller 1762 receives a variety of input signals, including, inertial pose signals 1781 from the inertial measurement unit 1720, torque and axial force signals 1783 from the structural element 1732 strain measurements, ankle joint angle signals 1785 from a hall-effect transducer located in the ankle joint 1740, motor position signals 1787 (quadrature encoder with index and absolute motor position) from the encoder (e.g., encoder 2040 of FIG. 20A), strain signals 1789 from the strain sensor 1804 (referring to FIG. 18A) of the series elastic member 1728, and controller parameters 1791 (e.g., apparatus configuration data, wearer-specific tuning, firmware updates)). In addition, the controller 1762 outputs a variety of signals, including, apparatus performance data 1793 (e.g., real-time data, error log data, real-time performance data), ankle state updates 1795. In addition, the controller 1762 outputs commands to the linear actuator 1716 and receives actuator feedback signals from the linear actuator 1716 (generally signals 1797), for example, three-phase pulse width modulation signals provided to the power electronics for the linear actuator 1716, battery power to the linear actuator 1716, and current feedback measurements and temperature measurements from the linear actuator 1716.

This embodiment uses the sensor feedback to identify state changes as the apparatus 1700 transitions through the stance-phase and swing-phase states. By using the redundant and diverse sensor measurements, it also identifies fault conditions and drives the apparatus 1700 into an appropriate safe state. Using an on-board real-time clock, it time-tags the faults and stores these into an on-board e²PROM (error log). The contents of the error log are retrieved wirelessly by the prosthetist and/or manufacturer service personnel. In this embodiment, the Motor Driver PCA (MD) takes pulse-width modulation (PWM) commands from the SAC PCA to switch current into the motor windings. The MD passes sensed current and power information back to the SAC PCA so that it can apply closed-loop control.

In this embodiment, the IMU PCA is mounted nominally in the Sagittal plane (a local plane parallel to the front of the tibia) and employs a three-axis accelerometer, a dual-axis rate gyro ($\omega_z$ and $\omega_x$) and a single-axis rate gyro ($\omega_y$). In this embodiment, a coordinate frame definition is used that defines the y-axis as forward, z-axis as up and x-axis defined as the cross-product of they and z axes (y×z). The IMU receives state information from the SAC at the system sampling rate of 500 Hz. It transmits the ankle state vector—specifically the position and velocity of the ankle pivot, the position of the heel and the position of the toe—all with respect to the foot-flat position from the previous step.

Figure 17I:
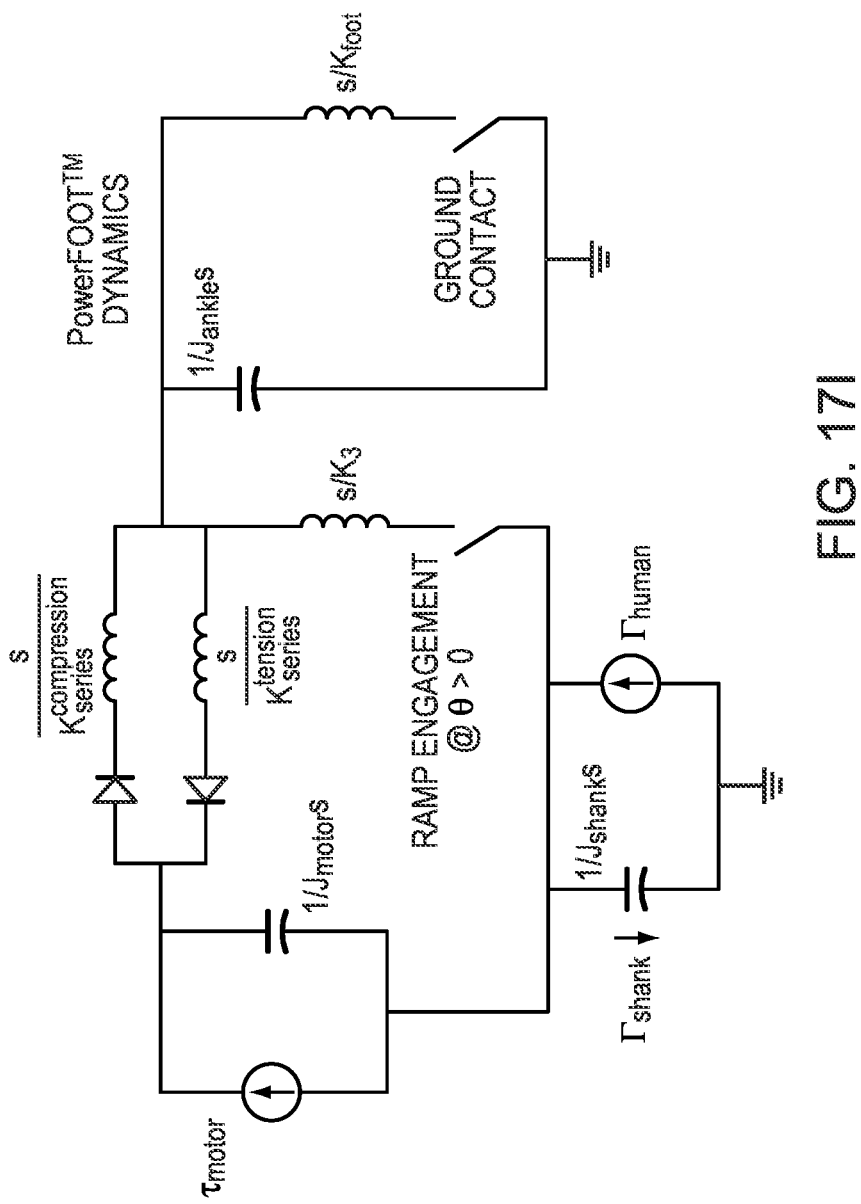
FIG. 17I is a schematic illustration of an electrical circuit equivalent of a lower extremity prosthetic apparatus, according to an illustrative embodiment of the invention.
Figure 17J:
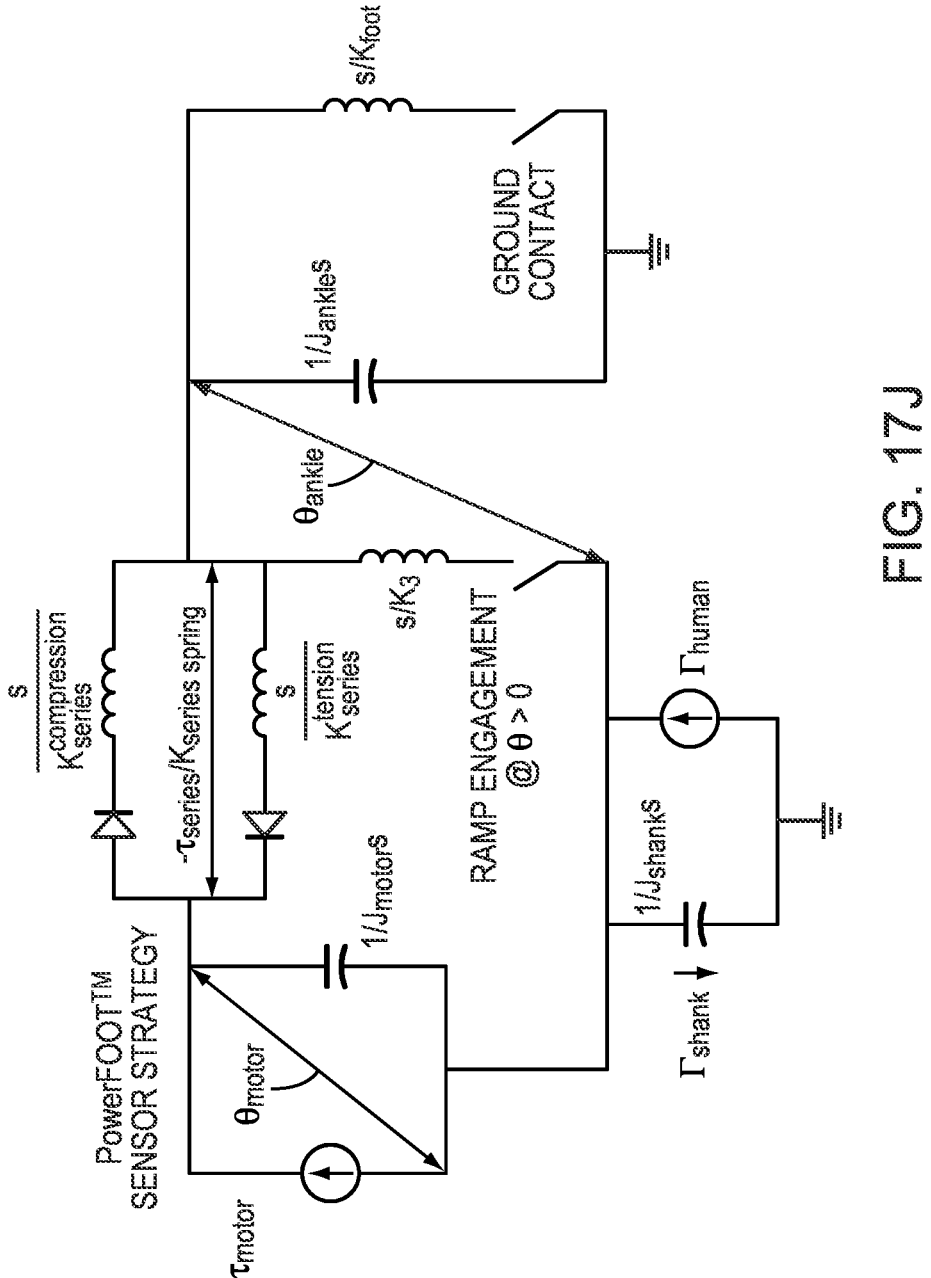
FIG. 17J is a schematic illustration of the electrical circuit of FIG. 17I including sensor measurements used in controlling the apparatus.

FIGS. 17I and 17J are schematic illustrations of an exemplary electrical equivalent of apparatus 1700 of FIG. 17A. Electrical circuit symbols are used to describe the mechanical elements a resistor denoting a mechanical component with damping torque that is linear with velocity; a capacitor denoting a mechanical component with rotary inertia properties; and an inductor denoting a mechanical component with linear spring qualities. With this circuit notation, current corresponds with torque and voltage corresponds with angular velocity.

The circuit components are defined as follows: $J_{shank}$ is the unknown equivalent inertia of the lower leg member (shank) and residual limb below the knee (e.g., inertia of lower leg member 1712 of FIG. 17A); $J_{Motor}$ is the equivalent motor and ball-screw transmission assembly inertia (e.g., inertia of linear actuator 1716 of FIG. 17A); $K_{series}^{compression}$ is the torsional spring constant for the series spring (e.g., passive elastic element 1728 of FIG. 17A) when in compression; $K_{series}^{tension}$ is the torsional spring constant for the series spring when in tension; $K_3$ is the torsional spring constant for the unidirectional parallel spring (e.g., passive elastic member 1724 of FIG. 17A); and $J_{Ankle}$ is the rotary inertia of the foot structure below the ankle (e.g., foot member 1708 of FIG. 17A). The current (torque) sources within the model are defined as follows: $\Gamma_{Human}$ is the unknown torque applied by the wearer's body onto the lower leg member (e.g., lower leg member 1712); $\tau_{motor}$ is the torque applied by the actuator (e.g., linear actuator 1716); and $\Gamma_{shank}$ is the torque measured using the structural element (e.g., structural element 1732 of FIGS. 17A and 17E).

FIG. 17I illustrates the importance of the series and parallel springs as energy storage elements. Use of the stored energy reduces the power consumption that would otherwise be required by the linear actuator. In addition, an additional purpose of the $K_3$ spring is its function as a shunt across the ankle inertia that increases the ankle-spring resonance.

FIG. 17J illustrates how sensors have been employed in this embodiment to provide high-fidelity position and force control, and to achieve the sensor redundancy and diversity desirable for delivering an inherently safe design. As shown, the ankle joint position, $\hat{\theta}$, is derived from the following:

$$\hat{\theta} = \theta_{motor} - \frac{F_{series}}{K_{series}} \qquad \text{EQN. 38}$$

where $$K_{series} = \begin{cases} K_{series}^{compression}, & \text{if } \Gamma_{series} \geq 0 \\ K_{series}^{tension}, & \text{if } \Gamma_{series} < 0 \end{cases} \qquad \text{EQN. 39}$$

A redundant measure of $\theta$ is achieved through use of a Hall-effect angle transducer, thereby providing a verification that the ankle is being manipulated properly by the control system. In one embodiment, the Hall-effect transducer includes a Hall-effect device located on the SAC PCA in the housing 1764 of the apparatus 1700. The transducer also includes a magnet coupled to the foot member 1708. The field effect magnitude (signal output by the transducer) changes in a known way in response to angle joint rotation (i.e., motion of the magnet relative to the Hall-effect device). The Hall-effect transducer is calibrated during manufacturing of the apparatus 1700 by, for example, measuring the output of the transducer to known displacements of the Hall-effect device relative to the magnet. In other ankle angle measurement embodiments, the mutual inductance measured on a coil on the lower leg member has a known relationship as a function of ankle angle, and the inductance can be calibrated to compute angular displacement in a way that is not sensitive to the magnetic fields generated by the motor in the linear actuator or by other stray fields. Also, as shown in FIG. 17J, the ankle moment as applied by the wearer is also measured. This enables the linear actuator to adapt (e.g., to increase stiffness) to achieve reflex behavior.

FIGS. 18A, 18B 18C and 18D are illustrations of the passive elastic member 1728 of FIG. 17A, according to an illustrative embodiment of the invention. The passive elastic member 1728 provides bidirectional stiffness and is connected in series with the linear actuator 1716 and the foot member 1708. The passive elastic member 1728 is coupled at one end to the second end 1748 of the linear actuator 1716, and at the other end to the foot member (not shown). The passive elastic member 1728 includes a strain sensor 1804 coupled to the passive elastic member 1728 for measuring strains in the passive elastic member 1728. In this embodiment, the strain sensor 1804 is a strain gage whose response is calibrated to measure the force applied by the linear actuator 1716—and in turn, the moment about the ankle joint 1740 that is applied by the linear actuator 1716. The strain gage signal is measured us the controller 1762 of FIG. 17A.

In this embodiment, the passive elastic member 1724 is a formed carbon-fiber layup that delivers a desired bidirectional (functions in bending in both directions) normalized drive stiffness. In one embodiment, the passive elastic member 1724 has a preferred compression of 14-25 N-m/rad/kg and tension: 4-8 N-m/rad/kg. Biomechanical forces and torques strongly scale with body mass of a wearer. When scaling prosthetic and orthotic devices, design parameter specifications are typically normalized. For example, series and parallel elasticity such devices can be scaled with body mass, or designed to provide discrete values that are intended to cover several ranges of body mass. The ranges of compression and tension reflect the variation in torque that results from the difference in the linear actuator moment arm to the ankle joint across the entire range of rotation—from maximum plantarflexion to maximum dorsiflexion. The series spring constant is optimized to be relatively non-compliant during swing-phase dorsiflexion position control (while the spring is in compression) such as when the ankle is being repositioned immediately following toe-off in walking. However, some compliance is maintained to isolate the linear actuator from shock loads.

Figure 18C:
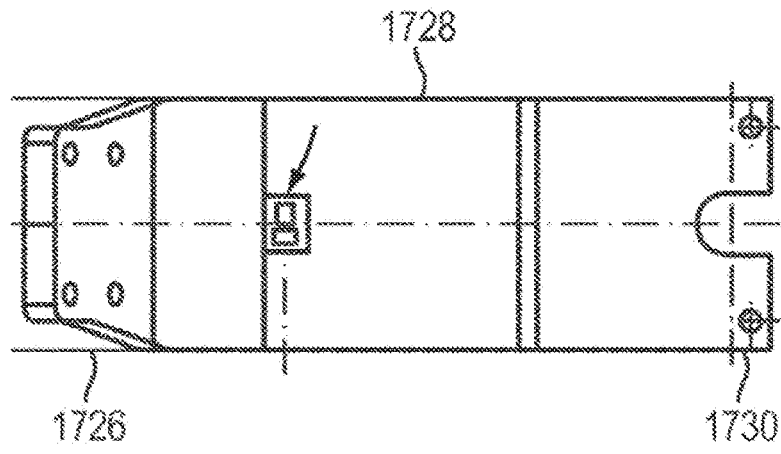
Figure 18D:
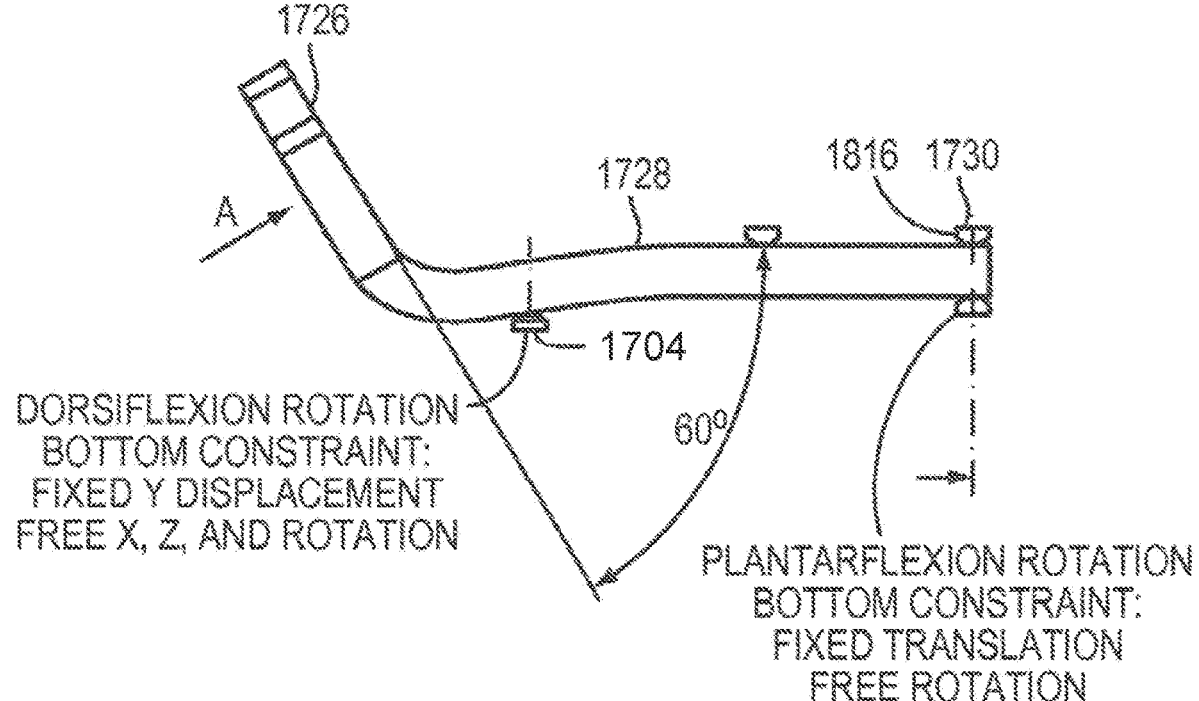

Referring to FIGS. 18C and 18D, high stiffness is achieved in the passive elastic member 1728 in compression by inserting a dorsiflexion rotation bottom constraint 1808 towards the distal end 1726 of the passive elastic member (spring) 1728. This restraint reduces the effective moment arm of the linear actuator 1716 on the bending of the series spring 1728 during compression (towards dorsiflexion). In tension, the moment arm is effectively increased by placing the plantarflexion top constraint 1816 more towards the proximal end 1730 of the spring restraint. With the longer moment arm, the spring beam will bend more freely, thereby reducing the spring constant in tension. In addition to the bilateral stiffness characteristics, in some embodiments, the spring constant of the passive elastic member 1728 is optimized to minimize ball-screw rotational speed. By design, this embodiment of the elastic member 1728 has asymmetrical characteristics delivering higher compliance in tension than in compression. The higher compliance in tension increases the energy storage in the series spring 1728 for use in powered plantarflexion. The energy is released in about the first 100 ms involved in powered plantarflexion, thereby reducing the energy contribution required of the linear actuator 1716. In embodiments of the invention that use a ball-screw transmission assembly in conjunction with a rotary motor for the linear actuator (e.g., ball-screw transmission assembly 2024 of FIGS. 20A-20B this has the added benefit of reducing the required operating speed of the ball-nut assembly portion of the ball-screw transmission assembly and also the motor drive requirements for the rotary motor. The spring catapults the foot member without requiring high-speed ball-nut positioning in this case. Optimized values for the series elasticity are in the range of 3-4 Nm/rad/kg.

Figure 19A:
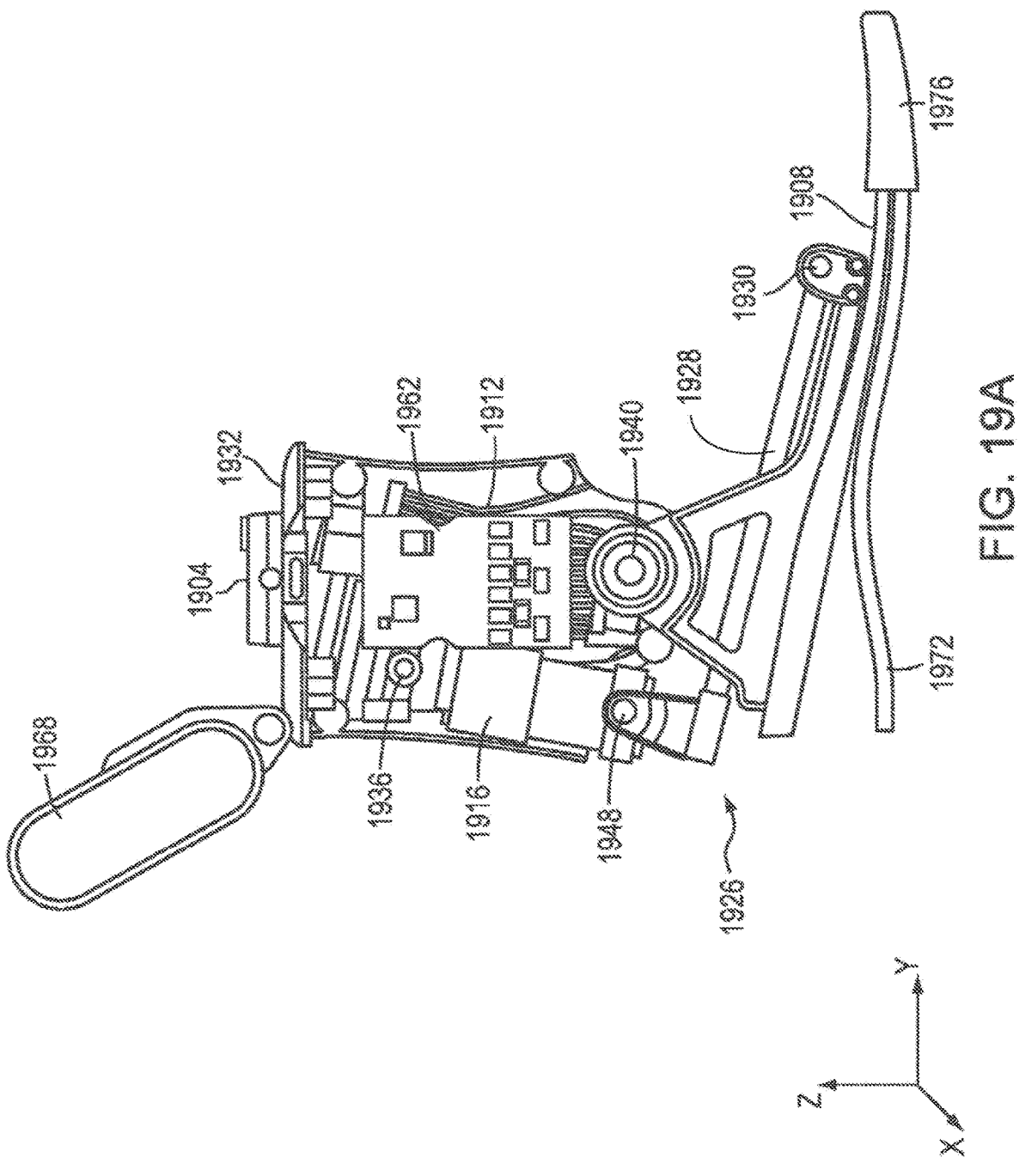
FIG. 19A is an illustration of a lower-extremity prosthetic apparatus incorporating a flat series spring, according to an illustrative embodiment of the invention.

FIG. 19A is an illustration of a lower-extremity prosthetic apparatus 1900 incorporating a flat series spring serving as a passive elastic member 1928, according to an illustrative embodiment of the invention. The apparatus 1900 has a mounting interface 1904 making it capable of attaching to a complementary lower-extremity limb socket member of a wearer. The apparatus 1900 includes a lower leg member 1912 coupled to the mounting interface 1904. The lower leg member 1912 is also coupled to a foot member 1908 at an ankle joint 1940 of the apparatus 1900. The ankle joint 1940 permits the foot member 1908 to rotate about the x-axis relative to the lower leg member 1912. The foot member includes a heel 1972 and a toe 1976.

The apparatus 1900 also includes a linear actuator 1916 with a first end 1936 and a second end 1948. The first end 1936 of the linear actuator 1916 is coupled to the lower leg member 1912. The apparatus 1900 also includes passive elastic member 1928 in series with the linear actuator 1916. The passive elastic member 1928 is coupled between the foot member 1908 and the second end 1948 of the linear actuator 1916. The passive elastic member 1928 is coupled to the foot member 1908 at the proximal end 1930 of the passive elastic member 1928. The distal end 1926 of the passive elastic member 1928 is coupled to the second end 1948 of the linear actuator 1916. The linear actuator 1916 applies torque about the ankle joint 1940.

The apparatus 1900 also includes a controller 1960 coupled to the linear actuator 1916 for controlling the linear actuator 1916. In this embodiment, the controller 1960 is located within a housing 1932 of the apparatus 1900 to protect it from the environment; however, a portion of the housing is removed in this figure to expose the contents within the housing). A battery 1968 coupled to the apparatus 1900 provides power to the apparatus 1900 (e.g., the controller 1960 and various sensors associated with the apparatus 1900).

The passive elastic member 1928 of FIG. 19A is a flat spring (e.g., fabricated with water-cut equipment). A flat spring reduces the cost of the passive elastic member 1928 and makes it easier to configure the spring constant to align with the body mass of the wearer. In one embodiment, the spring is split longitudinally (along the y-axis) to reduce the out-of-plane moment on the components of a ball-nut (see, e.g., FIGS. 20A and 20B) of the linear actuator 1916 due to lack of parallelism between the rotation axis of the ball-nut and the series passive elastic member 1928. In this embodiment, no strain sensing is employed in the actuator torque feedback loop. Rather, the torque transmitted through the spring is estimated by multiplying the known spring constant of the flat spring by the measured spring deflection (difference between measured ankle joint 1940 angle, θ and the angle, β, kinematically defined as the ankle joint 1940 angle that would result from a specific ball-nut position along the screw when the spring deflection is zero.

Figure 19B:
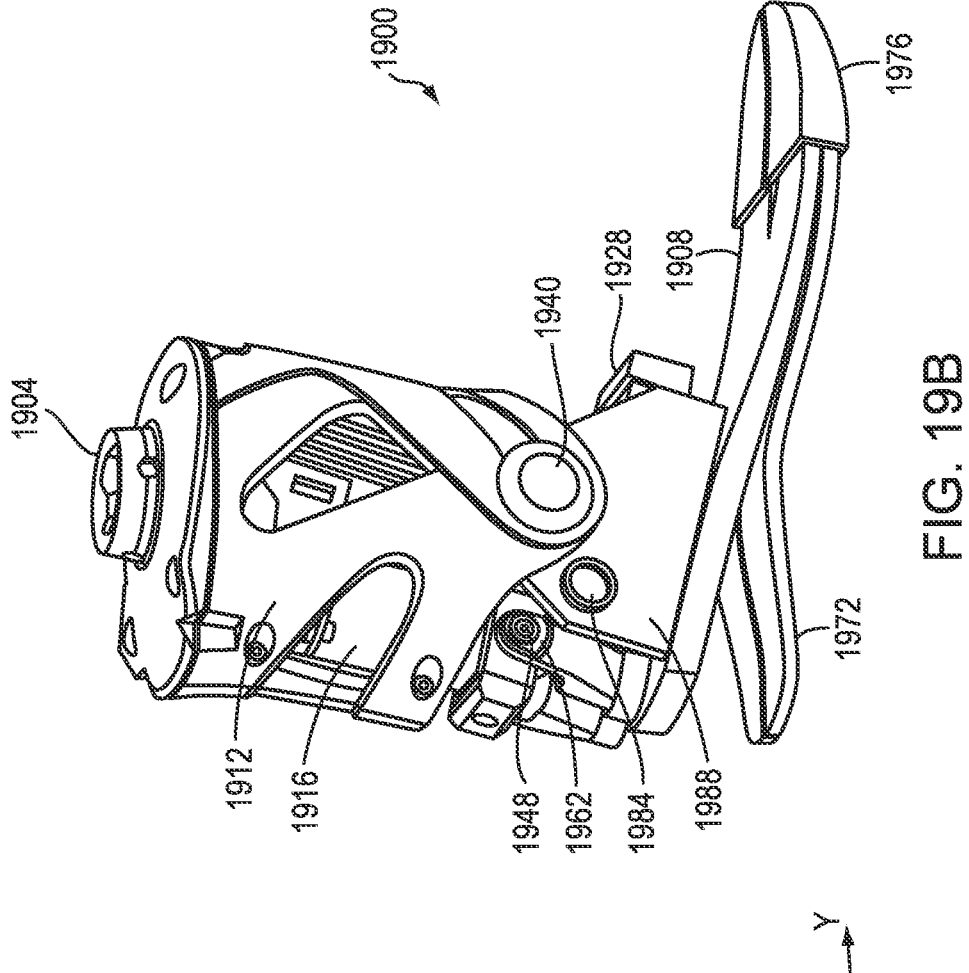
FIGS. 19B-19C are illustrations of a prosthetic apparatus using an alternative series spring, according to an illustrative embodiment of the invention.
Figure 19C:
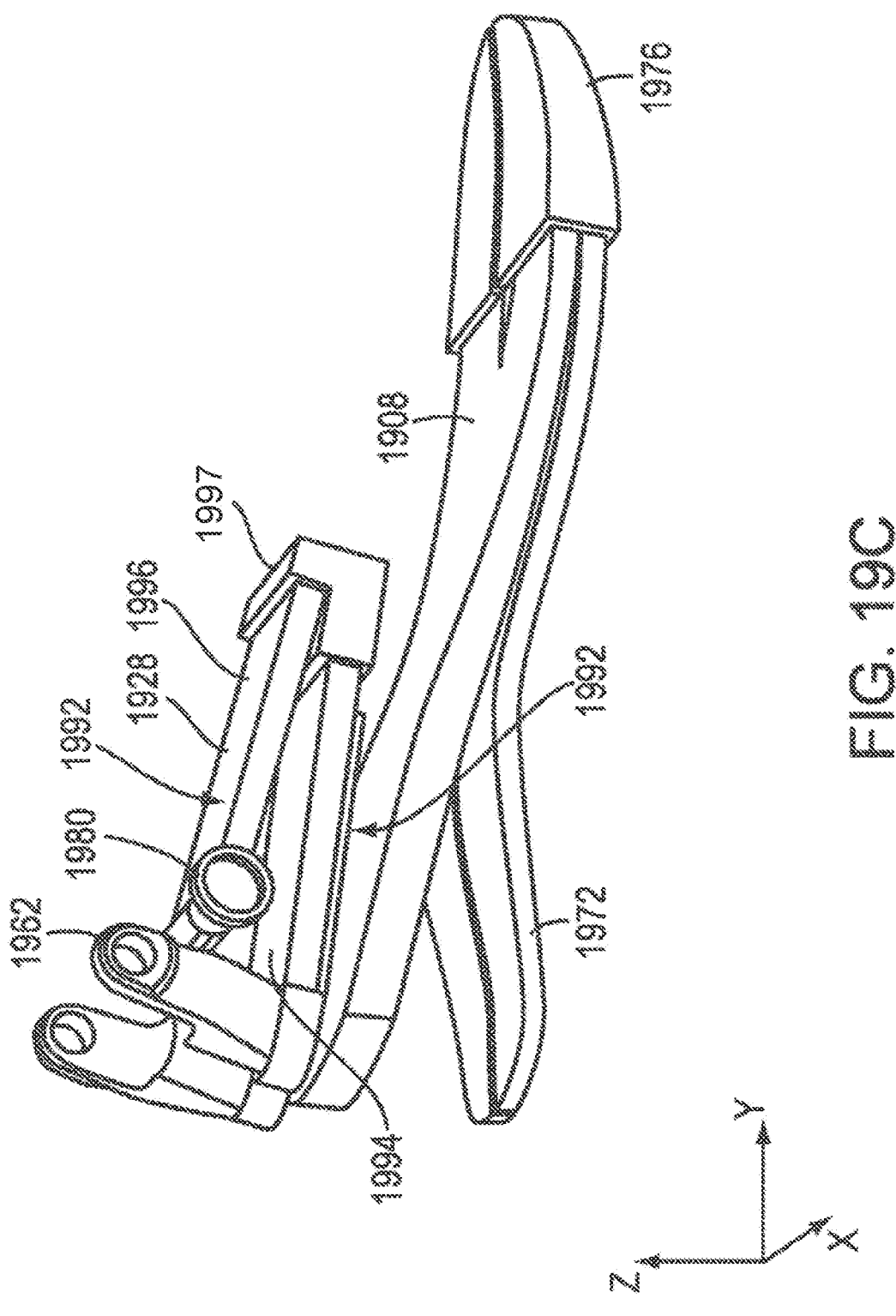

FIGS. 19B and 19C are illustrations of an alternative two-piece series-elastic spring of a prosthesis apparatus 1900, according to an illustrative embodiment of the invention. The apparatus 1900 has a mounting interface 1904 making it capable of attaching to a complementary lower-extremity limb socket member of a wearer. The apparatus 1900 includes a lower leg member 1912 coupled to the mounting interface 1904. The lower leg member 1912 is also coupled to a foot member 1908 at an ankle joint 1940 of the apparatus 1900. The ankle joint 1940 permits the foot member 1908 to rotate about the x-axis relative to the lower leg member 1912. The foot member includes a heel 1972 and a toe 1976. The apparatus 1900 also includes a linear actuator 1916 with a first end (not shown) and a second end 1948. The first end of the linear actuator 1916 is coupled to the lower leg member 1912. The apparatus 1900 also includes a coupling member 1988 (e.g., bracket) that couples the foot member 1908 to the lower leg member 1912 at the ankle joint 1940 with a bearing that allows the foot member 1908 to rotate about the x-axis of the ankle joint 1940.

The apparatus 1900 also includes passive elastic member 1928 in series with the linear actuator 1916. Referring to FIG. 19C, the passive elastic member 1928 has two member sections e.g., beam-like sections)) 1994 and 1996. The elastic member 1928 also has a first end 1962 on the first member 1994 and a second end 1980 on the second member 1996. The elastic member 1928 also has an intermediate location 1997 at which the two members 1994 and 1996 meet and at which the two members 1994 and 1996 pivot with respect to each other around the x-axis. As the second member 1996 pivots towards the first member 1994, the elastic member stores energy in compression during dorsi-flexion (shown by the arrow 1992).

The first end 1962 of the elastic element 1928 is coupled to the second end 1948 of the linear actuator 1916 with a bearing that allows for rotation about the x-axis. The second end 1980 of the elastic element 1928 couples to a location on the coupling member 1988 with a bearing that allows for rotation about the x-axis.

Exemplary Linear Actuator

Figure 20B:
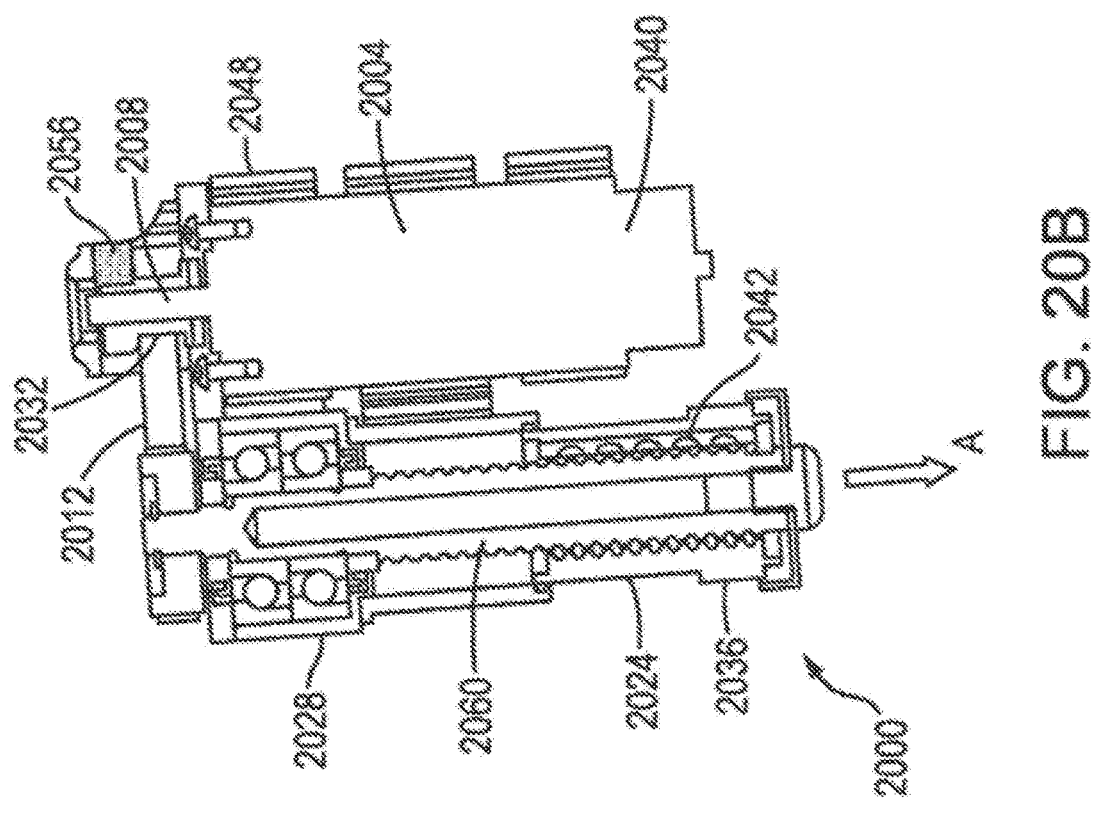
FIG. 20B is an illustration of a cross-sectional view of the linear actuator of FIG. 20A.
Figure 20A:
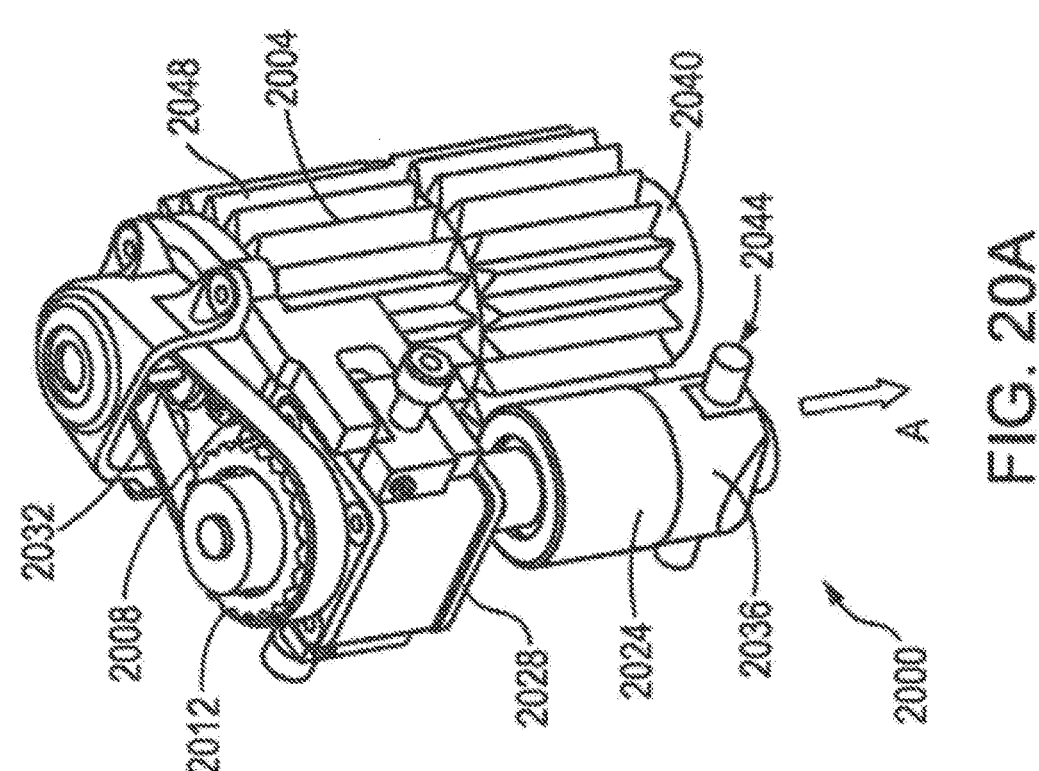
FIG. 20A is an illustration of a perspective view of a linear actuator capable of being used in various lower-extremity prosthetic, orthotic, and exoskeleton apparatus, according to an illustrative embodiment of the invention.

FIGS. 20A and 20B are illustrations of a linear actuator 2000 for use in various lower-extremity prosthetic, orthotic, and exoskeleton apparatus, according to an illustrative embodiment of the invention. FIG. 20A is a perspective view of the linear actuator 2000. FIG. 20B is a cross-sectional view of the linear actuator 2000. The linear actuator 2000 can be used as, for example, the linear actuator 1716 of apparatus 1700 of FIG. 17A or apparatus 400 of FIG. 4. The actuator 2000 includes a motor 2004 and screw transmission assembly 2024 (in this embodiment, it is a ball-screw transmission assembly, also referred to as a ball-screw assembly) for delivering linear power along the A axis. The screw transmission assembly 2024 functions as a motor drive transmission to translate rotational motion of the motor 2004 to linear motion. In one embodiment, the ball-screw transmission assembly 2024 is a custom ball-screw transmission assembly manufactured by Nook Industries (offices in Cleveland, Ohio). The custom ball-screw transmission assembly has the following specifications: 14 mm×3 mm pitch screw, 4000 N of thrust at 150 mm/s, and an L1 rated life in the instant application of 5 million cycles. In some embodiments, the screw transmission assembly is a lead-screw transmission assembly (also referred to as a lead-screw assembly).

The actuator 2000 includes a rotary motor 2004 that has a motor shaft output 2008. The motor shaft output 2008 has a pulley 2032 coupled (e.g., welded) to the motor shaft output 2008. In one embodiment, the rotary motor 2004 is a high-speed brushless motor (model EC30 motor manufactured by Maxon Motor AG, Maxon Precision Motors, Inc. with offices in Fall River, Mass.). The motor 2004 includes an inductive incremental-absolute angular encoder 2040 that is integrated into the motor 2004 to for determining angular alignment between the rotor and stator of the rotary motor 2004. The encoder 2040 also provides a position feedback signal necessary to control the threaded shaft 2060 position of the linear actuator 2000 and to provide for "instant-on" motor commutation and redundant position feedback monitoring.

The inductively-coupled encoding elements of the encoder 2040 enable the system to determine the absolute rotor-stator alignment (with, for example, 10 bits of resolution per revolution) simultaneously with high-precision incremental rotor position feedback. By cross-checking these redundant feedback elements it is possible to minimize the possibility that an encoder malfunction can cause ankle control instability. The incremental encoder achieves less than 300 µrad of run-out so as to eliminate the sensed velocity fluctuations when the ball-screw transmission assembly 2024 (see below) is operating at constant-speed. As a result, less torque variation is applied by the actuator 2000.

The rotary motor 2004 also includes an integral motor heat-sink 2048. In one embodiment, the heat-sink 2048 draws heat out of the windings of the motor 2004, enabling a wearer to walk at peak levels of non-conservative work without exceeding motor coil temperature limits (typically 160° C.). Motor heating arises due to resistive losses (PR losses) in the motor 2004 as the linear actuator 2000 delivers thrust force. As the coil temperature rises, the coil resistance rises at the rate of 0.39%/° C., thereby further increasing the coil temperature. In addition, the motor $K_t$ (a measure of torque as it scales with motor current) typically drops by nearly 20% as the coil temperature increases to its limit. This requires additional current consumption to perform the same amount of work, further driving up the coil temperature. The heat-sink in the linear actuator 2000 reduces coil temperature rise by over 40%. Because the wear out phenomenon that drives premature failure of motor winding insulation and motor bearing reduces in effect by a factor of 2× for every coil temperature reduction of 10° C., the motor life increases significantly if lower motor coil operating temperatures are maintained. And, using this intrinsic coil temperature sensing method, the motor can be protected from exceeding the absolute maximum rating of 160° C. by simply reducing powered plantarflexion power (currents) as the maximum rating is approached, and ultimately, shutting off battery power when a predefined limit of, for example, 150° C. is reached.

Robotic prostheses typically employ compact lightweight motor drives to deliver power in bursts to the affected limb. In some scenarios, the power bursts may be applied repetitively and at high rate over extended periods of time. The motor copper and eddy current losses will cause an excessive accumulated heating effect that causes the motor winding temperature to rise. Since the copper winding resistance increases with temperature (0.39%/° C.), the copper losses will increase thereby amplifying the heating effect. A critical winding temperature limit can sometimes be reached in which further temperature rise will cause permanent damage to the motor. Sensing when this temperature limit is reached is preferably accomplished by the control system.

Two conventional methods may be used to prevent or detect when the copper winding temperature limit is or will be reached. In the first, the copper and eddy current losses are computed while the control system operates. These are used to drive a thermal model of the windings so that the winding temperature can be estimated. Sometimes the ambient temperature is measured in order to yield a better winding temperature measurement. An advantage of this method is that it is cheap to implement. The disadvantage is that the coil temperature model is hard to obtain and to calibrate. Also, it is often difficult to make a good measurement of the ambient temperature around the motor, causing the winding temperature measurement to be in error.

In the second method, sometimes combined with the first, the case temperature of the motor is measured with a thermistor applied to the outside of the case, or inside the motor. The advantage of this is that it provides a direct measurement. The disadvantage is that it only measures at one point and the application of the sensor is expensive and often unreliable.

A more preferred approach is to both detect the temperature and to mitigate the potential overheating condition. In this, we measure the motor winding resistance on every step at a point during the walking cycle when we can briefly hold the ankle at a fixed position (this to eliminate back-emf effects on the resistance calculation) to make the measurement. In one embodiment, coil temperature is determined by applying a fixed current (alternatively fixed voltage) to the motor winding and measuring the corresponding voltage (alternatively current) in the winding. To increase the accuracy, we apply the voltage (or current) in both the forward and reverse direction and measure the difference in current (or voltage).

Since the motor drive electronics employs PWM current control methods, all the infrastructure to make this measurement exist. By noting the percentage difference between this winding resistance and that when the ankle is at rest (a calibration constant) we can estimate the winding resistance in-situ without cost. In a typical servo system this measurement cannot be made because the actuator must be continually in closed-loop control. But in the ankle prosthesis, there are times (swing phase) when the ankle position does not need to sustain the precision control over the 5 milliseconds typically required to make the measurement. Once the winding temperature is calculated in this way, the control system can detect when the windings are approaching the critical temperature. During these times, the drive power available for walking is reduced or eliminated altogether until the temperature is reduced to a safe level.

In some embodiments, the output of the temperature sensor 2052 is provided to a controller (e.g., the controller 1762 of FIG. 17A) to control torque output by the linear actuator 2000 based on the temperature of the motor 2004.

A belt 2012 couples the pulley 2032 to the threaded shaft 2060 of a ball-screw transmission assembly 2024 such that rotational motion of the motor shaft output 2008 is translated to a linear motion of the ball-nut assembly 2036 portion of the ball-screw transmission assembly 2024. In some embodiments, two or more belts are applied in parallel, each with an ability to drive the linear actuator 2000 ball-screw transmission assembly 2024 by itself, so as to enable the linear actuator 2000 to survive a single belt breakage failure. In such an event, belt break sensor 2056 senses the condition and validates belt integrity during operation (e.g., during each gait cycle of a wearer using a prosthesis).

In one embodiment, an optical sensor (e.g., a thru-beam sensor) is used as the belt break sensor and an output signal of the optical sensor changes in a known manner when a belt breaks. In another embodiment of the invention, a capacitive sensor is used as the belt break sensor and an output of the capacitive sensor changes in a known manner when a belt breaks.

In one embodiment, the pulley 2032 and belt(s) are not used as the apparatus for converting rotary motion to a linear motion. Rather, a set of traction wheels are used as the transmission apparatus. In this embodiment, the threat of belt failure is thereby eliminated.

In one embodiment, in the event of a belt break, a controller of the apparatus in which the linear actuator 2000 is used (e.g., controller 1762 of apparatus 1700 of FIG. 17A), changes the position of the foot member relative to the lower leg member to a safe position that enables the apparatus to operate as a passive ankle prosthesis until the linear actuator 2000 is repaired. In one embodiment, the controller shorts three electrical leads of the rotary motor 2004 in response to the belt breakage sensor detecting a failure of one or more of the plurality of belts. Shorting the three-phase electrical input leads to the motor 2004 introduce a viscous drag on the motor shaft output 2008. While walking, the viscous drag holds roughly fixed the rotor shaft output so that the apparatus operates as a passive prosthesis. However, the apparatus can be moved slowly in a way that enables it to move to a non-fixed equilibrium position when standing or sitting. Each input lead is shorted to ground by its own individual switch.

In one embodiment, the switches are operated by a rechargeable battery (a separate battery from the primary battery used to operate the apparatus). By using a separate battery, the switches would short the input leads (and place the apparatus into a safe mode) even if a failure occurred (or the primary battery was depleted).

In one embodiment, the threaded shaft 2060 includes a hollowed out portion that contains a noise damping material to reduce the noise generated by the actuator 2000 and the apparatus within which the actuator 2000 is used. In one embodiment, the threaded shaft 2060 is 14 mm diameter stainless steel shaft 8.7 mm diameter bore that extends 64 mm of the length of the shaft, filled with ISODAMP® C-1002 acoustic damping material manufactured by 3M (with offices in St. Paul, MN).

The actuator 2000 also includes a radial and thrust bearing 2028 that support the belt 2024 tension due to the rotary motor 2004 and the thrust force of the ball-nut assembly 2036. Loads due to the belt tension and thrust force are present both statically and during the gait cycle.

The ball-nut assembly 2036 includes one or more recirculating ball-tracks 2042 that retain a plurality of ball bearings; the combination of which support the linear motion of the ball-nut assembly 2036. In one embodiment, five ball-tracks are used. The actuator 2000 includes a coupling element 2020 (e.g., the second end 1748 of the linear actuator 1716 of FIG. 17A) that couples the actuator 2000 to, for example, a passive elastic member of a foot member of a prosthetic apparatus (e.g., passive elastic member 1724 of FIG. 17A).

Figure 21:
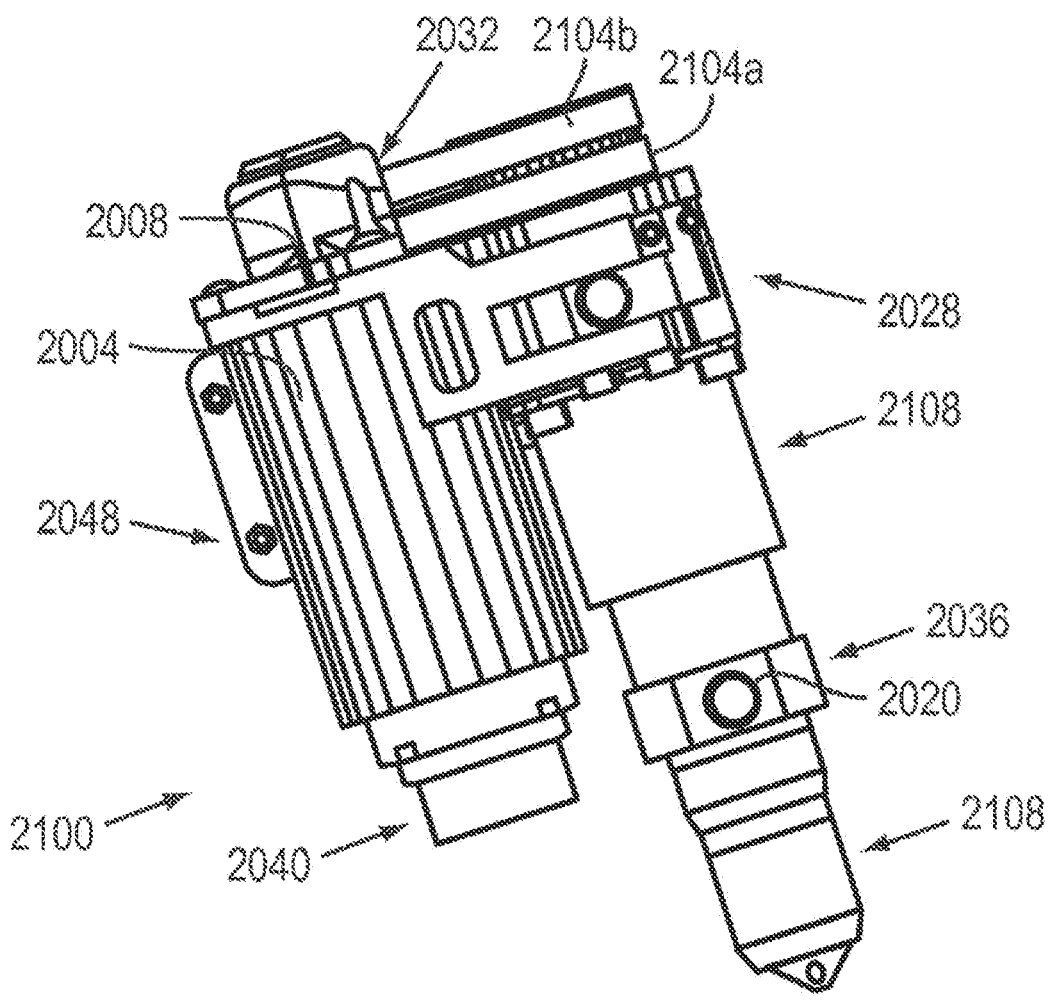
FIG. 21 is an illustration of a perspective view of a linear actuator capable of being used in various lower-extremity prosthetic, orthotic, and exoskeleton apparatus, according to an illustrative embodiment of the invention.

FIG. 21 is an illustration of a perspective view of a linear actuator 2100 for use in various lower-extremity prosthetic, orthotic, and exoskeleton apparatus, according to an illustrative embodiment of the invention. The linear actuator 2100 can be used as, for example, the linear actuator 1016 of apparatus 1000 of FIG. 17A or apparatus 400 of FIG. 4. The linear actuator 2100 is a variation of the actuator 2000 of FIGS. 20A and 20B.

The actuator 2100 includes a rotary motor 2004 that has a motor shaft output 2008. The motor shaft output 2008 has a pulley 2032 welded to the motor shaft output 2008. The motor 2004 includes an inductive incremental-absolute angular encoder 2040 that is integrated into the motor 2004 to for determining angular alignment between the rotary motor 2004 rotor and stator. The rotary motor 2004 also includes an integral motor heat-sink 2048.

Two belts 2104a and 2104b are used in parallel, rather than the single belt 2012 of FIGS. 20A and 20B. Each belt has the ability to drive the linear actuator transmission by itself with 1.5× margin on belt breakage, so as to enable the linear actuator 2100 to survive a single belt breakage failure. In one embodiment, in the event of a belt break, a controller of the apparatus in which the linear actuator 2100 is used (e.g., controller 1762 of apparatus 1700 of FIG. 17A) moves the ankle to a safe position in a way that would enable the apparatus to operate as a passive ankle prosthetic until the linear actuator 2100 is repaired. In one embodiment, the controller shorts three electrical leads of the rotary motor 2004 in response to the belt breakage sensor detecting a failure of one or more of the plurality of belts. In such an event, one or more belt break sensors would sense the condition and move the ankle to a safe position in a way that would enable the system to operate as a passive ankle prosthesis until the linear actuator is repaired.

The two belts 2104a and 2104b couple the pulley 532 to a threaded shaft of a ball-screw transmission assembly (e.g., threaded shaft 2060 of FIG. 20B) such that rotational motion of the motor shaft output 2008 is translated to a linear motion of the ball-nut assembly 2036 portion of the ball-screw transmission assembly. The actuator 2100 also includes a radial and thrust bearing 2028 that support the tension in belts 2104a and 2104b due to the rotary motor 2004 and the thrust force of the threaded screw. Loads due to the belt tension and thrust force are present both statically and during the gait cycle.

The ball-nut assembly 2036 includes recirculating ball-tracks that retain a plurality of ball bearings; the combination of which support the linear motion of the ball-nut assembly 2036. The actuator 2100 includes a coupling element 2020 (e.g., the second end 1748 of the linear actuator 1716 of FIG. 17A) that couples the actuator 2100 to, for example, a passive elastic member of a foot member of a prosthetic apparatus (e.g., passive elastic member 1724 of FIG. 17A).

The actuator 2100 also includes a ball-screw assembly seal 2108. The ball-screw assembly seal 2108 protects the screw from, for example, contaminants (e.g., sand, dirt, corrosive materials, sticky materials). Such contamination would cause the design life of the actuator to become indeterminate.

Exemplary Lower-Extremity Orthotic (Wearable Robotic Knee Brace)

Figures 22A, 22B:
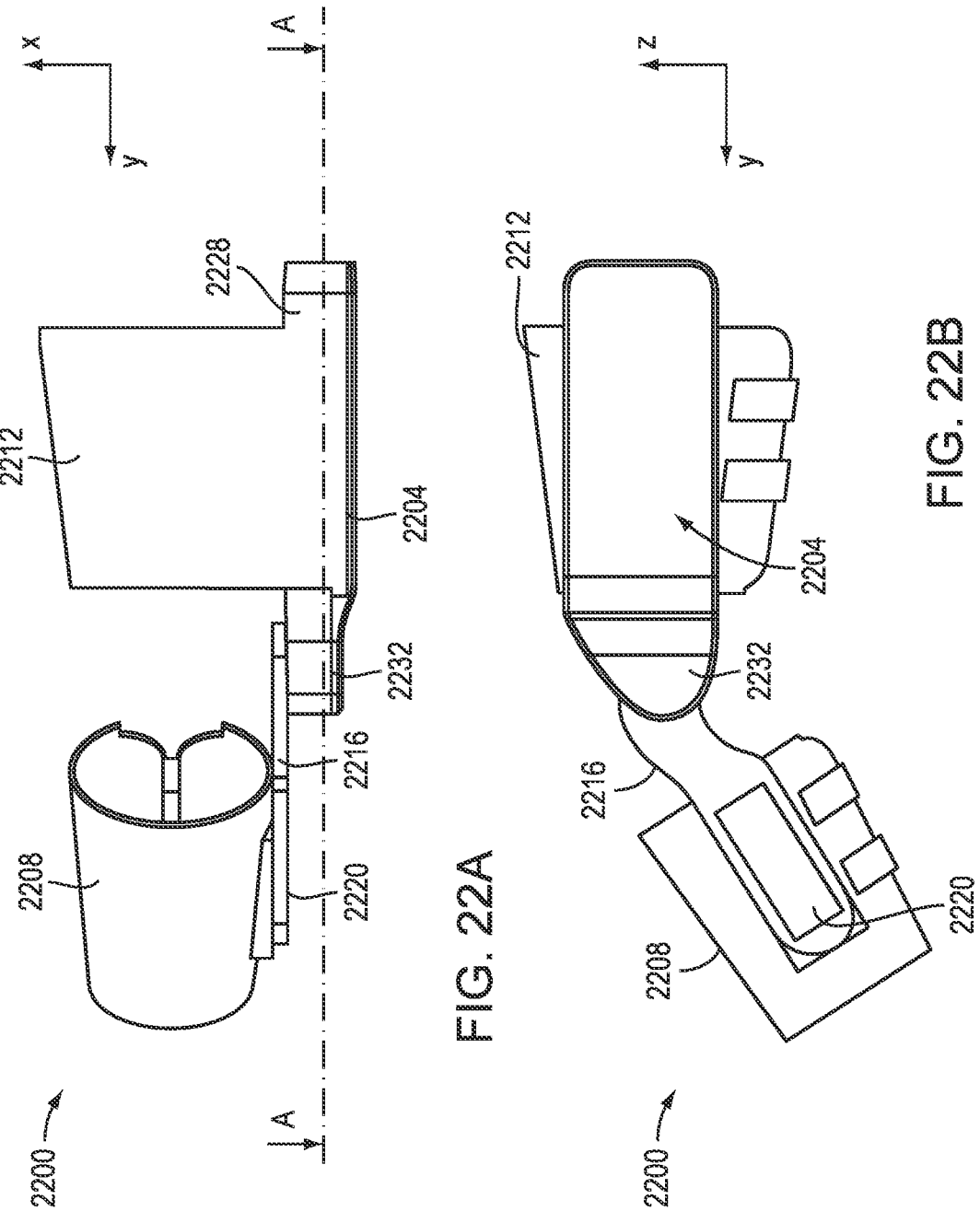
FIG. 22A is a schematic illustration of a top view of a lower-extremity orthotic or exoskeleton apparatus (wearable robotic knee brace), according to an illustrative embodiment of the invention.
FIG. 22B is a side view of the apparatus of FIG. 22A.
Figure 22C:
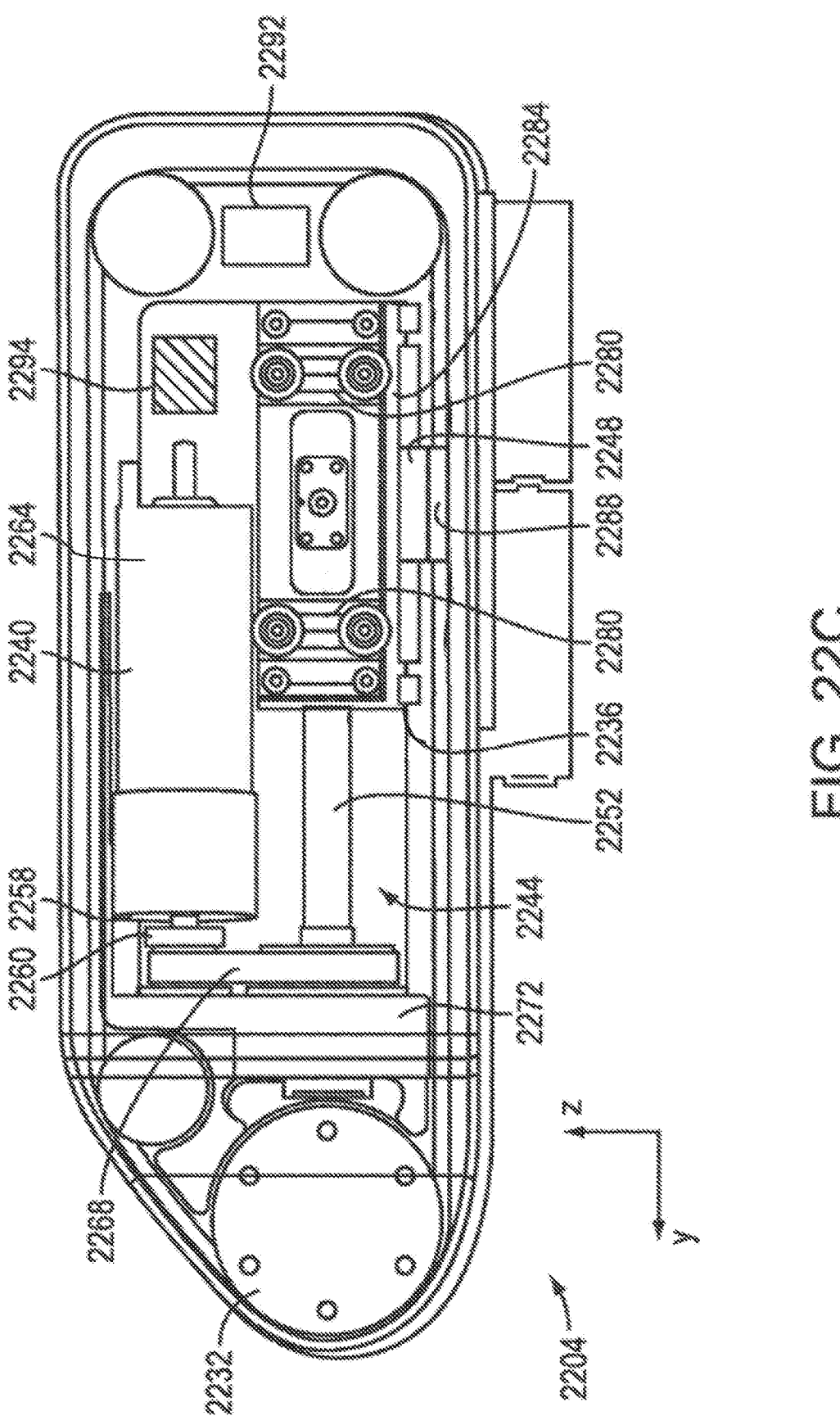
FIG. 22C is a schematic illustration of the interior portion of the knee joint drive assembly of the apparatus of FIGS. 22A and 22B.

FIGS. 22A, 22B and 22C are schematic illustrations of a lower-extremity orthotic or exoskeleton apparatus 2200 (wearable robotic knee brace), according to an illustrative embodiment of the invention. The apparatus 2200 is a knee-brace that augments the wearer's lower-extremity function. FIG. 22A is a top view of the apparatus 2200. FIG. 22B is a side view of the apparatus 2200. FIG. 22C is a view of the interior portion of a knee joint drive assembly 2204 of the apparatus 2200. Typical use cases for the apparatus 2200 include, for example, metabolic augmentation, permanent assistance for wearers with a permanent limb pathology, or rehabilitation for wearers with temporary limb pathology.

An example of a metabolic augmentation use case involves, for example, wearers (e.g., soldiers or other personnel) that need to traverse heavy terrain for extended periods at high speed while carrying heavy loads. In this use case, the knee brace apparatus 2200 augments the wearer's own abilities. An example of a permanent assistance use involves a wearer that suffers from a permanent limb pathology (e.g., knee tendon or meniscus degeneration) with no possibility for rehabilitation. In this use case, the knee brace apparatus 2200 provides permanent assistance to the wearer. An example of a use case involving rehabilitation for wearers with temporary limb pathology involves a wearer recovering from injury or other temporary condition. In this use case, the knee brace apparatus 2200 functions as a programmable telerobotic tool deployed by a physical therapist to accelerate recovery-through progression of kinesthetic rehabilitation and gradually decreasing assistance while the muscle memory and strength recover. In another embodiment, the method includes specifying a physical therapy protocol defining a level of assistance performed by the apparatus on the wearer over a period of time and reducing the level of assistance performed by the apparatus on the wearer to assist in rehabilitation of the limb pathology. In some embodiments, the level of assistance performed by the apparatus is reduced based on impedance and torque contribution of the wearer to the apparatus.

Referring to FIGS. 22A and 22B, the apparatus 2200 includes a lower leg member 2216 (also referred to as a drive arm), a thigh member 2228, a lower leg cuff 2208 and an upper leg cuff 2212. The lower leg cuff 2208 is coupled to the lower leg member 2216. The lower leg cuff 2208 attaches the apparatus 2200 to the lower leg of the wearer. The upper leg cuff 2212 is coupled to the thigh member 2228. The upper leg cuff 2212 attaches the apparatus 2200 to the thigh of the wearer. The apparatus 2200 includes a knee joint drum 2232 for connecting the thigh member 2228 to the lower leg member 2216. The knee joint drum 2232 (e.g., a rotary bearing) permits the lower leg member 2216 to rotate about the x-axis relative to the thigh member 2228.

Referring to FIG. 22C, the knee joint d assembly 2204 includes a linear actuator that drives the knee joint drum 2232 through a belt drive transmission 2236. The linear actuator is a rotary motor 2240 (e.g., brushless motor) and ball-screw transmission assembly 2244 (e.g., the motor 2004 and ball-screw transmission assembly 2024 of FIGS. 20A and 20B). In the apparatus 2200, rotational motion of the motor shaft output 2258 of the motor 2240 is translated to a linear motion of the ball-nut assembly 2248 portion of the ball-screw transmission assembly 2244. The motor shaft output 2258 has a pulley 2260 coupled (e.g., welded) to the motor shaft output 2258. The motor 2240 includes an inductive incremental-absolute angular encoder 2264 that is integrated into the motor 2240 for determining angular alignment between the rotor and stator of the rotary motor 2240. The encoder also provides a position feedback signal necessary to control the screw 2252 position of the ball-screw transmission assembly 2244 and to provide for "instant-on" motor commutation and redundant position feedback monitoring.

A belt 2268 couples the pulley 2260 to the threaded shaft 2252 of the ball-screw transmission assembly 2244 such that rotational motion of the motor shaft output 2258 is translated to a linear motion of the ball-nut assembly 2248 portion of the ball-screw transmission assembly 2244.

In one embodiment, the threaded shaft 2252 includes a hollowed out portion that contains a noise damping material to reduce the noise generated by the knee joint drive assembly 2204. The knee joint drive assembly 2204 also includes a radial and thrust bearing 2272 that support the belt 2268 tension due to the rotary motor 2240 and the thrust force of the screw 2252. Loads due to the belt tension and thrust force are present both statically and during the gait cycle.

The knee joint drive assembly 2204 also includes a spring 2280 for series elasticity, spring cage 2284, drive belt 2236 and a spring cage/belt connection 2288. In some embodiments, a drive band (e.g., thin piece of spring steel) is used in place of the drive belt 2236. In some embodiments, a drive cable (e.g., loop of stranded material) is used instead of the drive belt 2236. Spring 2280 is a series passive elastic element, functioning in the same manner as the series elastic spring element I 728 of FIG. 17A. The spring cage 2284 provides a closed volume in which the spring 2280 is located. The ball-nut transmission assembly 2248 is coupled to the screw 2252. The ball-nut assembly 2248 is also coupled to the drive belt 2236. Linear motion of the screw 2252 causes a linear motion in the ball-nut assembly 2248. The linear motion in the ball-nut assembly 2248 causes a linear motion in the drive belt 2236. The linear motion of the drive belt 2236 drives the knee joint 2232.

The apparatus 2200 includes a controller 2292 (e.g., a printed circuit assembly that incorporates the linear actuator 2204, state and inertial measurement unit 2294 (e.g., inertial measurement unit 1720 of FIG. 17A) control and processing functions) to drive and control the operation of the apparatus 2200. Referring to FIG. 228, the apparatus 2200 also includes a torque sensor 2220 coupled to the lower leg member 2216 to measure the torque applied to the lower leg member 22 I 6 by the knee joint drive assembly 2204. The sensor 2220 serves as the feedback element in the control loop of the controller 2292 to achieve high fidelity closed loop position, impedance and torque (for reflex) control of the knee joint 223.2. In one embodiment, an array of force-sensitive transducers are embedded within the cuff structure to provide force measurements used to achieve rapid, biomimetic response.

In some embodiments, the motor angle sensor (e.g., encoder 2264) measures motor position and the controller controls the rotary motor to modulate position, impedance and torque of the knee joint 2232 based on the motor position.

In some embodiments, the apparatus 2200 includes an angle sensor for determining position of the drum 2232 of the belt drive transmission relative to the output of the motor drive transmission and the controller controls the rotary motor for modulating impedance, position or torque based on the position; In some embodiments, the apparatus 2200 includes a displacement sensor for measuring displacement of a series spring in the motor drive transmission for determining force on the series spring and the controller controls the rotary motor for modulating impedance, position or torque based on the force on the spring. In some embodiments, the inertial measurement unit 2294 is coupled to the thigh member or lower leg member for determining an inertial pose of the lower leg member and the controller controls the rotary motor for modulating impedance, position or torque based on the inertial pose. In some embodiments, the torque sensor 2220 measures the torque applied to the lower leg member by the belt drive transmission and the controller controls the rotary motor for modulating impedance, position or torque based on the torque applied to the lower leg member. In some embodiments, the apparatus 2200 includes an angle sensor for determining an angle between the thigh member and lower leg member and wherein the controller controls the rotary motor for modulating impedance, position or torque based on the angle between the thigh member and lower leg member.

In some embodiments, the apparatus 2200, instead of a motor drive transmission, the apparatus includes a screw transmission assembly coupled to the motor shaft output for converting the rotary motion of the motor shaft output to a linear motion output by the screw transmission assembly. In addition, the drive transmission assembly coupled to the output of the motor drive transmission is a redundant belt, band or cable drive transmission coupled to the screw transmission assembly to convert a linear motion output by the screw transmission assembly to a rotary motion for applying torque to the knee joint to rotate the lower leg member with respect to the thigh member.

Unlike the prosthetic apparatus 2000 of FIG. 20A, the knee brace apparatus 2200 operates in parallel with human actuation. In metabolic augmentation and replacement applications, the knee brace control system will supply all of the impedance and torque needs within the gait cycle. It is desirable for the wearer to be able to walk all day without getting tired and without exertion on the augmented side(s) of the body. In rehabilitation applications, the knee-brace apparatus 2200 supplies only a programmed percentage of the impedance and torque. In such applications, the knee-brace apparatus 2200 serves as a telerobotic extension of the physical therapist supervising the wearer's rehabilitation.

In one embodiment of the knee brace control system, the physical therapist creates a protocol to be executed telerobotically by the knee brace over a period of time between therapist visits. Using a wireless interface, patient performance can be fed back to the physical therapist, thereby achieving telepresence. The protocol specifies the rate at which the assistance diminishes over time. As the knee brace apparatus reduces assistance, the knee brace apparatus would compute via biomechanical models the impedance and torque contribution by the wearer-reducing assistance in accordance with the improved response to maintain the desired net biomimetic response. The biomechanical models would involve solving the inverse dynamics of the knee-incorporating inertial rotation and acceleration of the lower leg member, thigh member and torso. This six degree-of-freedom information would be derived from the inertial measurement unit in the thigh member and knee joint angular displacement. The zero-velocity update for the inertial measurement unit would be accomplished similarly as described herein.

Figure 26:
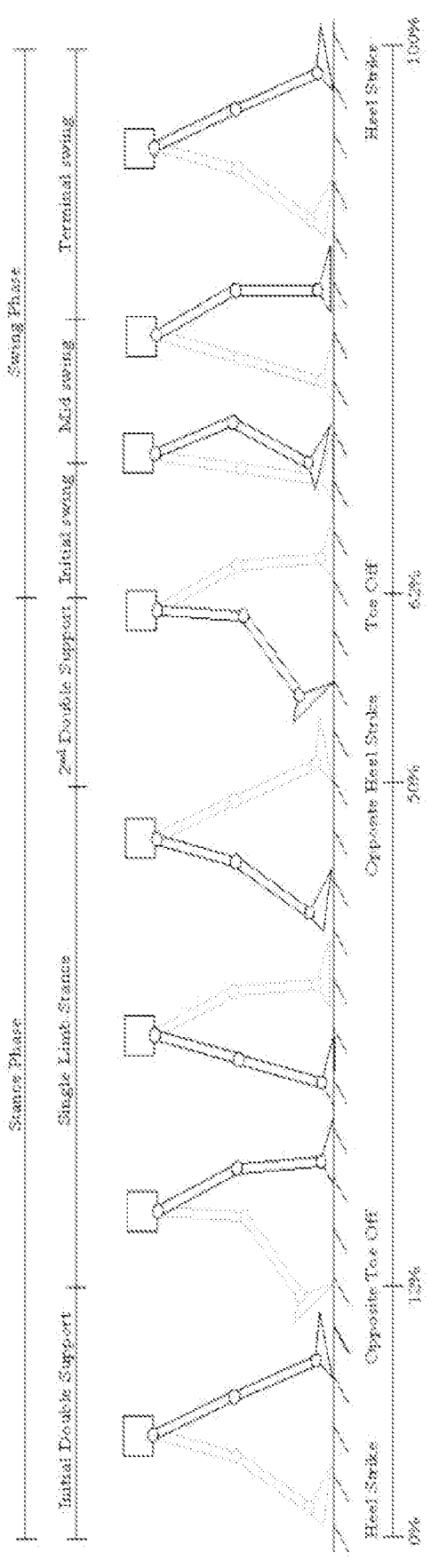
FIG. 26 depicts the biomechanical features of normal human gait during ambulation.

FIG. 26 depicts the biomechanical features of normal human gait during ambulation, initiating and ending at the point of heel strike. It is divided into the stance and swing phases, and entails all elements of motion at the hip, knee, and ankle. Myopathic diseases, such as IBM (inclusion body myositis), are associated with principal quadriceps weakness, which adversely impacts the patient's ability to ambulate safely and efficiently. Equally as important, patients with IBM are unable to safely transition between resting (standing or sitting) and ambulatory states.

Figures 27, 28:
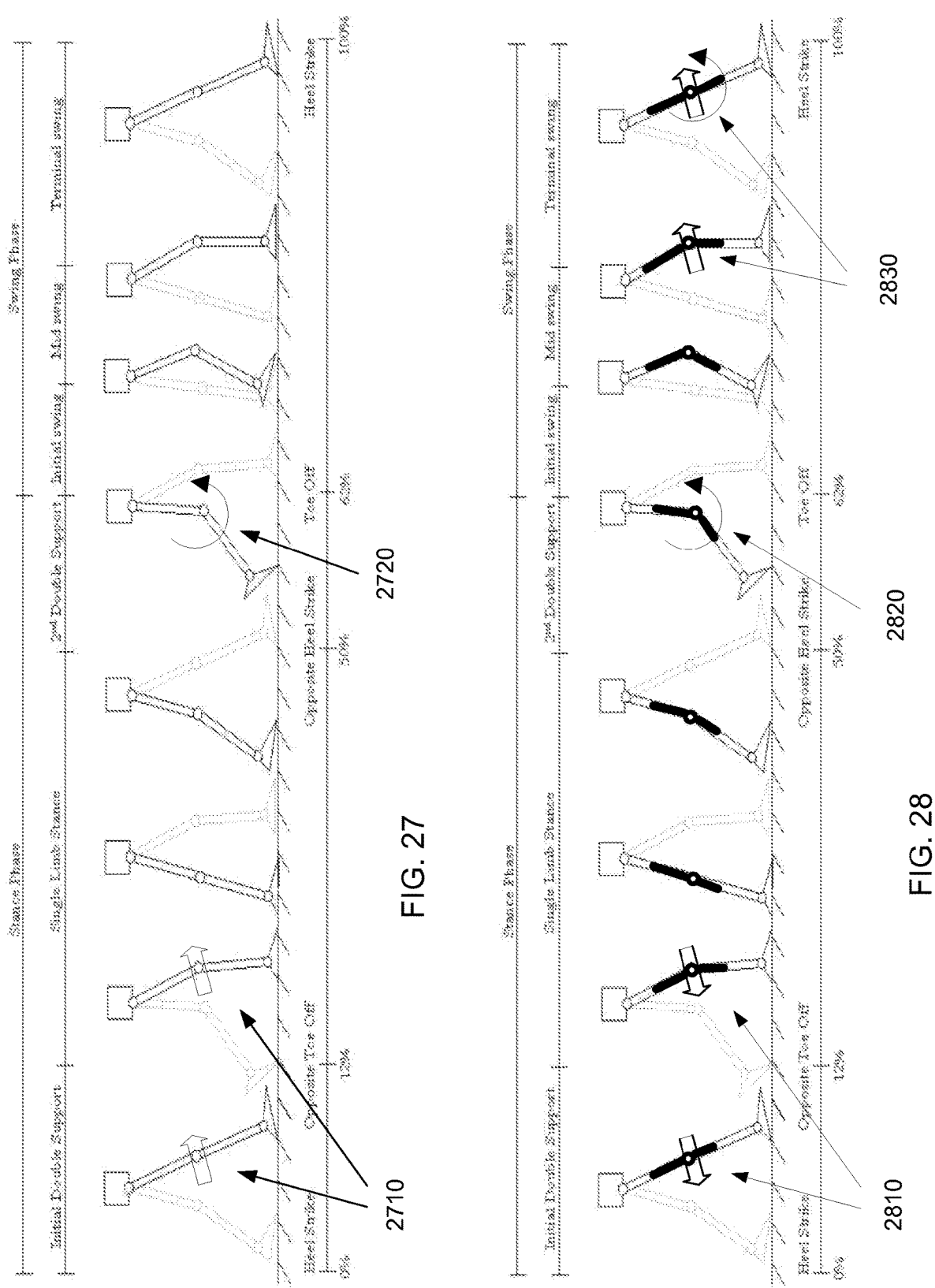
FIG. 27 depicts the biomechanical mechanism by which quadriceps weakness affect ambulation on level ground.
FIG. 28 depicts how a knee apparatus is used to restore normal ambulation.

FIG. 27 illustrates the biomechanical mechanism by which quadriceps weakness affect ambulation on level ground. The overall mechanical sequence is deficient with respect to FIG. 26 in two ways. First, the knee may buckle in early stance if the stiffness (or mechanical impedance) of the knee joint in early stance is inadequate to absorb the shock of foot strike and to apply restorative torque to maintain balance (indicated by reference no. 2710). The inability for the quadriceps to actively stiffen the knee to absorb the foot-strike constrains walking speed, similar to driving a car without brakes. Note that mechanical impedance refers to the stiffness that a joint exerts, and is known to possess three components, a spring component defined by the spring constant and equilibrium position that applies a linear or non-linear restoring torque in response to joint displacement; a damping component that applies a linear or non-linear viscous restoring torque in response to joint velocity; and an inertial component that applies a linear restoring torque in response to joint acceleration and second, in late stance and early swing, the quadriceps may be incapable of applying the knee braking torque to impede rapid knee flexion (indicated by reference no. 2720).

The knee apparatus depicted in FIGS. 22A-C may be used as a robotic-assisted solution to deal with the deficiencies identified above in connection with FIG. 27. FIG. 28 demonstrates using a knee apparatus to restore normal ambulation by employing intrinsic sensing of lower limb trajectory, and by applying biomimetic impedance, augmentative torque, and position control to the patient's knee joint in accordance with the phase of the gait cycle, in order to reconstruct the desired gait trajectory state, terrain, body pose and stability.

In early stance (indicated by reference no. 2810), the knee apparatus provides an increased stiffness to absorb the foot strike energy and to provide a stable platform from which the trailing leg can leave the ground, In late stance as the ankle plantar flexes (indicated by reference no. 2820), and the knee apparatus uses intrinsic measures of thigh and shank orientation and of the wearer's walking speed to apply a biomimetic, reflexive torque-identical to that would be supplied by a fully-functional quadriceps muscle—that propels the wearer upward and forward for metabolically-efficient ambulation. Later, when the knee apparatus senses that the lower-limb is in the swing-phase (indicated by reference no. 2830), the knee is flexed and a high impedance is applied that will absorb (brake) the lower-limb as the foot strikes the ground. The result is safe and metabolically-efficient ambulation.

Balance Using Ground Reaction Forces and Zero Moment Pivot

Figure 23A:
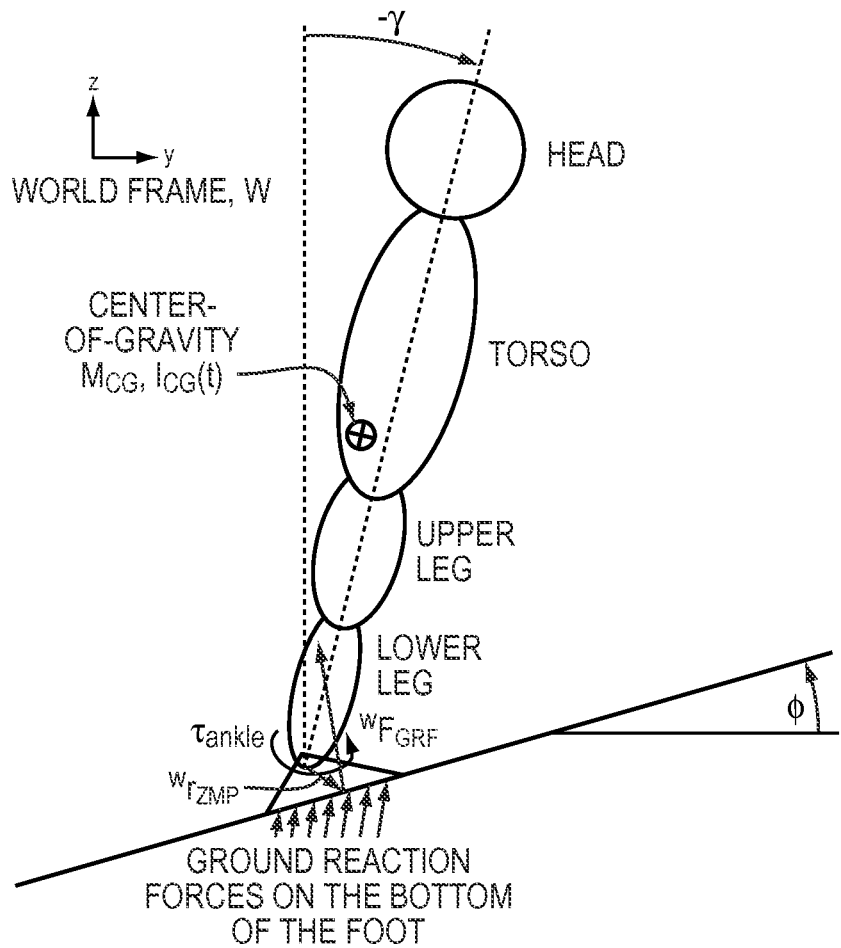
FIG. 23A is a schematic illustration of the human balance problem on an inclined slope.

FIG. 23A illustrates the generic problem of achieving balance on an incline of variable (positive or negative) slope. The problem appears to involve a multi-link, "inverted pendulum" problem, amenable to a non-linear feedback control implementation. In such solutions, knowledge of the link angles and the mass properties of the links (in this case, leg segments, torso, head and arms) are used to explicitly stabilize the multi-link system. But such explicit inputs are not contained within most embodiments of a lower-extremity prosthetic, orthotic or exoskeleton apparatus and would therefore be difficult if not impossible to implement and package reliably on the wearer. Further, in some instances, the wearer will have one intact leg, so part of the stabilization will be achieved outside of the lower-extremity prosthetic, orthotic or exoskeleton apparatus, wherein the lower-extremity prosthetic, orthotic or exoskeleton apparatus augments the function of the intact leg.

Figure 23B:
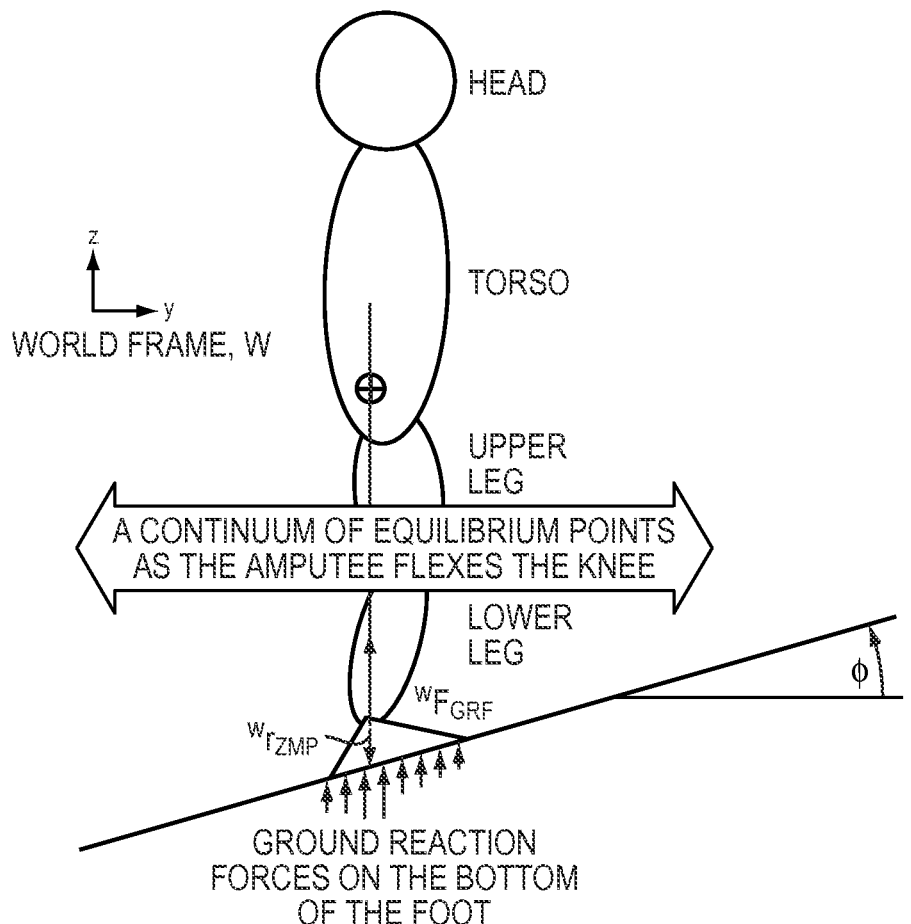
FIG. 23B is a schematic illustration of acceptable solutions to the balance problem based on variable knee flex by a wearer.

In addition, FIG. 23B shows that there is a continuum of acceptable solutions to the balance problem. Specifically, there are an infinite number of bent-knee solutions that are entirely acceptable and even desirable depending on human intent (e.g., picking up heavy luggage or boxes or to achieve balance while playing a game). So we see that the desired solution will employ intrinsic (to the lower-extremity prosthetic, orthotic or exoskeleton apparatus) sensing that complements the intact balance-producing body components to achieve equilibrium in alignment with human intent.

Figure 23C:
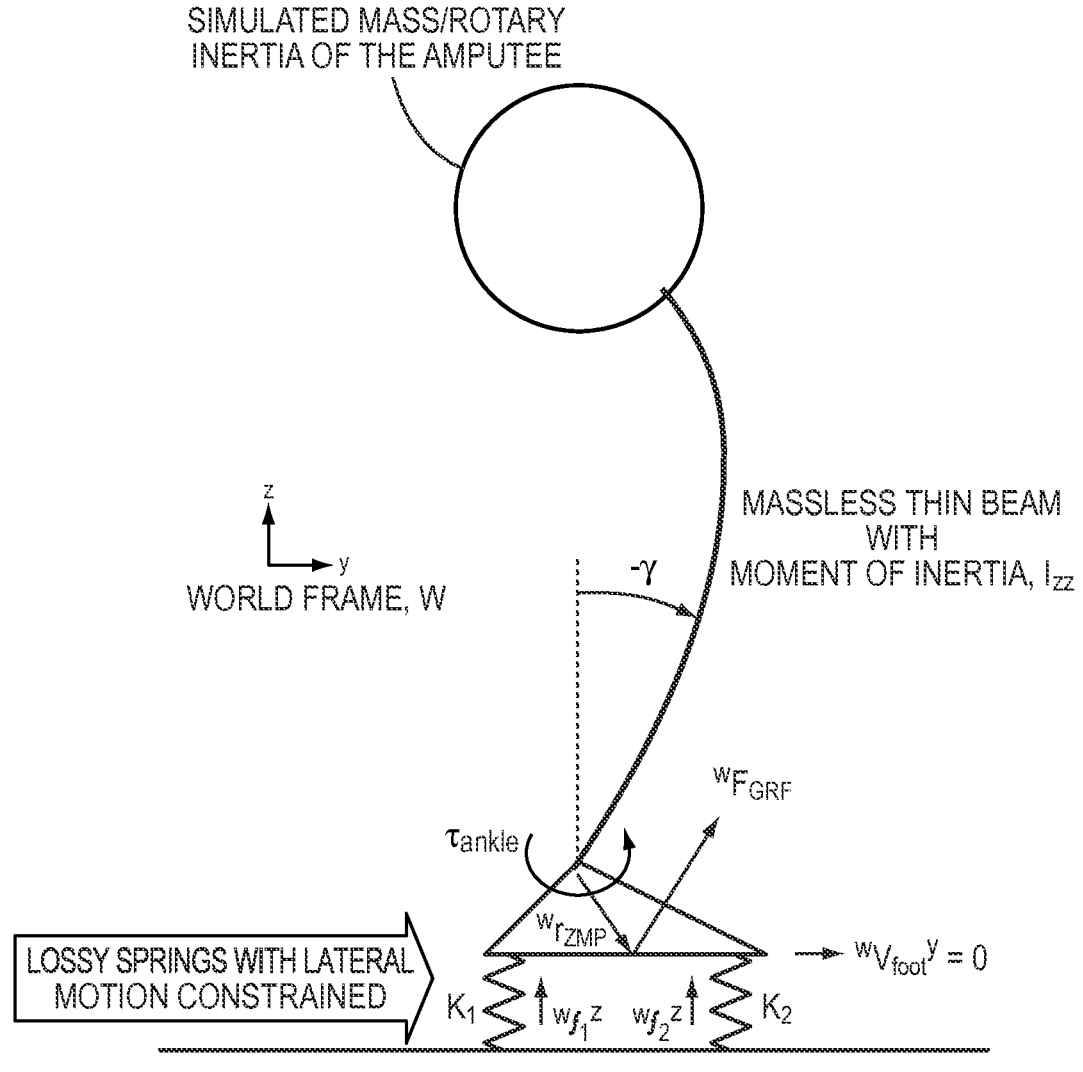
FIG. 23C is a schematic illustration representing the human body and how intrinsic sensing can be used to balance the wearer on level ground.

The solution employed in some embodiments of the lower-extremity prosthetic, orthotic or exoskeleton apparatus uses a simplified representation of the problem as modeled in FIG. 23C. In this representation, intrinsic sensing of lower leg member inertial state, ankle joint angle and inertially-referenced, ground reaction force, are used as the stabilization feedback that drives ankle torque (e.g., torque provided to the ankle joint by a linear actuator of a prosthetic apparatus). The body is modeled as a series of masses (only one shown in the figure) on a massless, thin, buckling beam with time-variable stiffness and moment-of-inertia.

Balance is achieved based on the following details. A desirable equilibrium is achieved when the following conditions are satisfied:

1. ''FGRF aligns with World z;

2. The line connecting the zero moment pivot and the ankle joint aligns with the World z unit vector; and 3. All time derivatives of the inertial lower leg member angle, $\gamma$, and ankle joint angle,?, are zero.

A feedback control law is then derived that drives each of these conditions into equilibrium based on the following:

$$\tau_{ankle} \dot{=} -\hat{I}(t)_{CG}\underline{k}^*(s)[^w\gamma_{CoP}{}^\gamma {}_wF_{GRF}{}^\gamma\gamma]^T \qquad \text{EQN. 40}$$

where $$\underline{k}^*(s)=[k^*_r(s)k^{*F}(s)k^*_\gamma(s)] \qquad \text{EQN. 41}$$

optimizes the quadratic cost index, J, where $$J = \int_0^\infty (\tau_{ankle}^2 + \underline{k}^T[\gamma\dot\gamma\ddot\gamma]^T[\gamma\dot\gamma\ddot\gamma]^T\underline{k})dt \qquad \text{EQN. 42}$$

and $$\underline{k} = \lfloor k_\gamma\ \ k_{\dot\gamma}\ \ k_{\ddot\gamma} \rfloor \qquad \text{EQN. 43}$$

where the components of k are chosen to emphasize link angle dynamic contributions to the cost index. In this embodiment, the control law solution is provided by the linear-quadratic regulator (LQR) methodology. In layman's terms this means that the settings of a (regulating) controller governing either a machine or process are found by using the above mathematical algorithms and minimizing a cost function with weighting factors supplied by a human. The "cost" (function) is often defined as a sum of the deviations of key measurements from their desired values. In effect this algorithm therefore finds those controller settings that minimize the undesired deviations, for example, deviations from desired work performed by a prosthesis for the wearer. Often the magnitude of the control action itself is included in this sum as to keep the energy expended by the control action itself limited. In effect, the LQR algorithm optimizes the controller based on an engineer's specification of the weighting factors. The LQR algorithm is, at its core, just an automated way of finding an appropriate state-feedback controller.

Use of the quadratic cost index is not required; however, in one embodiment, use of the quadratic cost index as an optimization criterion creates an objective framework for analysis and for in-office customization for wearers of the lower-extremity prosthesis to achieve an acceptable feel as the system works to maintain the wearer's equilibrium on different terrain. It is not uncommon to find that control engineers prefer alternative conventional methods like full state feedback (also known as pole placement) to find a controller over the use of the LQR algorithm. With these the engineer has a much clearer linkage between adjusted parameters and the resulting changes in controller behavior.

Wearer Assist in Getting Up from a Chair

Figure 24A:
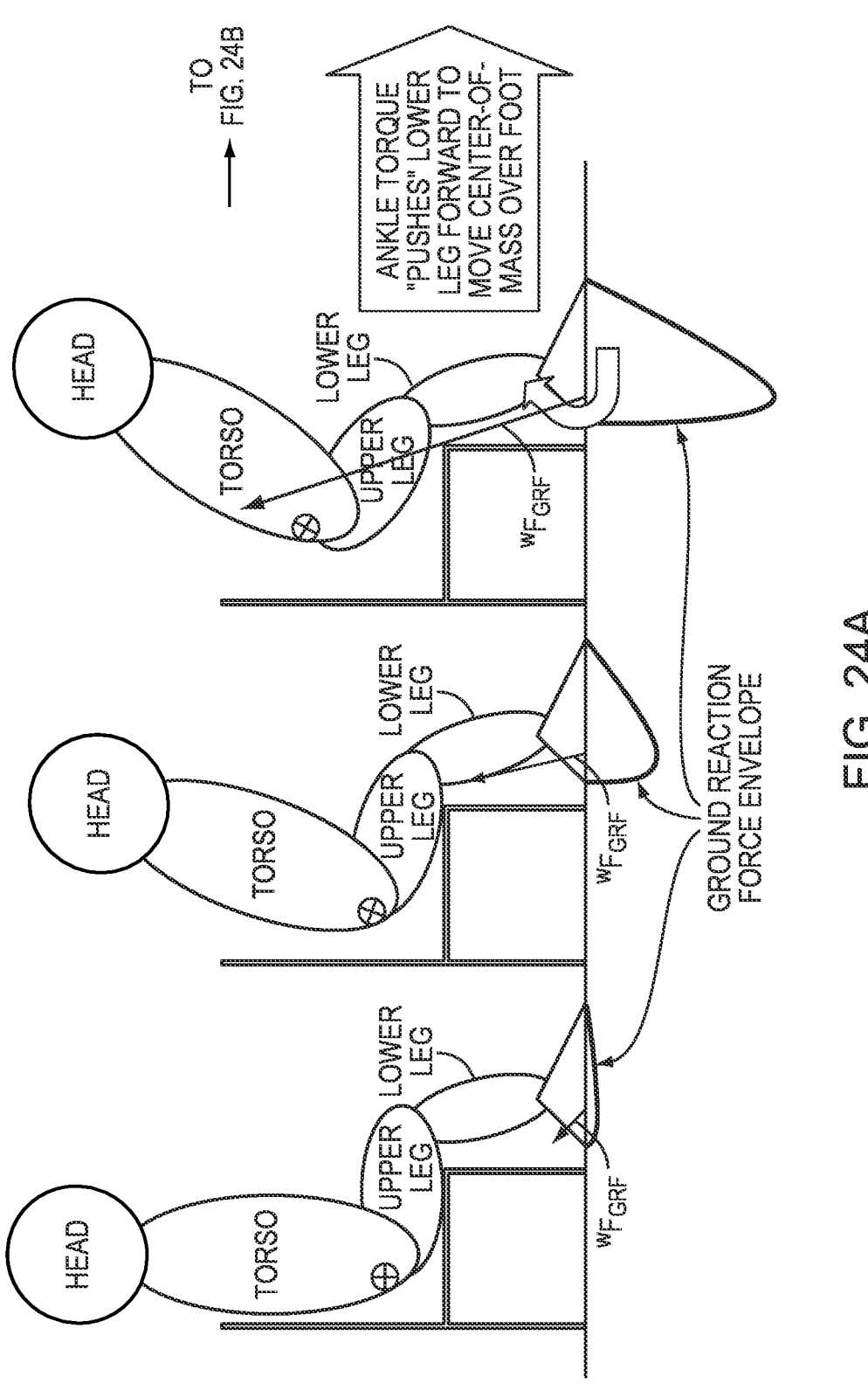
FIGS. 24A-24C are schematic illustrations for a method for balancing a wearer as the wearer stands up from a chair, according to an illustrative embodiment of the invention.
Figure 24B:
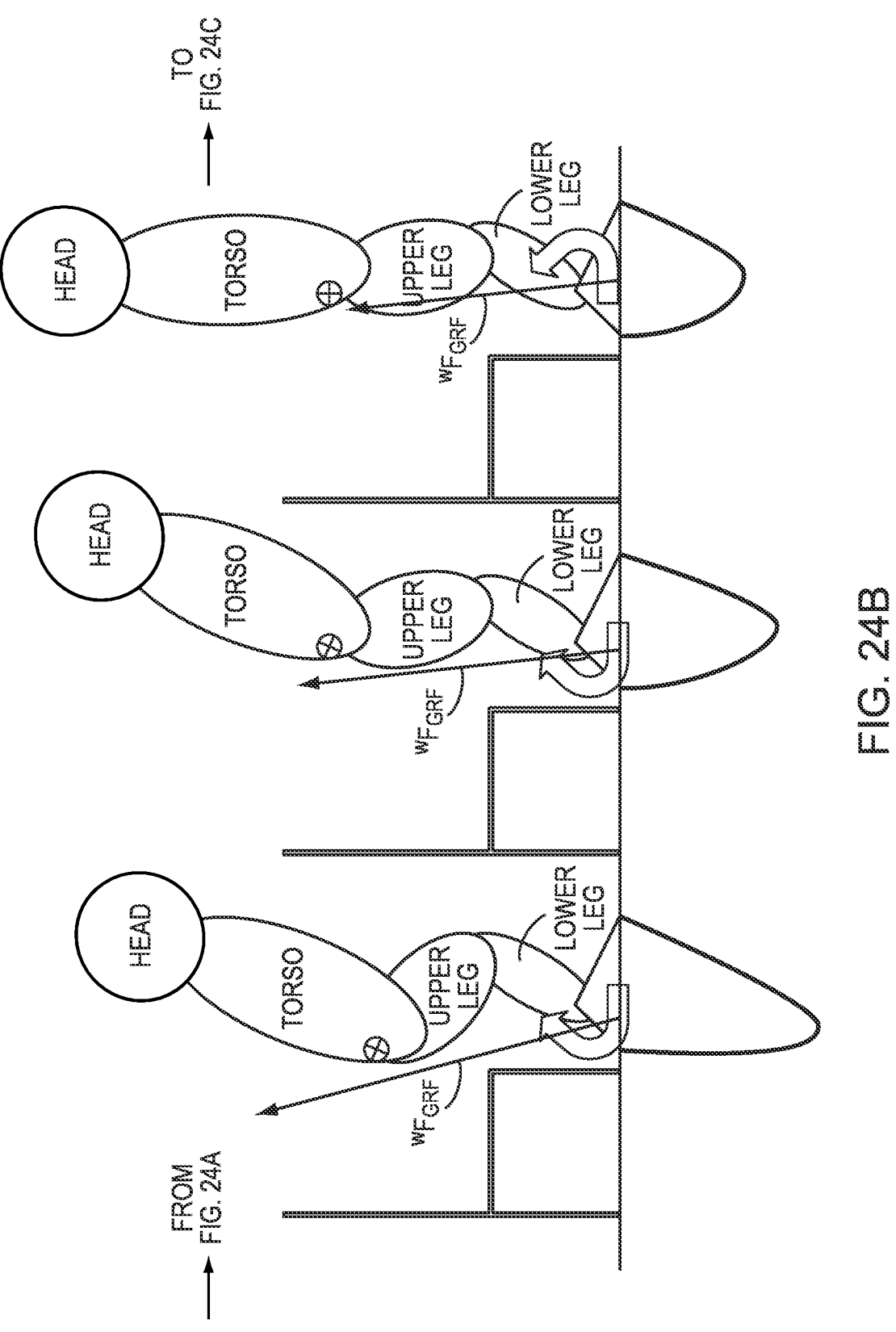
Figure 24C:
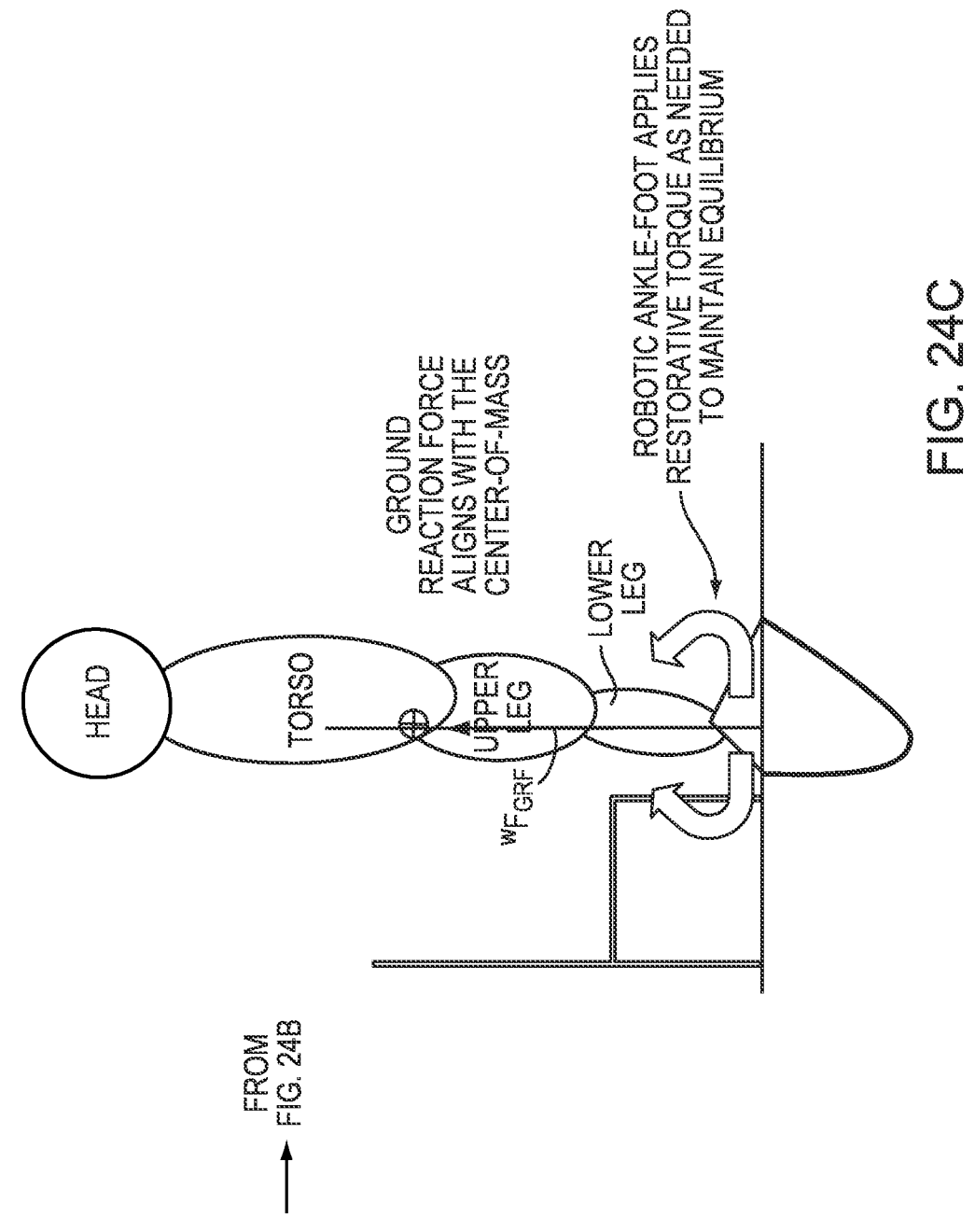

FIGS. 24A, 24B and 24C illustrate a method for applying a balancing control law to assist a wearer of a lower-extremity prosthetic apparatus in getting up from a chair, according an illustrative embodiment of the invention. The Timed Get Up and Go (TUG) is often used as an experimental means to evaluate dynamic and functional balance. Wearers are given a verbal instruction to stand up from a chair, walk 3 meters, cross a line marked on the floor, turn around, walk back, and sit down. To achieve good "TUG" performance, leg prostheses often have a "stand up" and "sit down" button to create the behavioral context for the prosthesis' control system. In the lower-extremity prosthetic apparatus incorporating principles of the present invention, in one embodiment there is no explicit requirement to set behavioral context by, for example, pushing a button. Sitting, standing up and sitting down behavioral context is identified by the intrinsic sensors of the prosthetic apparatus. Control behavior during standing and sitting is simply part of maintaining the wearer's equilibrium.

FIGS. 24A, 24B and 24C illustrate how the intrinsic balance control algorithm works to augment the wearer as she stands up from a chair. Referring to FIG. 24A, initiation of the sitting to standing transition involves three states. In the first, the foot is off the ground or only lightly touching it. The prosthetic apparatus (e.g., apparatus 1700 of FIGS. 17A-17E) knows the mass of the wearer; the inertial orientation of the lower leg member and foot member; and the ground reaction force (as determined, for example, with respect to FIG. 11A). The apparatus therefore "knows" or senses that the wearer is sitting. As the wearer begins to stand up, the increase in ground reaction force is noted and the state of the foot (foot flat) is known via the inertial measurement unit measurements and ankle joint angle sensor measurements. The intrinsic balance control law execution begins. During this second state, the disequilibrium sensed by the imbalance in the ground reaction force is used to drive the lower leg member (e.g., driven forward by the controller 1762 commanding the linear actuator 1716 to increase the torque applied to the ankle joint 1740) forward as a means of pulling the torso (center-of-mass) over the ankle joint.

Referring to FIG. 24B, the intrinsic balance control continues to drive the wearer into equilibrium in front of the chair. FIG. 24C shows the wearer in mid-stance equilibrium, ready to begin walking if desired. As shown, wearer intent, and more specifically the sitting/standing behavioral context can be derived by sensing that is intrinsic to the prosthetic apparatus. The implementation cost and complexity of explicit context switching (pressing of buttons) is thereby avoided. The prosthetic apparatus complements and augments the body function in a natural way.

The ankle torque induced by the ground reaction force (ORF) is a preferred way to achieve exponential hardening during mid-stance. Unlike use of the torque on the lower leg (e.g., torque measured using the structural element 1732 of FIG. 17A), the GRF-computed ankle torque measures the torque applied by the ground on the ankle joint. The GRF is often measured by force plates in gait research settings and is thereby used as a measure of how an intact ankle interacts with the ground while walking. The GRF establishes what is the biomimetic ankle behavior in different terrain contexts. A benefit of using the GRF as the means by which to achieve exponential hardening is the ease by which performance can be measured relative to biomimetic references. Further, use of this measure ensures that invariance to terrain orientation since it derives from intrinsic inertial sensing (e.g., using the inertial measurement unit 1720 of FIG. 17A).

Stand-up assistance can also be implemented using the knee orthosis depicted in FIGS. 22A-C or more generally any active knee orthosis or prosthesis. The seemingly simple task of elevating oneself from a sitting to a standing position is actually a complex task that incorporates the participation of the knee and hip extensors to apply lifting torque and restorative balance in a step-wise sequence of actions. FIGS. 29A-D depicts the ordinary stand-up sequence for a healthy person, which involves four phases: sitting, shown in FIG. 29A; (b) repositioning the knee over the foot in preparation for standing up, shown in FIG. 29B; (c) the transition from sitting to standing, shown in FIG. 29C and (d) balancing once the body has been lifted, shown in FIG. 29D.

FIGS. 30A-D depicts the problems in implementing the same stand-up sequence for a person wearing an active leg orthosis or prosthesis, because some of those same four phases cannot be carried out. More specifically, starting at the seated position, shown in FIG. 30A, most orthotic or prosthetic wearers maintain sufficient strength in their arms to position themselves in a chair, thus allowing them to preposition the knee and torso over the ankle and implement phase b, shown in FIG. 30B. However, the lack of strength in the quadriceps and/or hip extensors prevents the rotation in phase c that lifts the upper leg and torso out of the chair, indicated by the X 3010 in FIG. 30C. In addition, in the absence of sufficient extensor torque at the knee and hip, it is virtually impossible for the patient with inadequate knee and/or hip muscular strength to decelerate the torso and to maintain balance once the upright posture is achieved, indicated by the X 3020 in FIG. 30D.

FIGS. 31A-D depicts how an active knee apparatus such as an active orthosis (depicted in FIGS. 22A-C) or an active knee prosthesis can be used to assist the stand-up sequence for a patient suffering from limb pathology. This requires the ability to recognize that the user is currently seated, and also an ability to distinguish between a user's desire to remain seated and the user's desire to start standing.

Figure 32:
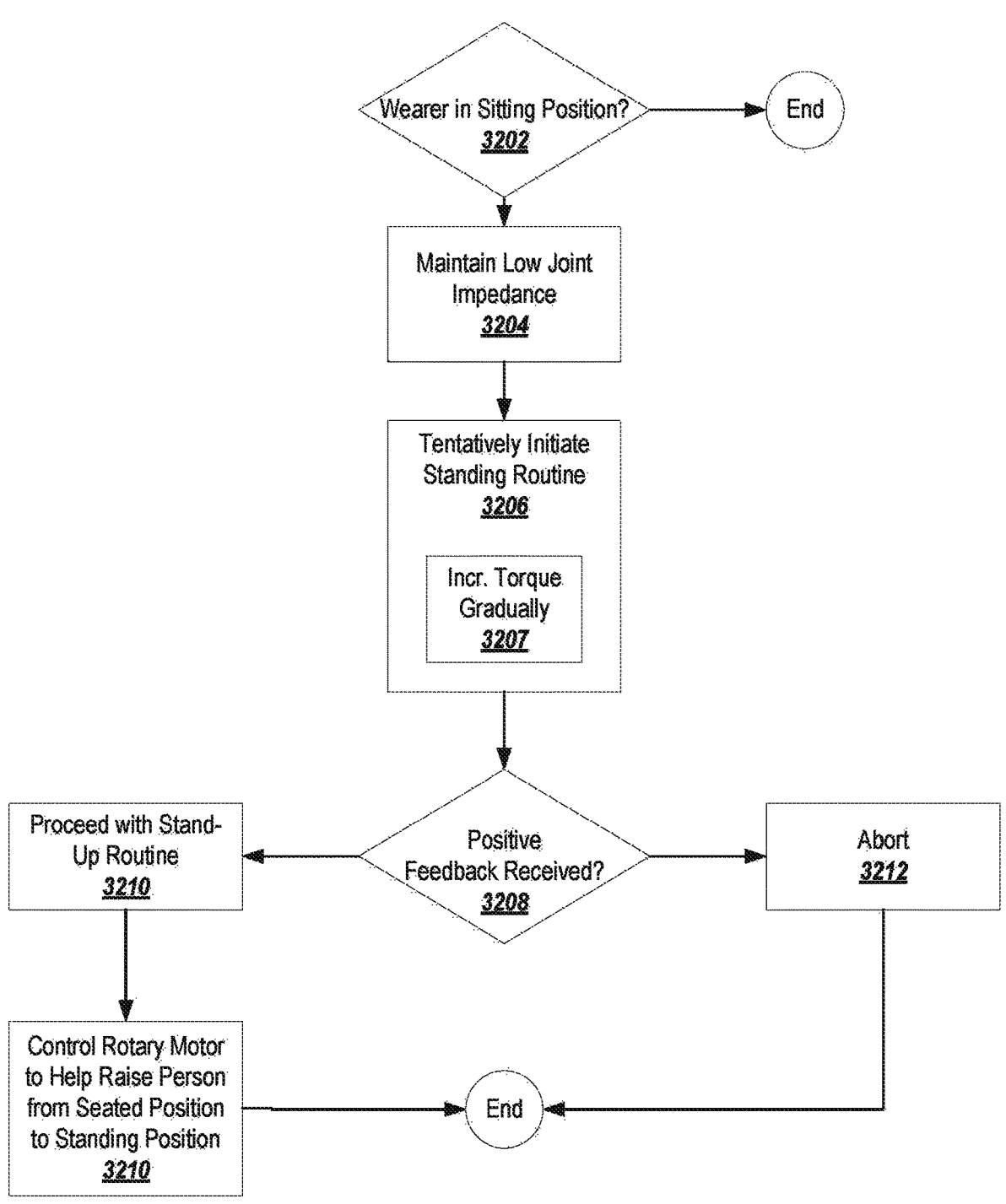
FIG. 32 depicts a flowchart describing the steps performed in FIGS. 31A-D.

One indicator that the user is currently seated is when the thigh is substantially horizontal as shown in FIG. 31A. The attitude of the thigh may be determined using inertial sensors mounted in the knee apparatus that measure the gravity vector in relation to the thigh coordinate system, because in a seated position the gravity vector lies principally in the x-y plane of the thigh (orthogonal to the z-axis). Another indicator of being in a seated position is based on the rotation angle of the shank in relation to the thigh (which can be obtained using an angular encoder) because in a relaxed sitting positions, the ankle joint is typically well-forward of the knee. These conditions can be detected (block 3202 of FIG. 32) and relied on by the system to remain in the seated mode, by, for example, maintaining a low joint impedance consistent with a relaxed, sitting position (block 3204 of FIG. 32).

These same sensors can then be used to detect the user's desire to transition to a standing position by detecting when the ankle joint has been placed more nearly under the knee joint as shown in FIG. 31B. When this situation is detected, the system preferably attempts to verify the user's desire to stand by tentatively initiating a stand-up routine (block 3206 of FIG. 32). If the system received positive feedback from the user (block 3208 of FIG. 32), the stand-up routine proceeds (block 3210 of FIG. 32). If, however, the system does not receive positive feedback from the user, the stand-up routine is aborted (block 3212 of FIG. 32).

This tentative initiation of a stand-up routine may be implemented by having the knee apparatus apply increasing torque 3110 gradually in accordance with the estimated upward and forward velocity of the hip joint (block 3207 of FIG. 32), shown in FIG. 31C. Positive feedback can be provided by the user by trying to lift her body with her arms to displace the hip joint vertically to assist the knee apparatus in lifting. In this situation, the hip will displace more vertically, and the gravity vector will begin to transition towards the z-axis. The system interprets those conditions as verification that the user really does want to stand. In response, the system applies more torque to continue lifting the user (block 3210 of FIG. 32).

Alternatively, positive feedback from the user could be in the form of a measured electromyographic signal from the wearer's thigh and/or hip musculature using surface or implanted electrodes. More specifically, once the apparatus has detected that the knee joint has moved forward the ankle joint, the standup routine could be initiated by the wearer flexing her quadriceps and/or hip extensors. The apparatus would then measure these electromyographic signals, amplify and filter each muscle output, and extract signal features such as magnitude, variance, and/or frequency using conventional techniques. These extracted features could then be used to discern the user's intent to either remain seated or to initiate a stand-up routine.

Optionally, pressure sensors in the foot may be employed to detect the ZMP, and a torso mounted IMU may be used to detect CMP, and the associated ground reaction force vector may be used as feedback to balance the wearer over the lower limb. These pressure sensors preferably communicate with the controller in the knee apparatus using a suitable wireless interface (e.g., Bluetooth). As the patient approaches the standing state, the knee apparatus applies restorative torque 3120 to assist the wearer in achieving balance while in the standing state, shown in FIG. 31D. Application of knee torque will steer the force vector fore and aft of the wearer center-of-gravity, thereby nulling ZMP-CMP over time. Examples of suitable approaches for implementing this can be found in U.S. Pat. No. 7,313,463 which is incorporated herein by reference.

Note that the user may occasionally shift positions in her chair while seated in ways that will also trigger a tentatively initiation of a stand-up routine. However, the applied knee apparatus torque will be relatively small at first and will die out exponentially over time (e.g., in 1-2 seconds) if positive feedback is not received from the user. An example of no positive feedback in a non-myoelectric system would be when the user does not try to lift her body with her arms and the hip joint does not begin to displace. An example of no positive feedback in a myoelectric system would be when the user does not substantially activate her knee and/or hip extensors to confirm her intent to the stand-up intent. If positive feedback is not received, the system will abort the stand-up routine and return to a relaxed seated state.

Optimization Methods

Figure 25A:
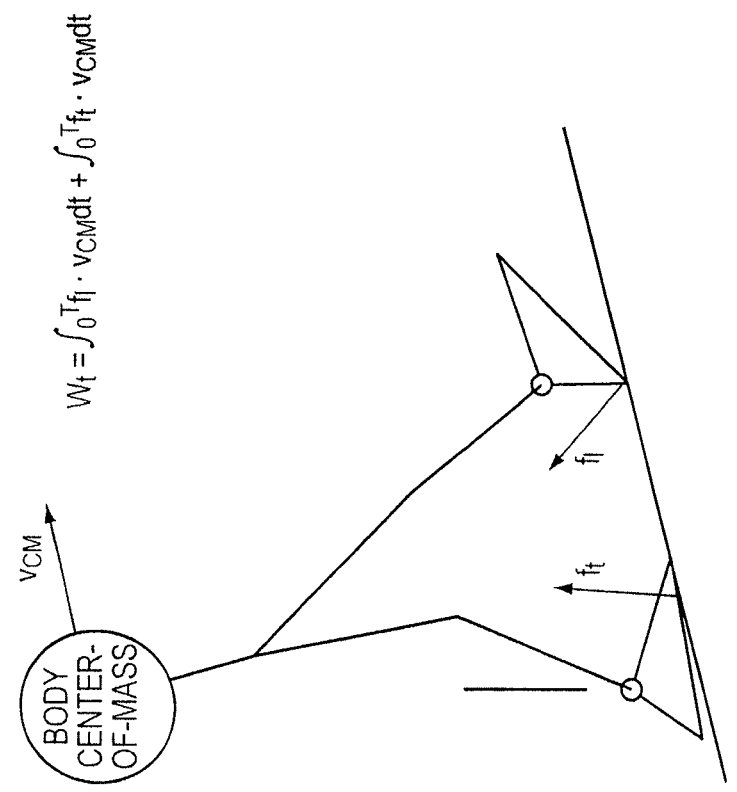
FIG. 25A illustrates a definition of transfer work.
Figure 25B:
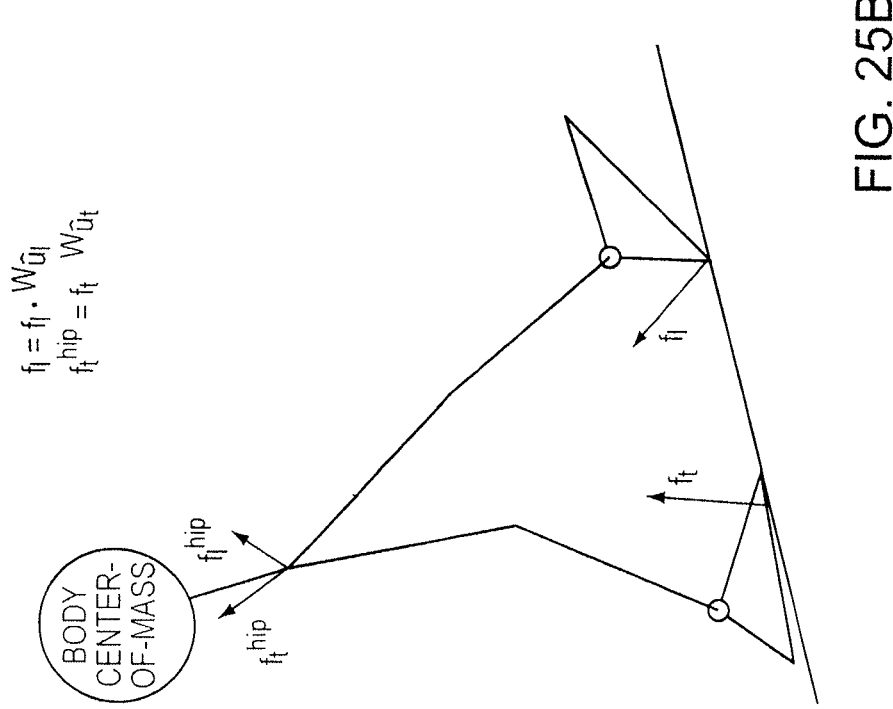
FIG. 25B illustrates a definition of hip impact forces.

FIGS. 25A and 25B are schematic illustrations for controlling a lower-extremity apparatus based on a stochastic optimization of 1) the transition work, $W_t$, performed to transfer weight from the trailing leg to the leading leg during the double-support phase of the gait cycle 2) minimizing hip impact force and force rate or 3) minimizing a combination of both cost (objective) functions. FIG. 25A illustrates the simplified model used to calculate transition work. FIG. 25B illustrates the simplified model used to calculate hip impact force and force rate.

The term stochastic denotes that the optimization minimizes the expected value of the objective function subject to hip impact force and force rate constraints, assuming probability (likelihood) functions for human intent; biomechanical feedback (including walking speed); terrain context, and terrain property. The optimization is achieved through modification of impedance, torque and position control parameters within the control algorithms. Practically speaking, the transfer energy is minimized, and the hip impact force constraints satisfied, by minimizing the negative impact of foot strike forces and maximizing the positive impact of reflex-induced ground forces on the hybrid system energy.

The optimization described above can be implemented in real-time by introducing "evolutionary" perturbations in the key components that contribute to the biomimetic behavior and measuring the transfer energy that arises from those evolutionary perturbations. The transfer energy can be estimated using biomechanical models to augment the inertial measurement unit feedback, or, in special cases, temporary inertial measurement unit subsystems (an IMU mounted on the body in the form of a belt around the torso and/or upper leg) could be used to facilitate estimate of torso pose and body center-of-mass velocity. Using the Fletcher-Powell method (or other suitable optimization method known to those skilled in the art), an intelligent evolution of parameters can be introduced and an optimum can be calculated. This optimum could, due to the rehabilitative effects of the augmentation, change over time. By applying these evolutionary perturbations continually and slowly over time, the optimum can be achieved on a continual basis. Or, as would be the case at the initial fitting or medical checkup of the prosthesis or orthosis, this evolutionary optimization could occur over a much shorter interval, say, in five to ten minutes.

The following is a description of the different phases of a subject's gait cycle and, in one embodiment, the steps performed by an ankle joint prosthesis according to principles of the invention are for sensing the operation of and for controlling the ankle-joint prosthesis.

Controlled Plantarflexion

At impact, check that the ground reaction force and the zero moment pivot correspond with the part of the foot that we expect (from the terrain discrimination model) to hit the ground first. Confirm that there is a corresponding change in the ankle angle (or ankle torque) and that the appropriate end of the foot is stationary. After impact look for a condition where the local terrain slope corresponding to the inertial foot-flat angle is significantly less than expected. Saturate ankle spring restoring force and increase damping when this is detected. For terrain discrimination, based upon the biomechanical model feedback confirm that the terrain hypothesis (slope vs. stair) is correct and that the wearer hasn't tripped. For example, a tripping event on a stair might be detected as a large negative force in the y-direction instead of a large z-force centered on the forward part of the foot. For terrain texture, either the heel or the forward part of the foot will impact first. The non-elastic component of the depression associated with this impact will be computed. On hard ground, this depression should be negligible—only an elastic deformation (foot module, linear actuator) will be observed. In mud or soft ground, terrain plasticity will be observed by looking at the trajectory of the impacting foot segment. The terrain plasticity will be used as an attenuator on the network that is performed on this walking cycle. Slipping can also be detected by noting the forward velocity of the impacting foot segment after impact. An escalator or people mover can be detected by noting that the shank angle is not rotating in accordance with the forward velocity of the foot, signaling that the wearer is well balanced and is stepping onto a moving surface. For impedance control of the ankle joint apply optimal impedance using estimated terrain-referenced velocity attack angle (y) lower-limb momentum, estimated terrain slope and terrain property. For reflex control, in the event that slipping is detected, a balance-restoring reflex will be generated to move the knee over the ankle. For balance control, optimal balance will normally be achieved by inertially referencing the spring equilibrium after the local terrain slope estimate is updated at foot-flat. In the event that the terrain is slippery, the algorithms that maintain balance will introduce a positive torque "reflex" to "pull" the shank forward in order to assist the wearer as she works to position the knee over the ankle—thereby getting the body center-of-mass aligned with the estimated ground reaction force.

Controlled Dorsiflexion

Once foot flat is detected, the controller inertially references the spring equilibrium angle for this local terrain slope so that when the wearer is standing in alignment with gravity on this slope, no restoring torque is applied by the ankle under static conditions. At this point, the local terrain context is now known precisely. Foot reference coordinates at this "foot flat" position are also defined for use in assessing the impact of terrain texture. For terrain texture, the algorithms use integrated measures of slip and deformation relative to the "foot flat" reference to update the terrain property model-specifically to measure plasticity of the surface and it's slipperiness by measuring how the impacted foot segment moves between foot-strike and foot flat. These measures can be used to attenuate ankle impedance and net work (reflex torque in late plantar flexion. Also, if "slipping" is detected between foot-strike and foot-flat, an algorithm implemented in the controller, also looks at shank angular velocity (how the knee is moving in relation to the ankle joint) to discriminate between a slippery surface and an escalator/people-mover. In either event, the zero-velocity update would not be scheduled since no reliable "ankle joint at zero velocity" will be available on this step. In the event that the terrain is slippery, special measures will need to be invoked by the balance function. In the case where the foot lands on a moving escalator or people mover, nominal impedance can be used on the new inertial frame. For impedance control, the control system can apply optimal impedance that maintains an inertially-referenced equilibrium angle; creates a walking speed-dependent stiffness (lower stiffness for faster walking speed) to enable a higher level of net work; and reduces the stiffness in slippery or highly-plastic surfaces. For reflex control in the event that slipping is detected, a balance-restoring reflex will be generated to move the knee over the ankle. For balance control, optimal balance will normally be achieved by inertially referencing the spring equilibrium after the local terrain slope estimate is updated at foot-flat. In the event that the terrain is slippery, the algorithms that maintain balance will introduce a positive torque "reflex" to "pull" the shank forward in order to assist the wearer as she works to position the knee over the ankle—thereby getting the body center-of-mass aligned with the estimated ground reaction force.

Powered Plantarflexion

The model monitors slippage and sinking into the surface and identifies ankle torque limits that can be used to make ambulation efficient in these conditions. For terrain texture, terrain property estimates are refined in this state and are used as an input to the impedance, reflex and balance functions. For impedance control, nominal impedance parameters will be modified to accommodate changes in walking speed, terrain surface characteristics and deformation and foot slippage. A special "force field"-typically a non-linear actuator force that exponentially increases as the ball-nut approaches a predefined end-stop limit—is applied by the motor controller to make sure that the $K_3$ spring energy (in the parallel elastic member) does not exceed the lower bound of its fracture limit. For reflex control, reflex amplitude will be adjusted to account for the net work "setpoint" from the biomechanical models in combination with the degree to which the terrain can support production of this net work. For balance control, optimal balance will normally be achieved by inertially referencing the spring equilibrium after the local terrain slope estimate is updated at foot-flat. In the event that the terrain is slippery, the algorithms that maintain balance will introduce a positive torque "reflex" to "pull" the shank forward in order to assist the wearer as she works to position the knee over the ankle—thereby getting the body center-of-mass aligned with the estimated ground reaction force.

Early Swing

For early swing, shortly after the toe leaves the ground, the model monitors the inertial trajectory of the ankle, heel and toe and determines when the ankle can be dorsiflexed back to its neutral position without-being obstructed by the terrain. The model computes an optimal trajectory with suitable impedance gains and feed-forward torque to move the ankle to the neutral position (to avoid tripping hazards) in the quickest, efficient and stable fashion. For terrain discrimination, the model starts to keep track of the swept ("no contact" with foot member) volume through which the foot has moved thereby informing the adaptive ankle positioning function in late swing when a toe-down solution is the only viable solution (e.g., to land on a shallow stair or ledge). For impedance control in early swing, a neutral value of impedance is applied by the controller. A force-field function is applied to make sure that the linear actuator does not impact the hard stop (end of travel) —a condition that could cause the actuator to stick there (at the end of travel). For impedance control in early swing informed by the hybrid biomechanical model, the controller controls impedance to create a trajectory that exponentially drives the equilibrium position (ankle angle setpoint) to the desired neutral position. A feed-forward torque function is applied to reduce the interaction between impedance characteristics and the ankle angle following error that could otherwise introduce overshoot and ringing, for instance.

Late Swing

For terrain discrimination, the model keeps track of the "clear" volume through which the foot has moved thereby informing the adaptive ankle positioning function in late swing when a toe-down solution is the only viable solution, say, to land on a shallow stair or ledge. More generally, the ankle trajectory is monitored and pattern recognition functions are used to determine the likelihood that the foot will be landing on a stair/ledge as opposed to a sloping surface. One simple way that we have found to discriminate between the two conditions is to measure the angle that the ankle velocity makes in relation to vertical; where in various experiments it was determined that when this angle is less than 10 degrees, the foot will land on a horizontal step. For impedance control, informed by the terrain discrimination model, the ankle trajectory (equilibrium) will be modified by the controller as needed to avoid tripping hazards. For example, if the terrain discrimination function assigns the maximum likelihood to stair ascent, additional dorsiflexion may be commanded to make sure that the toe does not catch on the stair or ledge. As before, the hybrid biomechanical model plans a continuously updatable equilibrium trajectory that can be followed safely and in a stable fashion with tight tolerances. In the late-stance state, the biomechanical model computes the optimum equilibrium angle and ankle impedance that will minimize an objective function that includes some combination of transfer energy and knee-hip impact forces. This optimization function could be implemented via table lookup in the State Machine ROM. Or, in the preferred embodiment, the State Controller function will perform the optimization in real-time, using approximations of the rigid-body dynamics, to compute and optimize the objective functions.

Variations, modifications, and other implementations of what is described herein will occur to those of ordinary skill in the art without departing from the spirit and the scope. of the invention as claimed. Accordingly, the invention is to be defined not by the preceding illustrative description but instead by the spirit and scope of the following claims.

We claim:

1. An active orthotic or prosthetic apparatus for a wearer comprising:

a thigh member;

a lower leg member;

a knee joint for connecting the thigh member to the lower leg member;

a rotary motor comprising a motor shaft output;

a motor drive transmission assembly coupled to the motor shaft output;

a drive transmission assembly coupled to the output of the motor drive transmission assembly, with an output of the drive transmission assembly coupled to the lower leg member for applying torque to the knee joint to rotate the lower leg member with respect to the thigh member;

at least one sensor having at least one output from which a position of the knee joint with respect to an ankle joint can be determined while the wearer of the apparatus is in a seated position; and a controller configured to:

calculate, by an inertial measurement unit, an upward and forward velocity of a hip joint, the upward and forward velocity measured as a function of a displacement of the hip joint in three-dimensional space, determine when the knee joint is moved to a position that is forward of the ankle joint based on the least one output of the at least one sensor, and in response to said determination, controls the rotary motor to help raise the wearer from a seated position to a standing position by increasing a torque of the knee joint, the torque increasing initially to a first relatively small value and configured to be reduced absent positive feedback confirming the user's intent to stand, and increasing gradually to a second relatively large value in accordance with the upward and forward velocity of the hip joint in the presence of the positive feedback.

2. The apparatus of claim 1, wherein the at least one sensor comprises an inertial sensor that measures a gravity vector in relation to a thigh coordinate system.

3. The apparatus of claim 1, wherein the at least one sensor detects a rotation angle of the lower leg in relation to the thigh.

4. The apparatus of claim 1, wherein the controller is programmed to maintain a low joint impedance in response to a determination that the wearer is in the seated position.

5. The apparatus of claim 1, wherein the controller controls the rotary motor so that as the wearer approaches the standing state, restorative torque is applied to assist the wearer in achieving balance while in the standing state.

6. The apparatus of claim 1, further comprising at least one pressure sensor configured to measure a force being applied to the wearer's foot.

7. The apparatus of claim 1, wherein the controller controls the rotary motor to help raise the wearer from the seated position to the standing position by increasing knee torque in accordance with a measured electromyographic signal from at least one of a knee muscle and a hip muscle.

8. The apparatus of claim 1, wherein the torque is configured to be reduced exponentially absent the positive feedback.

9. A method of controlling a knee orthosis or prosthesis having at least one actuator for applying a torque to the knee joint to rotate the lower leg member with respect to the thigh member, the knee orthosis or prosthesis being worn by a wearer, the method comprising the steps of:

detecting the position of the wearer's knee with respect to the wearer's ankle while the person is in a seated position;

determining when the knee is moved to position that is forward of the ankle based on a result of the detecting step, and generating an output indicative thereof;

calculating, by an inertial measurement unit, an upward and forward velocity of a hip joint, the upward and forward velocity measured as a function of a displacement of the hip joint in three-dimensional space; and actuating, in response to the output, the at least one actuator of the knee orthosis or prosthesis to help raise the wearer from the seated position to a standing position, the torque increasing initially to a first relatively small value and configured to be reduced absent positive feedback confirming the user's intent to stand, and increasing gradually to a second relatively large value in accordance with the upward and forward velocity of the hip joint in the presence of the positive feedback.

10. The method of claim 9, further comprising the step of measuring a gravity vector in relation to a thigh coordinate system.

11. The method of claim 9, further comprising the step of detecting a rotation angle of the wearer's lower leg in relation to the wearer's thigh.

12. The method of claim 9, further comprising the step of maintaining a low joint impedance in response to a determination that the wearer is in the seated position.

13. The method of claim 9, further comprising the step of applying restorative torque to assist the wearer in achieving balance while in the standing state.

14. The method of claim 9, further comprising the step of measuring a force being applied to the wearer's foot.

15. The method of claim 9, further comprising the step of increasing knee torque in accordance with measured electromyographic signals from at least one of a knee muscle and a hip muscle.

* * * * *